(12) United States Patent
Connor

(10) Patent No.: US 11,471,163 B2
(45) Date of Patent: Oct. 18, 2022

(54) INTRASACCULAR ANEURYSM OCCLUSION DEVICE WITH NET OR MESH EXPANDED BY STRING-OF-PEARLS EMBOLIES

(71) Applicant: Robert A. Connor, St. Paul, MN (US)

(72) Inventor: Robert A. Connor, St. Paul, MN (US)

(73) Assignee: Aneuclose LLC, St. Paul, MN (US)

( * ) Notice: Subject to any disclaimer, the term of this patent is extended or adjusted under 35 U.S.C. 154(b) by 491 days.

(21) Appl. No.: 16/660,929

(22) Filed: Oct. 23, 2019

(65) Prior Publication Data

US 2020/0054344 A1   Feb. 20, 2020

Related U.S. Application Data

(63) Continuation-in-part of application No. 16/541,241, filed on Aug. 15, 2019, now abandoned, and a continuation-in-part of application No. 15/865,822, filed on Jan. 9, 2018, now Pat. No. 10,716,573, said application No. 16/541,241 is a continuation-in-part of application No. 15/865,822, filed on Jan. 9, 2018, now Pat. No. 10,716,573, application No. 16/660,929, which is a continuation-in-part of application No. 15/861,482, filed on Jan. 3, 2018, now abandoned, said application No. 15/865,822 is a continuation-in-part of application No. 15/081,909, filed on Mar. 27, 2016, now abandoned, said application No. 15/861,482 is a continuation-in-part of application No. 15/080,915, filed on Mar. 25, 2016, now Pat. No. 10,028,747, which is a continuation-in-part of application No. 14/526,600, filed on Oct. 29, 2014, now abandoned, said application No. 15/861,482 is a continuation-in-part of application No. 14/526,600, filed on Oct. 29, 2014, now abandoned, said application No. 15/865,822 is a continuation-in-part of application No. 14/526,600, filed on Oct. 29, 2014, now abandoned, said application No. 15/081,909 is a continuation-in-part of application No. 14/526,600, filed on Oct. 29, 2014, (Continued)

(51) Int. Cl.
*A61B 17/12* (2006.01)
*A61B 17/00* (2006.01)

(52) U.S. Cl.
CPC .. *A61B 17/12172* (2013.01); *A61B 17/12113* (2013.01); *A61B 17/12163* (2013.01); *A61B 2017/00867* (2013.01)

(58) Field of Classification Search
CPC ........ A61B 17/12168; A61B 17/12151; A61B 17/12118; A61B 17/12177; A61B 17/12113; A61B 17/12172
See application file for complete search history.

(56) References Cited

U.S. PATENT DOCUMENTS 4,341,218 A    7/1982  U
4,364,392 A    12/1982 Strother et al.
(Continued)

*Primary Examiner* — Diane D Yabut
*Assistant Examiner* — Christina C Lauer

(57) ABSTRACT

This invention is an intrasaccular aneurysm occlusion device comprising: a net or mesh with a self-expanding resilient proximal portion (which is deployed close to the aneurysm neck) and an expandable flexible distal portion (which is deployed close to the aneurysm dome); and a "string of pearls" of embolic members which are inserted into the net or mesh.

4 Claims, 3 Drawing Sheets

Related U.S. Application Data now abandoned, which is a continuation-in-part of application No. 12/989,048, filed on Oct. 21, 2010, now Pat. No. 8,974,487.

(60) Provisional application No. 62/794,607, filed on Jan. 19, 2019, provisional application No. 62/794,609, filed on Jan. 19, 2019, provisional application No. 62/720,173, filed on Aug. 21, 2018, provisional application No. 62/589,754, filed on Nov. 22, 2017, provisional application No. 62/472,519, filed on Mar. 16, 2017, provisional application No. 62/444,860, filed on Jan. 11, 2017, provisional application No. 61/897,245, filed on Oct. 30, 2013, provisional application No. 61/126,047, filed on May 1, 2008, provisional application No. 61/126,027, filed on May 1, 2008.

(56) References Cited

U.S. PATENT DOCUMENTS

| | | | |
|---|---|---|---|
| 4,638,803 A | 1/1987 | Rand | |
| 5,041,090 A | 8/1991 | Scheglov et al. | |
| 5,334,210 A | 8/1994 | Gianturco | |
| 5,690,666 A | 11/1997 | Berenstein et al. | |
| 5,935,148 A | 8/1999 | Villar et al. | |
| 6,063,104 A | 5/2000 | Villar et al. | |
| 6,238,403 B1* | 5/2001 | Greene, Jr. | A61B 17/12145 606/108 |
| 6,346,117 B1* | 2/2002 | Greenhalgh | A61B 17/12022 606/200 |
| 6,350,270 B1 | 2/2002 | Roue | |
| 6,391,037 B1 | 5/2002 | Greenhalgh | |
| 6,511,468 B1 | 1/2003 | Cragg et al. | |
| 6,530,934 B1 | 3/2003 | Jacobsen et al. | |
| 6,585,748 B1 | 7/2003 | Jeffree | |
| 6,855,153 B2 | 2/2005 | Saadat | |
| 6,958,061 B2 | 10/2005 | Truckai et al. | |
| 7,083,643 B2 | 8/2006 | Whalen et al. | |
| 7,153,323 B1* | 12/2006 | Teoh | A61B 17/12113 623/1.23 |
| 7,695,488 B2 | 4/2010 | Berenstein et al. | |
| 8,597,320 B2 | 12/2013 | Sepetka et al. | |
| 8,974,512 B2 | 3/2015 | Aboytes et al. | |
| 8,998,947 B2 | 4/2015 | Aboytes et al. | |
| 9,157,174 B2 | 10/2015 | Kusleika | |
| 9,393,022 B2 | 7/2016 | Becking et al. | |
| 9,561,122 B2 | 2/2017 | Kusleika | |
| 9,592,363 B2 | 3/2017 | Griffin et al. | |
| 9,844,382 B2 | 12/2017 | Aboytes et al. | |
| 9,931,495 B2 | 4/2018 | Aboytes | |
| 9,955,976 B2 | 5/2018 | Hewitt et al. | |
| 10,130,372 B2 | 11/2018 | Griffin | |
| 10,314,593 B2 | 6/2019 | Bardsley et al. | |
| 10,327,781 B2 | 6/2019 | Divino et al. | |
| 10,342,548 B2 | 7/2019 | Duncan | |
| 10,383,635 B2 | 8/2019 | Wallace et al. | |
| 10,383,749 B2 | 8/2019 | Zhou et al. | |
| 10,398,441 B2 | 9/2019 | Warner et al. | |
| 10,405,966 B2 | 9/2019 | Johnson | |
| 10,406,010 B2 | 9/2019 | Bourang | |
| 10,420,862 B2 | 9/2019 | Sharma et al. | |
| 10,426,486 B2 | 10/2019 | Guo et al. | |
| 10,426,487 B2 | 10/2019 | Bachman et al. | |
| 10,433,853 B2 | 10/2019 | Divino et al. | |
| 2001/0034531 A1 | 10/2001 | Ho et al. | |
| 2002/0026210 A1 | 2/2002 | Abdel-Gawwad | |
| 2002/0026217 A1 | 2/2002 | Baker et al. | |
| 2002/0165572 A1 | 11/2002 | Saadat | |
| 2002/0169473 A1 | 11/2002 | Sepetka et al. | |
| 2003/0028209 A1 | 2/2003 | Teoh et al. | |
| 2003/0212419 A1 | 11/2003 | West | |
| 2004/0010263 A1 | 1/2004 | Boucher et al. | |
| 2004/0098027 A1 | 5/2004 | Teoh et al. | |
| 2004/0254625 A1 | 12/2004 | Stephens et al. | |
| 2005/0142163 A1 | 6/2005 | Hunter et al. | |
| 2006/0052816 A1 | 3/2006 | Bates et al. | |
| 2006/0116709 A1 | 6/2006 | Sepetka et al. | |
| 2006/0149309 A1 | 7/2006 | Paul et al. | |
| 2006/0155323 A1 | 7/2006 | Porter et al. | |
| 2006/0167494 A1 | 7/2006 | Suddaby | |
| 2007/0219578 A1* | 9/2007 | Solar | A61B 17/12113 606/200 |
| 2008/0281350 A1 | 11/2008 | Sepetka et al. | |
| 2009/0112249 A1 | 4/2009 | Miles et al. | |
| 2009/0287294 A1 | 11/2009 | Rosqueta et al. | |
| 2009/0318948 A1 | 12/2009 | Linder et al. | |
| 2011/0184451 A1 | 7/2011 | Sahl | |
| 2011/0196413 A1 | 8/2011 | Wallace et al. | |
| 2012/0239074 A1 | 9/2012 | Aboytes et al. | |
| 2012/0265287 A1 | 10/2012 | Sharma et al. | |
| 2012/0283768 A1 | 11/2012 | Cox et al. | |
| 2013/0116722 A1 | 5/2013 | Aboytes et al. | |
| 2013/0245667 A1 | 9/2013 | Marchand et al. | |
| 2014/0052233 A1 | 2/2014 | Cox et al. | |
| 2014/0135812 A1 | 5/2014 | Divino et al. | |
| 2014/0330299 A1 | 11/2014 | Rosenbluth et al. | |
| 2015/0005807 A1 | 1/2015 | Lagodzki et al. | |
| 2015/0196744 A1 | 7/2015 | Aboytes | |
| 2015/0209050 A1 | 7/2015 | Aboytes et al. | |
| 2015/0216684 A1 | 8/2015 | Enzmann et al. | |
| 2015/0272590 A1 | 10/2015 | Aboytes et al. | |
| 2015/0313605 A1 | 11/2015 | Griffin | |
| 2015/0342613 A1 | 12/2015 | Aboytes et al. | |
| 2016/0045201 A1 | 2/2016 | Rosenbluth et al. | |
| 2016/0213380 A1 | 7/2016 | O'Brien et al. | |
| 2016/0249934 A1 | 9/2016 | Hewitt et al. | |
| 2016/0249935 A1 | 9/2016 | Hewitt et al. | |
| 2016/0249937 A1 | 9/2016 | Marchand et al. | |
| 2016/0262766 A1 | 9/2016 | Aboytes et al. | |
| 2016/0367260 A9 | 12/2016 | Hewitt et al. | |
| 2017/0079661 A1 | 3/2017 | Bardsley et al. | |
| 2017/0086851 A1 | 3/2017 | Wallace et al. | |
| 2017/0095254 A1 | 4/2017 | Hewitt et al. | |
| 2017/0128077 A1 | 5/2017 | Hewitt et al. | |
| 2017/0156734 A1 | 6/2017 | Griffin | |
| 2017/0245862 A1 | 8/2017 | Cox et al. | |
| 2017/0252190 A1 | 9/2017 | Becking et al. | |
| 2017/0258473 A1 | 9/2017 | Plaza et al. | |
| 2017/0273692 A1 | 9/2017 | Choubey | |
| 2017/0281194 A1 | 10/2017 | Divino et al. | |
| 2017/0354402 A1 | 12/2017 | Lee et al. | |
| 2017/0354418 A1 | 12/2017 | Teoh et al. | |
| 2018/0000489 A1 | 1/2018 | Marchand et al. | |
| 2018/0036012 A1 | 2/2018 | Aboytes et al. | |
| 2018/0070955 A1 | 3/2018 | Greene et al. | |
| 2018/0125501 A1 | 5/2018 | Aboytes et al. | |
| 2018/0132859 A1 | 5/2018 | Aboytes et al. | |
| 2018/0132862 A1 | 5/2018 | Aboytes et al. | |
| 2018/0206849 A1 | 7/2018 | Hewitt et al. | |
| 2018/0250013 A1 | 9/2018 | Wallace et al. | |
| 2018/0263629 A1 | 9/2018 | Murphy et al. | |
| 2018/0271540 A1 | 9/2018 | Merritt et al. | |
| 2018/0303486 A1 | 10/2018 | Rosenbluth et al. | |
| 2019/0046209 A1 | 2/2019 | Plaza et al. | |
| 2019/0046210 A1 | 2/2019 | Bowman | |
| 2019/0053810 A1 | 2/2019 | Griffin | |
| 2019/0059907 A1 | 2/2019 | Rosqueta et al. | |
| 2019/0059909 A1 | 2/2019 | Griffin | |
| 2019/0069900 A1 | 3/2019 | Cam et al. | |
| 2019/0083075 A1 | 3/2019 | Onushko et al. | |
| 2019/0105054 A1 | 4/2019 | Aboytes et al. | |
| 2019/0105056 A1 | 4/2019 | Aboytes et al. | |
| 2019/0133794 A1 | 5/2019 | Kusleika | |
| 2019/0133795 A1 | 5/2019 | Choubey | |
| 2019/0150932 A1 | 5/2019 | Cruise et al. | |
| 2019/0167270 A1 | 6/2019 | Chen | |
| 2019/0167272 A1 | 6/2019 | Stephens et al. | |
| 2019/0192322 A1 | 6/2019 | Choubey et al. | |
| 2019/0201000 A1 | 7/2019 | Wallace et al. | |
| 2019/0201592 A1 | 7/2019 | Takahashi et al. | |
| 2019/0209146 A1 | 7/2019 | Hebert et al. | |
| 2019/0209178 A1 | 7/2019 | Richter et al. | |

(56) References Cited

U.S. PATENT DOCUMENTS

| | | |
|---|---|---|
| 2019/0209181 A1 | 7/2019 | Mayer et al. |
| 2019/0216467 A1 | 7/2019 | Goyal |
| 2019/0216468 A1 | 7/2019 | Larsen et al. |
| 2019/0223880 A1 | 7/2019 | Gerberding et al. |
| 2019/0223881 A1 | 7/2019 | Hewitt et al. |
| 2019/0223883 A1 | 7/2019 | Anderson et al. |
| 2019/0231328 A1 | 8/2019 | Hebert et al. |
| 2019/0239895 A1 | 8/2019 | Dawson et al. |
| 2019/0240049 A1 | 8/2019 | Dawson et al. |
| 2019/0240050 A1 | 8/2019 | Dawson et al. |
| 2019/0247053 A1 | 8/2019 | Inouye |
| 2019/0251866 A1 | 8/2019 | Babiker et al. |
| 2019/0254676 A1 | 8/2019 | Murphy et al. |
| 2019/0254691 A1 | 8/2019 | Martin et al. |
| 2019/0261967 A1 | 8/2019 | Hebert et al. |
| 2019/0262002 A1 | 8/2019 | Benjamin |
| 2019/0262119 A1 | 8/2019 | Gupta et al. |
| 2019/0262123 A1 | 8/2019 | Mangiardi |
| 2019/0269411 A1 | 9/2019 | Bardsley et al. |
| 2019/0269414 A1 | 9/2019 | Griffin |
| 2019/0269533 A1 | 9/2019 | Vong et al. |
| 2019/0269534 A1 | 9/2019 | Choubey |
| 2019/0274691 A1 | 9/2019 | Sepetka et al. |
| 2019/0282242 A1 | 9/2019 | Divino et al. |
| 2019/0290286 A1 | 9/2019 | Divino et al. |
| 2019/0298379 A1 | 10/2019 | Porter et al. |
| 2019/0298380 A1 | 10/2019 | Inouye et al. |
| 2019/0298387 A1 | 10/2019 | Qin et al. |
| 2019/0307460 A1 | 10/2019 | Ferrera et al. |
| 2019/0307546 A1 | 10/2019 | Aguilar et al. |

* cited by examiner

INTRASACCULAR ANEURYSM OCCLUSION DEVICE WITH NET OR MESH EXPANDED BY STRING-OF-PEARLS EMBOLIES

CROSS-REFERENCE TO RELATED APPLICATIONS

This present application claims the priority benefit of U.S. provisional patent No. 62/794,609 filed on 2019 Jan. 19. This application also claims the priority benefit of U.S. provisional patent No. 62/794,607 filed on 2019 Jan. 19. This application also is a continuation in part of U.S. patent application Ser. No. 16/541,241 filed on 2019 Aug. 15. This application also is a continuation in part of U.S. patent application Ser. No. 15/865,822 filed on 2018 Jan. 9. This application also is a continuation in part of U.S. patent application Ser. No. 15/861,482 filed on 2018 Jan. 3.

U.S. patent application Ser. No. 16/541,241 claimed the priority benefit of U.S. provisional patent No. 62/794,609 filed on 2019 Jan. 19. U.S. patent application Ser. No. 16/541,241 also claimed the priority benefit of U.S. provisional patent No. 62/794,607 filed on 2019 Jan. 19. U.S. patent application Ser. No. 16/541,241 also claimed the priority benefit of U.S. provisional patent No. 62/720,173 filed on 2018 Aug. 21. U.S. patent application Ser. No. 16/541,241 also was a continuation in part of U.S. patent application Ser. No. 15/865,822 filed on 2018 Jan. 9.

U.S. patent application Ser. No. 15/865,822 claimed the priority benefit of U.S. provisional patent No. 62/589,754 filed on 2017 Nov. 22. U.S. patent application Ser. No. 15/865,822 also claimed the priority benefit of U.S. provisional patent No. 62/472,519 filed on 2017 Mar. 16. U.S. patent application Ser. No. 15/865,822 also was a continuation in part of U.S. patent application Ser. No. 15/081,909 filed on 2016 Mar. 27. U.S. patent application Ser. No. 15/865,822 also was a continuation in part of U.S. patent application Ser. No. 14/526,600 filed on 2014 Oct. 29.

U.S. patent application Ser. No. 15/861,482 claimed the priority benefit of U.S. provisional patent No. 62/589,754 filed on 2017 Nov. 22. U.S. patent application Ser. No. 15/861,482 also claimed the priority benefit of U.S. provisional patent No. 62/472,519 filed on 2017 Mar. 16. U.S. patent application Ser. No. 15/861,482 also claimed the priority benefit of U.S. provisional patent No. 62/444,860 filed on 2017 Jan. 11. U.S. patent application Ser. No. 15/861,482 also was a continuation in part of U.S. patent application Ser. No. 15/080,915 filed on 2016 Mar. 25 which issued as U.S. patent Ser. No. 10/028,747 on 2018 Jul. 24. U.S. patent application Ser. No. 15/861,482 also was a continuation in part of U.S. patent application Ser. No. 14/526,600 filed on 2014 Oct. 29.

U.S. patent application Ser. No. 15/081,909 was a continuation in part of U.S. patent application Ser. No. 14/526,600 filed on 2014 Oct. 29. U.S. patent application Ser. No. 15/080,915 was a continuation in part of U.S. patent application Ser. No. 14/526,600 filed on 2014 Oct. 29. U.S. patent application Ser. No. 14/526,600 claimed the priority benefit of U.S. provisional patent No. 61/897,245 filed on 2013 Oct. 30. U.S. patent application Ser. No. 14/526,600 also was a continuation in part of U.S. patent application Ser. No. 12/989,048 filed on 2010 Oct. 21 which issued as U.S. Pat. No. 8,974,487 on 2015 Mar. 10. U.S. patent application Ser. No. 12/989,048 claimed the priority benefit of U.S. provisional patent No. 61/126,047 filed on May 1, 2008. U.S. patent application Ser. No. 12/989,048 also claimed the priority benefit of U.S. provisional patent No. 61/126,027 filed on 2008 May 1.

The entire contents of these related applications are incorporated herein by reference.

FEDERALLY SPONSORED RESEARCH

Not Applicable

SEQUENCE LISTING OR PROGRAM

Not Applicable

BACKGROUND—FIELD OF INVENTION

This invention relates to devices for occluding cerebral aneurysms.

Introduction

An aneurysm is an abnormal bulging of a blood vessel wall. The vessel from which the aneurysm protrudes is the parent vessel. Saccular aneurysms look like a sac protruding out from the parent vessel. Saccular aneurysms have a neck and can be prone to rupture. Fusiform aneurysms are a form of aneurysm in which a blood vessel is expanded circumferentially in all directions. Fusiform aneurysms generally do not have a neck and are less prone to rupturing than saccular aneurysms. As an aneurysm grows larger, its walls generally become thinner and weaker. This decrease in wall integrity, particularly for saccular aneurysms, increases the risk of the aneurysm rupturing and hemorrhaging blood into the surrounding tissue, with serious and potentially fatal health outcomes.

Cerebral aneurysms, also called brain aneurysms or intracranial aneurysms, are aneurysms that occur in the intercerebral arteries that supply blood to the brain. The majority of cerebral aneurysms form at the junction of arteries at the base of the brain that is known as the Circle of Willis where arteries come together and from which these arteries send branches to different areas of the brain. Although identification of intact aneurysms is increasing due to increased use of outpatient imaging such as outpatient MRI scanning, many cerebral aneurysms still remain undetected unless they rupture. If they do rupture, they often cause stroke, disability, and/or death. The prevalence of cerebral aneurysms is generally estimated to be in the range of 1%-5% of the general population or approximately 3-15 million people in the U.S. alone. Approximately 30,000 people per year suffer a ruptured cerebral aneurysm in the U.S. alone. Approximately one-third to one-half of people who suffer a ruptured cerebral aneurysm die within one month of the rupture. Sadly, even among those who survive, approximately one-half suffer significant and permanent deterioration of brain function. Better alternatives for cerebral aneurysm treatment are needed.

Review of the Relevant Art

There is considerable relevant art with respect to aneurysm occlusion devices. For example, U.S. Pat. No. 8,974,512 (Aboytes et al., Mar. 10, 2015, "Devices and Methods for the Treatment of Vascular Defects"), U.S. Pat. No. 8,998,947 (Aboytes et al., Apr. 7, 2015, "Devices and Methods for the Treatment of Vascular Defects"), and U.S. Pat. No. 9,844,382 (Aboytes et al., Dec. 19, 2017, "Devices and Methods for the Treatment of Vascular Defects"), and U.S. patent applications 20120239074 (Aboytes et al., Sep. 20, 2012, "Devices and Methods for the Treatment of Vascular Defects"), 20130116722 (Aboytes et al., May 9, 2013, "Devices and Methods for the Treatment of Vascular Defects"), 20150209050 (Aboytes et al., Jul. 30, 2015, "Devices and Methods for the Treatment of Vascular Defects"), 20150272590 (Aboytes et al., Oct. 1, 2015, "Devices and Methods for the Treatment of Vascular Defects"), 20150342613 (Aboytes et al., Dec. 3, 2015, "Devices and Methods for the Treatment of Vascular Defects"), 20160262766 (Aboytes et al., Sep. 15, 2016, "Devices and Methods for the Treatment of Vascular Defects"), 20180125501 (Aboytes et al., May 10, 2018, "Devices and Methods for the Treatment of Vascular Defects"), 20180132859 (Aboytes et al., May 17, 2018, "Devices and Methods for the Treatment of Vascular Defects"), 20180132862 (Aboytes et al., May 17, 2018, "Devices and Methods for the Treatment of Vascular Defects"), 20190105054 (Aboytes et al., Apr. 11, 2019, "Devices and Methods for the Treatment of Vascular Defects"), 20190105056 (Aboytes et al., Apr. 11, 2019, "Devices and Methods for the Treatment of Vascular Defects"), 20180036012 (Aboytes et al., Feb. 8, 2018, "Devices, Systems, and Methods for the Treatment of Vascular Defects"), 20190059907 (Rosqueta et al., Feb. 28, 2019, "Devices, Systems, and Methods for the Treatment of Vascular Defects"), and 20170281194 (Divino et al., Oct. 5, 2017, "Embolic Medical Devices") disclose intrasaccular ribbons for aneurysm occlusion.

Intrasaccular ribbons are innovative relative to conventional coiling, but can have limitations. For example, due to the somewhat random turning and winding of a ribbon within an aneurysm sac, it can be challenging for a user of a ribbon device to ensure that a wide portion of the ribbon actually winds up being across the aneurysm neck. Also, some ribbons tend to form a pre-determined (e.g. spherical) shape which does not conform to the sac contours of an irregularly-shaped aneurysm.

U.S. patent Ser. No. 10/433,853 (Divino et al., Oct. 8, 2019, "Embolic Medical Devices") discloses an intrasaccular ribbon for aneurysm occlusion with a pre-insertion rolled configuration. U.S. patent application 20190298387 (Qin et al., Oct. 3, 2019, "Aneurysm Treatment Coils") discloses an occlusion device with open loops and closed loops to provide balanced stiffness and flexibility. U.S. patent application 20170252190 (Becking et al., Sep. 7, 2017, "Braid Implant Delivery Systems") discloses neurovascular devices with low profile compressibility. U.S. patent application 20150196744 (Aboytes, Jul. 16, 2015, "Devices and Method for Vascular Recanalization") and U.S. Pat. No. 9,931,495 (Aboytes, Apr. 3, 2018, "Devices and Methods for Vascular Recanalization") disclose a device for restoring blood flow through an obstructed blood vessel.

U.S. patent application 20190254691 (Martin et al., Aug. 22, 2019, "Flexible Intravascular Treatment Devices and Associated Systems and Methods of Use") discloses stents with a plurality of cells and a plurality of joints between adjacent cells. U.S. patent application 20190133795 (Choubey, May 9, 2019, "Meshes, Devices and Methods for Treating Vascular Defects") discloses stents with a plurality of strut regions and a plurality of bridge regions. U.S. patent application 20190133794 (Kusleika, May 9, 2019, "Methods and Systems for Increasing a Density of a Region of a Vascular Device") discloses a stent with elastic members and differential porosity. U.S. patent Ser. No. 10/314,593 (Bardsley et al., Jun. 11, 2019, "Occlusive Devices") discloses dual-layer inverted meshes for vascular occlusion. U.S. patent Ser. No. 10/327,781 (Divino et al., Jun. 25, 2019, "Occlusive Devices") and U.S. patent application 20140135812 (Divino et al., May 15, 2014, "Occlusive Devices") disclose intrasaccular occlusion which are filled with liquid embolic material and expand to a pre-set shape.

U.S. patent applications 20170079661 (Bardsley et al., Mar. 23, 2017, "Occlusive Devices") and 20190269411 (Bardsley et al., Sep. 5, 2019, "Occlusive Devices") disclose dual-layer inverted meshes for vascular occlusion. U.S. patent applications 20190282242 (Divino et al., Sep. 19, 2019, "Occlusive Devices") and 20190290286 (Divino et al., Sep. 26, 2019, "Occlusive Devices") disclose intrasaccular occlusion devices which are filled with liquid embolic material and expand to a pre-set shape. U.S. patent applications 20190269534 (Choubey, Sep. 5, 2019, "Thin Film Mesh Hybrid for Treating Vascular Defects") and 20170273692 (Choubey, Sep. 28, 2017, "Thin Wall Constructions for Vascular Flow Diversion") disclose stents with strut regions extending circumferentially about the expandable device.

U.S. Pat. No. 9,393,022 (Becking et al., Jul. 19, 2016, "Two-Stage Deployment Aneurysm Embolization Devices") discloses embolic implants which are deployed in two stages. U.S. Pat. No. 9,157,174 (Kusleika, Oct. 13, 2015, "Vascular Device for Aneurysm Treatment and Providing Blood Flow into a Perforator Vessel") and U.S. Pat. No. 9,561,122 (Kusleika, Feb. 7, 2017, "Vascular Device for Aneurysm Treatment and Providing Blood Flow into a Perforator Vessel") disclose occlusion devices with heat-set strands. U.S. patent applications 20190239895 (Dawson et al., Aug. 8, 2019, "Vascular Expandable Devices") and 20190240049 (Dawson et al., Aug. 8, 2019, "Vascular Expandable Devices") disclose a device with a generally tubular sidewall formed by braided strands. U.S. patent application 20190192322 (Choubey et al., Jun. 27, 2019, "Vascular Flow Diversion") discloses a device with a plurality of connector sections extending circumferentially about the device. U.S. patent application 20190069900 (Cam et al., Mar. 7, 2019, "Vascular Remodeling Device") discloses a vascular remodeling device with a first section and a protruding section.

U.S. patent applications 20140330299 (Rosenbluth et al., Nov. 6, 2014, "Embolic Occlusion Device and Method"), 20130245667 (Marchand et al., Sep. 19, 2013, "Filamentary Devices and Treatment of Vascular Defects"), 20180206849 (Hewitt et al., Jul. 26, 2018, "Filamentary Devices for the Treatment of Vascular Defects"), 20170095254 (Hewitt et al., Apr. 6, 2017, "Filamentary Devices for Treatment of Vascular Defects"), 20180000489 (Marchand et al., Jan. 4, 2018, "Filamentary Devices for Treatment of Vascular Defects"), and 20140052233 (Cox et al., Feb. 20, 2014, "Methods and Devices for Treatment of Vascular Defects") disclose a self-expanding globular shell which is inserted into an aneurysm sac.

U.S. patent application 20180303486 (Rosenbluth et al., Oct. 25, 2018, "Embolic Occlusion Device and Method") discloses a self-expanding globular shell which is inserted into an aneurysm sac plus a coil which extends out from the distal end of the shell. U.S. patent application 20190223881 (Hewitt et al., Jul. 25, 2019, "Devices for Therapeutic Vascular Procedures") discloses a self-expanding globular shell which is inserted into an aneurysm sac, wherein some shell filaments extend beyond the distal end of the shell. U.S. Pat. No. 9,955,976 (Hewitt et al., May 1, 2018, "Filamentary Devices for Treatment of Vascular Defects") discloses a self-expanding intrasaccular globular shell with areas with different size pores. U.S. patent application 20160249934

(Hewitt et al., Sep. 1, 2016, "Filamentary Devices for Treatment of Vascular Defects") discloses occlusive meshes with variable mesh density.

U.S. patent application 20160045201 (Rosenbluth et al., Feb. 18, 2016, "Blood Flow Disruption Devices and Methods for the Treatment of Vascular Defects") discloses a blood flow disruption device with a porous inner flow disruption element and a porous outer flow disruption element which coaxially surrounds the inner flow disruption element. U.S. patent application 20190046209 (Plaza et al., Feb. 14, 2019, "Delivery and Detachment Systems and Methods for Vascular Implants") discloses a system for delivering an implant device to a vascular site. U.S. patent application 20160249935 (Hewitt et al., Sep. 1, 2016, "Devices for Therapeutic Vascular Procedures") discloses an expandable cylindrical structure made of wires with a self-expanding permeable shell at the distal end of the cylindrical structure. U.S. patent application 20160367260 (Hewitt et al., Dec. 22, 2016, "Devices for Therapeutic Vascular Procedures") discloses an expandable cylindrical structure made of wires and a self-expanding permeable shell at the distal end of the cylindrical structure. U.S. patent application 20170128077 (Hewitt et al., May 11, 2017, "Devices for Therapeutic Vascular Procedures") discloses methods and devices for removing a thrombus.

U.S. patent application 20120283768 (Cox et al., Nov. 8, 2012, "Method and Apparatus for the Treatment of Large and Giant Vascular Defects") discloses a plurality of self-expanding globular shells which are inserted into an aneurysm sac. U.S. patent application 20170245862 (Cox et al., Aug. 31, 2017, "Methods and Devices for Treatment of Vascular Defects") discloses a method for inserting a self-expanding globular shell into an aneurysm sac. U.S. patent application 20160249937 (Marchand et al., Sep. 1, 2016, "Multiple Layer Filamentary Devices for Treatment of Vascular Defects") discloses a self-expanding multi-layer shell which is inserted into an aneurysm sac. U.S. patent application 20180271540 (Merritt et al., Sep. 27, 2018, "Systems and Methods for Embolization of Body Structures") discloses a self-expanding shell with lobes which is inserted into an aneurysm sac. U.S. patent application 20170258473 (Plaza et al., Sep. 14, 2017, "Systems and Methods for Delivery of Stents and Stent-Like Devices") discloses a self-expanding tubular structure which is inserted into the parent vessel of an aneurysm. U.S. patent Ser. No. 10/398,441 (Warner et al., Sep. 3, 2019, "Vascular Occlusion") discloses an aneurysm occlusion system which includes a containment bag, a pusher, and a stopper ring. U.S. patent application 20190269533 (Vong et al., Sep. 5, 2019, "Stent and Stent Delivery Device") discloses a stent made from a single woven nitinol wire.

U.S. Pat. No. 6,350,270 (Roue, Feb. 26, 2002, "Aneurysm Liner") discloses an aneurysm liner with an extender inside the liner. U.S. Pat. No. 7,153,323 (Teoh et al., Dec. 26, 2006, "Aneurysm Liner with Multi-Segment Extender") discloses an aneurysm liner with extender segments inside the liner. U.S. patent application 20170354402 (Lee et al., Dec. 14, 2017, "Braided Medical Devices") discloses a vaso-occlusive member with helically-wound filaments. U.S. patent application 20190262119 (Gupta et al., Aug. 29, 2019, "Delivery Device for Use with an Embolic Material") discloses an embolic material delivery assembly with an outer member having a lumen extending therein, a distal end region, and an inner member disposed within the lumen of the outer member. U.S. Pat. No. 5,935,148 (Villar et al., Aug. 10, 1999, "Detachable, Varying Flexibility, Aneurysm Neck Bridge") and U.S. Pat. No. 6,063,104 (Villar et al., May 16, 2000, "Detachable, Varying Flexibility, Aneurysm Neck Bridge") disclose an aneurysm neck bridge with varying flexibility.

U.S. patent application 20180070955 (Greene et al., Mar. 15, 2018, "Embolic Containment") discloses systems to deliver liquid embolic material into an aneurysm. U.S. patent application 20190046210 (Bowman, Feb. 14, 2019, "Embolic Device with Shaped Wire") discloses using a helical carrier to occlude an aneurysm. U.S. patent application 20190150932 (Cruise et al., May 23, 2019, "Embolization Device Constructed from Expansile Polymer") discloses expandable polymer devices for aneurysm occlusion. U.S. Pat. No. 7,695,488 (Berenstein et al., Apr. 13, 2010, "Expandable Body Cavity Liner Device") discloses an aneurysm liner with areas with different elasticities. U.S. patent application 20030028209 (Teoh et al., Feb. 6, 2003, "Expandable Body Cavity Liner Device") discloses an aneurysm liner for treating aneurysms of various shapes and sizes. U.S. patent application 20040098027 (Teoh et al., May 20, 2004, "Expandable Body Cavity Liner Device") discloses various aneurysm treatment devices ranging from ball stents to permeable liners.

U.S. patent applications 20060155323 (Porter et al., Jul. 13, 2006, "Intra-Aneurysm Devices") and 20190298379 (Porter et al., Oct. 3, 2019, "Intra-Aneurysm Devices") disclose an aneurysm occlusion device with an upper member in the dome and a lower member in the aneurysm neck. U.S. Pat. No. 9,592,363 (Griffin et al., Mar. 14, 2017, "Medical Device") discloses a device with a shaft having an elongated inner member and an elongated tubular reinforcing member disposed over at least a portion of the inner member. U.S. patent application 20160213380 (O'Brien, et al., Jul. 28, 2016, "Occlusion Device Having Spherical Secondary Shape and Mandrel for Forming Same") discloses a sphere made from helical memory wire. U.S. patent application 20190274691 (Sepetka et al., Sep. 12, 2019, "Occlusive Device") discloses a tubular braid that folds inward on itself for aneurysm occlusion.

U.S. patent applications 20190216468 (Larsen et al., Jul. 18, 2019, "Occlusive Medical Device"), 20190247053 (Inouye, Aug. 15, 2019, "Occlusive Medical Device"), 20190223883 (Anderson et al., Jul. 25, 2019, "Occlusive Medical Device with Delivery System"), 20190298380 (Inouye et al., Oct. 3, 2019, "Occlusive Medical Device with Fixation Members"), and 20190083075 (Onushko et al., Mar. 21, 2019, "Occlusive Medical Device with Sealing Member") disclose a neck bridge to occlude a heart appendage.

U.S. Pat. No. 5,690,666 (Berenstein et al., Nov. 25, 1997, "Ultrasoft Embolism Coils and Process for Using Them") discloses ultrasoft embolism coils. U.S. patent application 20190240050 (Dawson et al., Aug. 8, 2019, "Vascular Expandable Devices") discloses a tubular structure made with a plurality of braided metallic elements. U.S. patent applications 20180263629 (Murphy et al., Sep. 20, 2018, "Vaso-Occlusive Device and Delivery Assembly") and 20190254676 (Murphy et al., Aug. 22, 2019, "Vaso-Occlusive Device and Delivery Assembly") disclose a vaso-occlusive treatment system with multi-layer wires. U.S. patent Ser. No. 10/426,486 (Guo et al., Oct. 1, 2019, "Vaso-Occlusive Device Delivery System") and U.S. patent application 20170354418 (Teoh et al., Dec. 14, 2017, "Vaso-Occlusive Device Delivery System") disclose a vaso-occlusive device delivery system with a heat-activated pusher.

U.S. patent applications 20170086851 (Wallace et al., Mar. 30, 2017, "Vaso-Occlusive Devices and Methods of Use") and 20190201000 (Wallace et al., Jul. 4, 2019, "Vaso- Occlusive Devices") disclose a vaso-occlusive delivery system with a pusher. U.S. patent Ser. No. 10/383,635 (Wallace et al., Aug. 20, 2019, "Vaso-Occlusive Devices and Methods of Use") and U.S. patent application 20180250013 (Wallace et al., Sep. 6, 2018, "Vaso-Occlusive Devices Including a Friction Element") disclose a vaso-occlusive system with a pusher to deliver soft embolic members. U.S. patent application 20190167270 (Chen, Jun. 6, 2019, "Vaso-Occlusive Devices with In-Situ Stiffening") discloses a vaso-occlusive device that is constructed out of dissimilar metallic materials which cause galvanic corrosion.

U.S. patent Ser. No. 10/130,372 (Griffin, Nov. 20, 2018, "Occlusion Device"), and U.S. patent applications 20150313605 (Griffin, Nov. 5, 2015, "Occlusion Device"), 20170156734 (Griffin, Jun. 8, 2017, "Occlusion Device"), 20190053810 (Griffin, Feb. 21, 2019, "Occlusion Device"), 20190059909 (Griffin, Feb. 28, 2019, "Occlusion Device") disclose an occlusive mesh with a circumferential fold line. U.S. patent application 20190269414 (Griffin, Sep. 5, 2019, "Occlusion Device") discloses an intrasaccular occlusion device with a plurality of coaxial expandable carriages.

U.S. patent application 20190209178 (Richter et al., Jul. 11, 2019, "Aneurysm Closure Device") discloses occlusion of an aneurysm neck using a device with a plurality of self-expanding arms. U.S. patent application 20030212419 (West, Nov. 13, 2003, "Aneurysm Embolization Device and Deployment System") discloses an aneurysm embolization device with a headpiece and a plurality of spherical members. U.S. patent application 20080281350 (Sepetka et al., Nov. 13, 2008, "Aneurysm Occlusion Devices") discloses an (hourglass-shaped) occlusive device with a biocompatible matrix. U.S. patent application 20060116709 (Sepetka et al., Jun. 1, 2006, "Aneurysm Treatment Devices and Methods") discloses a device which expands within an aneurysm sac.

U.S. patent application 20190216467 (Goyal, Jul. 18, 2019, "Apparatus and Methods for Intravascular Treatment of Aneurysms") discloses an aneurysm neck bridge deployed in the parent vessel of the aneurysm. U.S. Pat. No. 6,346,117 (Greenhalgh, Feb. 12, 2002, "Bag for Use in the Intravascular Treatment of Saccular Aneurysms") and U.S. Pat. No. 6,391,037 (Greenhalgh, May 21, 2002, "Bag for Use in the Intravascular Treatment of Saccular Aneurysms") disclose a plurality of resilient filamentary members braided into a tubular sleeve with an opening to receive a clotting medium such as a platinum wire. U.S. patent application 20090287294 (Rosqueta et al., Nov. 19, 2009, "Braid-Ball Embolic Devices") discloses "Goodness, Gracious, Great balls of wire!"

U.S. Pat. No. 4,341,218 (U, Jul. 27, 1982, "Detachable Balloon Catheter") discloses a balloon with a hollow cylinder fastened at the neck of the balloon. U.S. Pat. No. 4,364,392 (Strother et al., Dec. 21, 1982, "Detachable Balloon Catheter") discloses a balloon into which a carrier liquid is pumped. U.S. Pat. No. 6,511,468 (Cragg et al., Jan. 28, 2003, "Device and Method for Controlling Injection of Liquid Embolic Composition") discloses a system to deliver liquid embolic material into an aneurysm. U.S. patent application 20190262123 (Mangiardi, Aug. 29, 2019, "Device and Method for Management of Aneurism, Perforation and Other Vascular Abnormalities") discloses a method for treating perforations, fistulas, ruptures, dehiscence and aneurysms. U.S. patent application 20060052816 (Bates et al., Mar. 9, 2006, "Device for Treating an Aneurysm") discloses a patch that covers an aneurysm neck.

U.S. Pat. No. 6,585,748 (Jeffree, Jul. 1, 2003, "Device for Treating Aneurysms") discloses a permeable intrasaccular bag into which embolic coils are inserted. U.S. patent application 20190251866 (Babiker et al., Aug. 15, 2019, "Device Specific Finite Element Models for Simulating Endovascular Treatment") discloses using finite element medical device models and computational fluid dynamics for aneurysm treatment. U.S. patent application 20090318948 (Linder et al., Dec. 24, 2009, "Device, System and Method for Aneurysm Embolization") discloses dispensing embolic elements freely and randomly within an aneurysm cavity. U.S. patent application 20190201592 (Takahashi et al., Jul. 4, 2019, "Devices and Methods for Aneurysm Treatment") discloses ways to reduce susceptibility artifacts in MRA images.

U.S. Pat. No. 8,597,320 (Sepetka et al., Dec. 3, 2013, "Devices and Methods for Treating Vascular Malformations") discloses an occlusive device with a proximal collar and a distal collar. U.S. patent application 20020169473 (Sepetka et al., Nov. 14, 2002, "Devices and Methods for Treating Vascular Malformations") discloses occlusive devices with a primary coil and secondary windings. U.S. patent Ser. No. 10/426,487 (Bachman et al., Oct. 1, 2019, "Devices, Systems and Methods for Enclosing an Anatomical Opening") discloses a device with a distal-facing portion which occludes an aneurysm and a proximal-facing portion which arches over lumina of an artery. U.S. patent application 20150216684 (Enzmann et al., Aug. 6, 2015, "Dual Rotational Stent Apparatus and Method for Endovascular Treatment of Aneurysms") discloses a coaxial stent system for aneurysm treatment.

U.S. Pat. No. 6,530,934 (Jacobsen et al., Mar. 11, 2003, "Embolic Device Composed of a Linear Sequence of Miniature Beads") discloses an embolic device comprising a sequence of flexibly interconnected miniature beads. U.S. patent application 20190307546 (Aguilar et al., Oct. 10, 2019, "Embolic Device with Improved Neck Coverage") discloses a helical intrasaccular device. U.S. patent application 20040010263 (Boucher et al., Jan. 15, 2004, "Expandable Preformed Structures for Deployment in Interior Body Regions") discloses using a stylet to straighten an expandable structure during deployment into an interior body region. U.S. patent Ser. No. 10/405,966 (Johnson, Sep. 10, 2019, "Implantable Intraluminal Device") discloses intraluminal stent graft devices whose walls include compliant channels which allow for fluid communication.

U.S. patent application 20190167272 (Stephens et al., Jun. 6, 2019, "Inflatable Implant") discloses an implant with a low profile when introduced into the body and a larger profile when it is inflated with one or more filler materials. U.S. patent Ser. No. 10/420,862 (Sharma et al., Sep. 24, 2019, "In-Situ Forming Foams for Treatment of Aneurysms") and U.S. patent application 20120265287 (Sharma et al., Oct. 18, 2012, "In-Situ Forming Foams for Treatment of Aneurysms") disclose the use of in-situ forming polymer foams to treat aneurysms. U.S. patent application 20190307460 (Ferrera et al., Oct. 10, 2019, "Intrasacular Occlusion Devices Methods Processes and Systems") discloses flexible aneurysm embolization devices made from laser cut nitinol. U.S. patent application 20090112249 (Miles et al., Apr. 30, 2009, "Medical Device for Modification of Left Atrial Appendage and Related Systems and Methods") discloses collapsible and self-expanding devices to modify a left atrial appendage.

U.S. patent application 20190209181 (Mayer et al., Jul. 11, 2019, "Medical Device for Treating Vascular Malformations") discloses a helical device with a coilable section and a docking section. U.S. patent application 20050142163 (Hunter et al., Jun. 30, 2005, "Medical Implants and Fibrosis-Inducing Agents") discloses implants with fibrosis-inducing agents. U.S. patent application 20110184451 (Sahl, Jul. 28, 2011, "Membrane Implant for Treatment of Cerebral Artery Aneurysms") discloses a cylindrical biocompatible plastic membrane used in combination with a stent. U.S. Pat. No. 7,083,643 (Whalen et al., Aug. 1, 2006, "Methods for Treating Aneurysms") discloses filling an aneurysm sac with a fluid composition which solidifies in situ.

U.S. patent applications 20190209146 (Hebert et al., Jul. 11, 2019, "Micrograft for the Treatment of Intracranial Aneurysms and Method for Use"), 20190231328 (Hebert et al., Aug. 1, 2019, "Micrograft for the Treatment of Intracranial Aneurysms and Method for Use"), and 20190261967 (Hebert et al., Aug. 29, 2019, "Micrograft for the Treatment of Intracranial Aneurysms and Method for Use") disclose a micrograft with a series of peaks and valleys formed by crimping. U.S. patent Ser. No. 10/406,010 (Bourang, Sep. 10, 2019, "Multi-Stent and Multi-Balloon Apparatus for Treating Bifurcations and Methods of Use") discloses using two catheters and three stents to treat a bifurcated vessel. U.S. patent application 20190262002 (Benjamin, Aug. 29, 2019, "Novel Enhanced Orb-Like Intrasacular Device") discloses an orb-shaped device with zones of flexure and open cells.

U.S. patent application 20150005807 (Lagodzki et al., Jan. 1, 2015, "Occlusion Device Including Bundle of Occlusion Wires Having Preformed Shapes") discloses an occlusion device with shape memory wires which expand to a preformed shape. U.S. patent Ser. No. 10/342,548 (Duncan, Jul. 9, 2019, "Occlusion Devices and Methods of Their Manufacture and Use") discloses a device with a lateral fringe on membranous material. U.S. patent Ser. No. 10/383,749 (Zhou et al., Aug. 20, 2019, "Stent and Method of Inserting a Stent into a Delivery Catheter") discloses a stent which is radially contractable from a fully radially expanded state to a radially contracted state via elongation of the frame. U.S. patent application 20110196413 (Wallace et al., Aug. 11, 2011, "System and Method for Retaining Vaso-Occlusive Devices within an Aneurysm") discloses an occlusive mesh made from a shape-memory alloy. U.S. patent application 20190223880 (Gerberding et al., Jul. 25, 2019, "Systems and Methods for Supporting or Occluding a Physiological Opening or Cavity") discloses a device with a distal-facing portion which occludes an aneurysm and a proximal-facing portion which arches over lumina of an artery. U.S. Pat. No. 5,334,210 (Gianturco, Aug. 2, 1994, "Vascular Occlusion Assembly") discloses an occlusion bag with an expanded diamond shape and an elongated flexible filler member.

U.S. patent application 20060167494 (Suddaby, Jul. 27, 2006, "Aneurysm Repair Method and Apparatus") discloses disks pressing against inner and outer sides of an aneurysm neck. U.S. patent application 20020026217 (Baker et al., Feb. 28, 2002, "Apparatus and Method for Repair of Perigraft Flow") discloses a device for causing thrombus between a graft and an aneurysm wall. U.S. patent application 20010034531 (Ho et al., Oct. 25, 2001, "Bioactive Three Loop Coil") discloses an occlusion subassembly comprising a base section and a lateral protrusion fixedly attached to the base section. U.S. Pat. No. 6,855,153 (Saadat, Feb. 15, 2005, "Embolic Balloon") and U.S. patent application 20020165572 (Saadat, Nov. 7, 2002, "Embolic Balloon") disclose an embolic balloon which aspirates blood while expanding.

U.S. patent application 20020026210 (Abdel-Gawwad, Feb. 28, 2002, "Endovascular Aneurysm Treatment Device and Method") discloses using an intrasacular frame and suction to collapse an aneurysm. U.S. patent application 20040254625 (Stephens et al., Dec. 16, 2004, "Inflatable Implant") discloses an implant that is inflated with filler materials. U.S. patent application 20060149309 (Paul et al., Jul. 6, 2006, "Inverting Occlusion Devices, Methods, and Systems") discloses inverted vascular occlusion devices. U.S. Pat. No. 4,638,803 (Rand, Jan. 27, 1987, "Medical Apparatus for Inducing Scar Tissue Formation in a Body") discloses a balloon coated with thrombosis-inducing material. U.S. Pat. No. 6,958,061 (Truckai et al., Oct. 25, 2005, "Microspheres with Sacrificial Coatings for Vaso-Occlusive Systems") discloses using a fluid to deliver microspheres for vascular occlusion. U.S. Pat. No. 5,041,090 (Scheglov et al., Aug. 20, 1991, "Occluding Device") discloses using nested balloons for occlusion.

SUMMARY OF THE INVENTION

This invention is an intrasaccular aneurysm occlusion device comprising: a net or mesh with a self-expanding resilient proximal portion (which is deployed close to the aneurysm neck) and an expandable flexible distal portion (which is deployed close to the aneurysm dome); and a "string of pearls" of embolic members which are inserted into the net or mesh. The "string of pearls" embolic members are interconnected by one or more longitudinal strands. The proximal portion of the net or mesh at least partially self-expands to cover the aneurysm neck. The flexible distal portion or the net or mesh is expanded in the dome of the aneurysm sac by the insertion, retention, and accumulation of the "string of pearls" embolic members in the net or mesh.

The resilient proximal portion of the net or mesh expands to a width which is wider than the aneurysm neck and covers the aneurysm neck from inside the aneurysm sac, thereby reducing (or completely blocking) blood flow into the aneurysm sac. The flexible distal portion of the net or mesh conforms to the contours of even irregularly-shaped aneurysms, thereby helping to hold the device within an aneurysm sac and further helping to reduce (or completely block) blood flow into the aneurysm sac. The embolic members fill a high percentage of the aneurysm sac volume, further helping to reduce (or completely block) blood flow into the aneurysm sac. The embolic members are larger than openings in the net or mesh so that the embolic members do not escape after they have been inserted into the net or mesh. The longitudinal strands interconnect the embolic members, which further helps to keep the embolic members from escaping out through the net or mesh.

BRIEF INTRODUCTION TO THE FIGURES

DETAILED DESCRIPTION OF THE FIGURES

Figure 1:
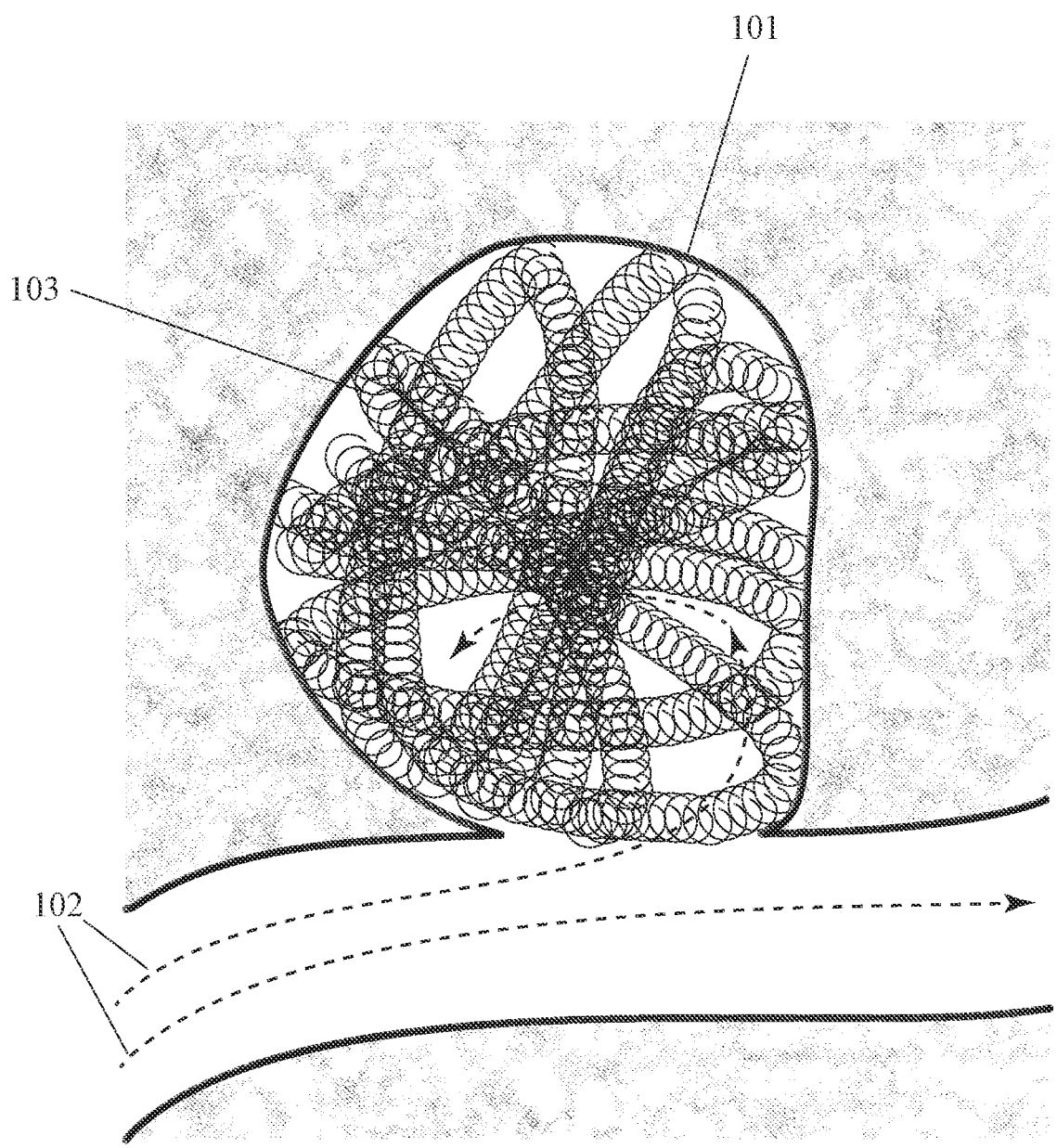
FIG. 1 shows an example of prior art comprising coils.

FIG. 1 shows an example of prior art comprising coils 103 which are inserted into an aneurysm sac 101 to occlude the aneurysm. Coiling has been a tremendous innovation in the intravascular treatment of cerebral aneurysms. However, depending on the morphology of the aneurysm sac and the various twists and turns which coils take within the aneurysm sac, blood flow 102 through the parent vessel the aneurysm can continue to flow into and within the aneurysm sac. When this happens, the aneurysm can continue to grow or even rupture. Also, coils can sometimes protrude out of the aneurysm sac into the parent vessel.

Figure 2:
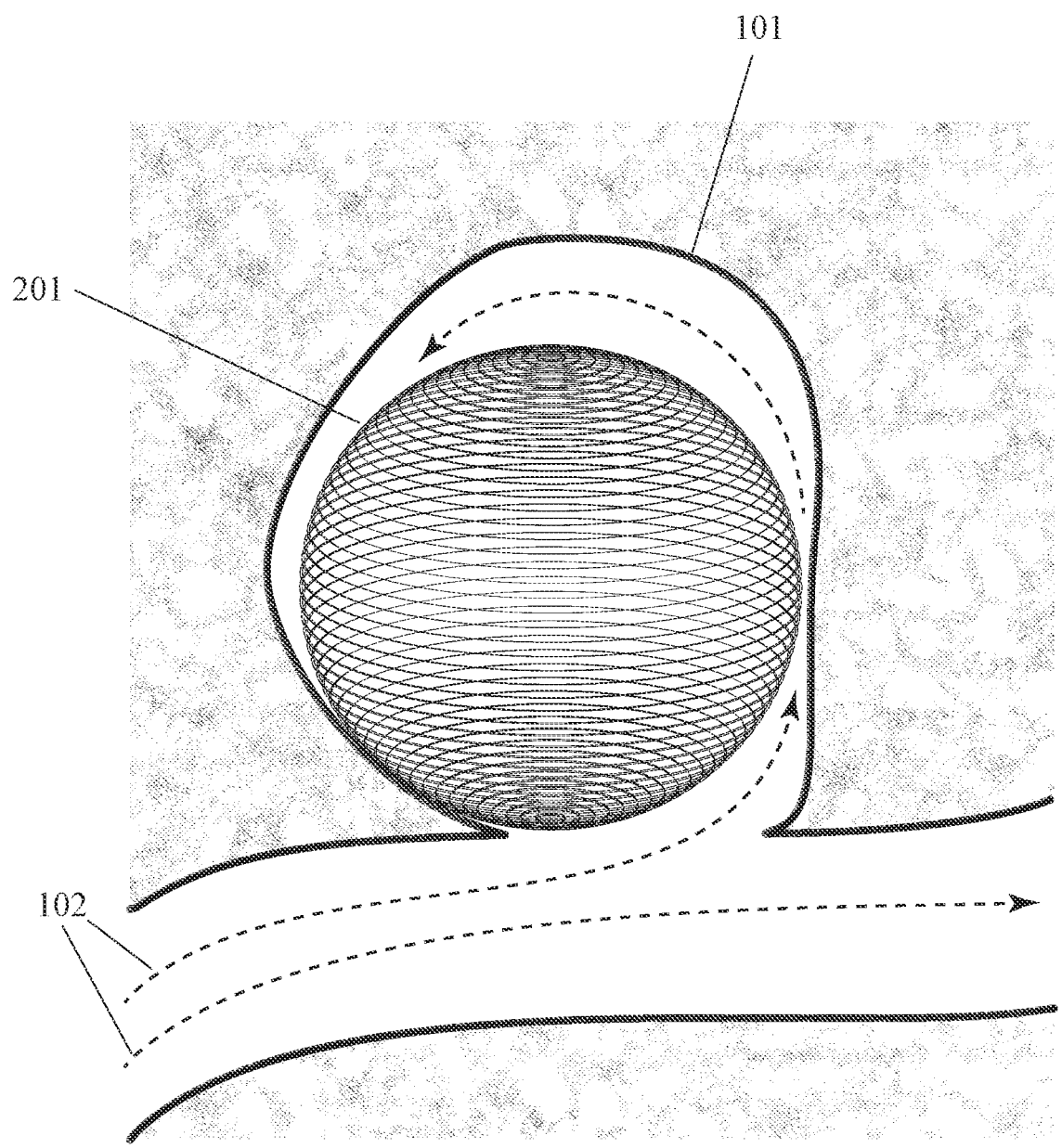
FIG. 2 shows an example of prior art comprising a mesh which self-expands to a pre-determined shape.

FIG. 2 shows an example of prior art comprising a resilient mesh device 201 which self-expands to a predetermined (e.g. spherical) shape within aneurysm sac 101. This can satisfactorily occlude aneurysms with the same shape as the pre-determined expanded shape of the device. However, such devices may not satisfactorily occlude aneurysms with a sac shape (such as the irregular shape shown here) which is different than the pre-determined shape of the device. In this case, blood flow 102 through the parent vessel the aneurysm can flow around the device into and within the aneurysm sac. When this happens, the aneurysm can continue to grow or even rupture.

Figure 3:
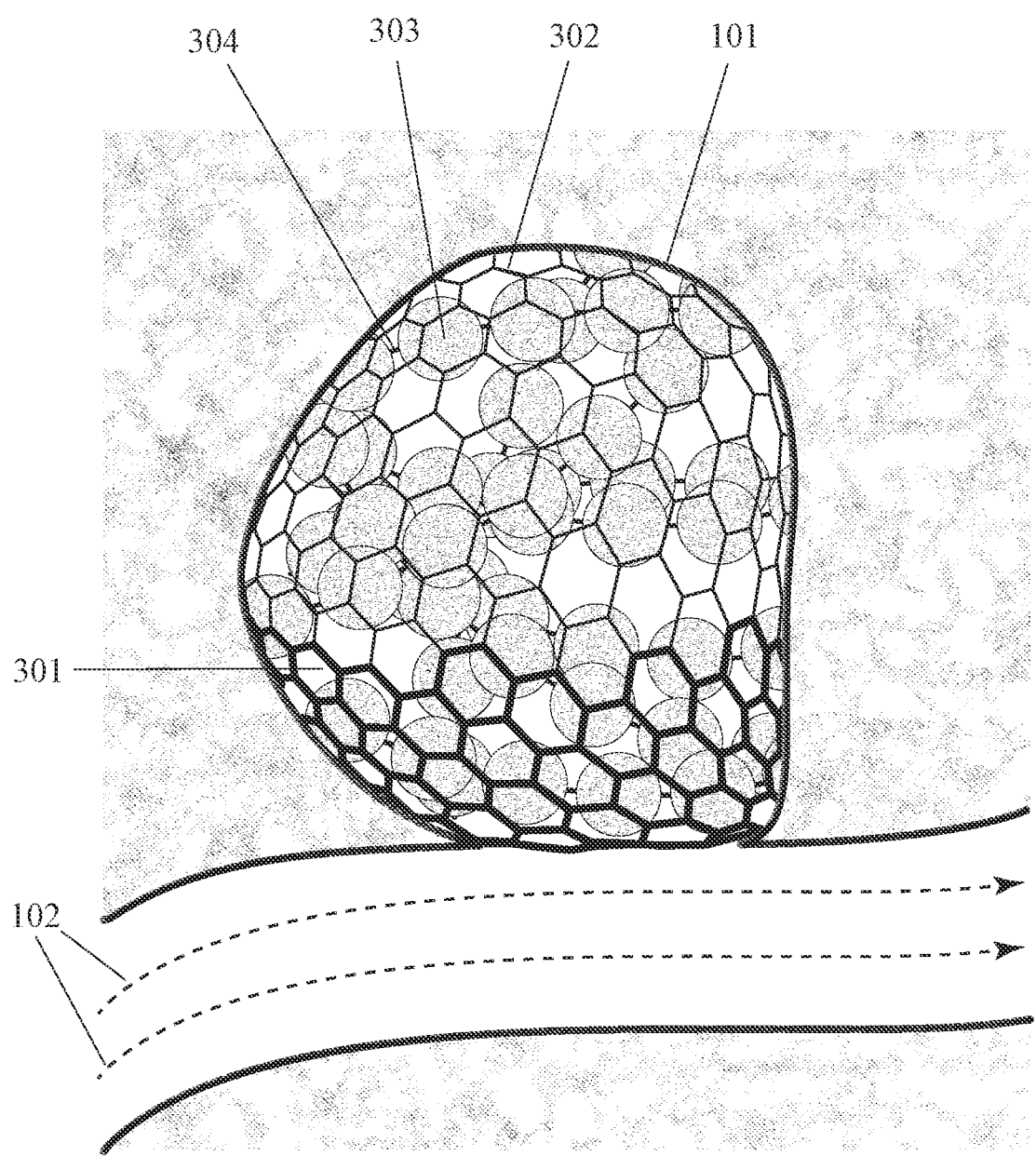
FIG. 3 shows an embodiment of this invention with a two-portion intrasaccular net or mesh which has been expanded by the insertion, retention, and accumulation of a string-of-pearls of embolic members in the net or mesh.

FIG. 3 shows an embodiment of the intrasaccular aneurysm occlusion device disclosed herein which addresses the limitations of the prior art shown in FIGS. 1 and 2. The flexible intrasaccular aneurysm occlusion device shown in FIG. 3 has been expanded by the insertion of "string of pearls" embolic members to conform to the irregular shape of aneurysm sac 101 so that blood flow through the parent vessel stops going into the aneurysm sac and the device is frictionally secured to the walls of the aneurysm sac (to reduce the possibility of protrusion into the parent vessel).

Specifically, FIG. 3 shows an embodiment of an intrasaccular aneurysm occlusion device comprising: (a) an expandable net or mesh (including portions 301 and 302) which is inserted into an aneurysm sac 101; wherein a proximal portion 301 of the expandable net or mesh is configured to be a first (average) distance from the aneurysm neck after the net or mesh has been inserted into the aneurysm sac; wherein a distal portion 302 of the expandable net or mesh is configured to be a second (average) distance from the aneurysm neck after the net or mesh has been inserted into the aneurysm sac; wherein the second (average) distance is greater than the first (average) distance; wherein the proximal portion of the expandable net or mesh has a first level of flexibility, elasticity, conformability, and/or compliance; wherein the distal portion of the expandable net or mesh has a second level of flexibility, elasticity, conformability, and/or compliance; and wherein second level of flexibility, elasticity, conformability, and/or compliance is greater than the first level of flexibility, elasticity, conformability, and/or compliance; (b) a plurality of three-dimensional embolic members (including 303) which are inserted into and retained within the expandable net or mesh after the net or mesh has been inserted into the aneurysm sac; and (c) one or more longitudinal strands (including 304) which are inserted into the aneurysm sac, wherein the one or more longitudinal strands connect embolic members in the plurality of three-dimensional embolic members to each other. Embodiment variations discussed elsewhere in this disclosure and priority-linked disclosures can also be applied to this example.

In an example, an intrasaccular aneurysm occlusion device can comprise: an expandable net or mesh which is inserted into an aneurysm sac; wherein a proximal portion of the expandable net or mesh is configured to be a first (average) distance from the aneurysm neck after the net or mesh has been inserted into the aneurysm sac; wherein a distal portion of the expandable net or mesh is configured to be a second (average) distance from the aneurysm neck after the net or mesh has been inserted into the aneurysm sac; wherein the second (average) distance is greater than the first (average) distance; wherein the proximal portion of the expandable net or mesh has a first level of flexibility, elasticity, conformability, and/or compliance; wherein the distal portion of the expandable net or mesh has a second level of flexibility, elasticity, conformability, and/or compliance; and wherein second level of flexibility, elasticity, conformability, and/or compliance is greater than the first level of flexibility, elasticity, conformability, and/or compliance; a plurality of three-dimensional embolic members which are inserted into and retained within the expandable net or mesh after the net or mesh has been inserted into the aneurysm sac; and one or more longitudinal strands which are inserted into the aneurysm sac, wherein the one or more longitudinal strands connect embolic members in the plurality of three-dimensional embolic members to each other.

In an example, a proximal portion of a net or mesh can self expand within the aneurysm sac. In an example, a distal portion of a net or mesh can be expanded by the insertion, retention, and accumulation of embolic members inside the net or mesh within the aneurysm sac. In an example, a proximal portion of a net or mesh can self expand after the net or mesh has been inserted into the aneurysm sac, but the distal portion of the net or mesh is (primarily) expanded by the insertion, retention, and accumulation of embolic members inside the net or mesh after the net or mesh has been inserted into the aneurysm sac.

In an example, a distal portion of a net or mesh can have a first radial size while being delivered to an aneurysm through a catheter, can self expand to a second radial size within the aneurysm sac, and can further expand to a third radial size within the aneurysm sac due to the insertion, retention, and accumulation of embolic members into the net or mesh—wherein the second radial size is at least 10% greater than the first radial size and wherein the third radial size is at least 10% greater than the second radial size. In an example, a distal portion of a net or mesh can have a first radial size while being delivered to an aneurysm through a catheter, can self expand to a second radial size within the aneurysm sac, and can further expand to a third radial size within the aneurysm sac by the insertion, retention, and accumulation of embolic members into the net or mesh—wherein the second radial size is at least 20% greater than the first radial size and wherein the third radial size is at least 50% greater than the second radial size.

In an example, a net or mesh can have a first configuration while it is being delivered to an aneurysm through a catheter and can expand to a second configuration within the aneurysm sac. In an example, a net or mesh can have a compressed configuration while it is being delivered to an aneurysm through a catheter and can have an expanded configuration within the aneurysm sac. In an example, a net or mesh can have a compressed configuration while it is being delivered to an aneurysm through a catheter and can expand to an expanded configuration within the aneurysm sac. In an example, a net or mesh can have a radially-constrained configuration while it is being delivered to an aneurysm through a catheter and can transform to a radially-expanded configuration within the aneurysm sac. In an example, a net or mesh can have a radially-constrained and longitudinally-expanded configuration while it is being delivered to an aneurysm through a catheter and can transform to a radially-expanded and longitudinally-constrained configuration within the aneurysm sac.

In an example, a proximal portion of a net or mesh can have a first configuration while it is being delivered to an aneurysm through a catheter and can expand to a second configuration within the aneurysm sac. In an example, a proximal portion of a net or mesh can have a compressed configuration while it is being delivered to an aneurysm through a catheter and can have an expanded configuration within the aneurysm sac. In an example, a proximal portion of a net or mesh can have a compressed configuration while it is being delivered to an aneurysm through a catheter and can expand to an expanded configuration within the aneurysm sac. In an example, a proximal portion of a net or mesh can have a radially-constrained configuration while it is being delivered to an aneurysm through a catheter and can transform to a radially-expanded configuration within the aneurysm sac. In an example, a proximal portion of a net or mesh can have a radially-constrained and longitudinally-expanded configuration while it is being delivered to an aneurysm through a catheter and can transform to a radially-expanded and longitudinally-constrained configuration within the aneurysm sac.

In an example, a proximal portion of an aneurysm occlusion device can have a first configuration while it is being delivered to an aneurysm through a catheter and can expand to a second configuration within the aneurysm sac. In an example, a proximal portion of an aneurysm occlusion device can have a compressed configuration while it is being delivered to an aneurysm through a catheter and can have an expanded configuration within the aneurysm sac. In an example, a proximal portion of an aneurysm occlusion device can have a compressed configuration while it is being delivered to an aneurysm through a catheter and can expand to an expanded configuration within the aneurysm sac. In an example, a proximal portion of an aneurysm occlusion device can have a radially-constrained configuration while it is being delivered to an aneurysm through a catheter and can transform to a radially-expanded configuration within the aneurysm sac. In an example, a proximal portion of an aneurysm occlusion device can have a radially-constrained and longitudinally-expanded configuration while it is being delivered to an aneurysm through a catheter and can transform to a radially-expanded and longitudinally-constrained configuration within the aneurysm sac.

In an example, a net or mesh can have a constrained configuration while it is being delivered to an aneurysm through a catheter and can expand to a relaxed configuration within the aneurysm sac. In an example, a net or mesh can have a radially-constrained configuration while it is being delivered to an aneurysm through a catheter and can expand to a radially-relaxed configuration within the aneurysm sac. In an example, a net or mesh can have a first configuration with a longitudinal axis and a radial axis while it is being delivered to an aneurysm through a catheter and can expand to a second configuration within the aneurysm sac, wherein the longitudinal axis of the net or mesh is decreased in the second configuration (relative to first configuration) and the radial axis of the net or mesh is increased in the second configuration (relative to the first configuration).

In an example, a proximal portion of a net or mesh can have a constrained configuration while it is being delivered to an aneurysm through a catheter and can expand to a relaxed configuration within the aneurysm sac. In an example, a proximal portion of a net or mesh can have a radially-constrained configuration while it is being delivered to an aneurysm through a catheter and can expand to a radially-relaxed configuration within the aneurysm sac. In an example, a proximal portion of a net or mesh can have a first configuration with a longitudinal axis and a radial axis while it is being delivered to an aneurysm through a catheter and can expand to a second configuration within the aneurysm sac, wherein the longitudinal axis of the net or mesh is decreased in the second configuration (relative to first configuration) and the radial axis of the net or mesh is increased in the second configuration (relative to the first configuration).

In an example, a proximal portion of an aneurysm occlusion device can have a constrained configuration while it is being delivered to an aneurysm through a catheter and can expand to a relaxed configuration within the aneurysm sac. In an example, a proximal portion of an aneurysm occlusion device can have a radially-constrained configuration while it is being delivered to an aneurysm through a catheter and can expand to a radially-relaxed configuration within the aneurysm sac. In an example, a proximal portion of an aneurysm occlusion device can have a first configuration with a longitudinal axis and a radial axis while it is being delivered to an aneurysm through a catheter and can expand to a second configuration within the aneurysm sac, wherein the longitudinal axis of the resilient portion of the device is decreased in the second configuration (relative to first configuration) and the radial axis of the resilient portion of the device is increased in the second configuration (relative to the first configuration).

In an example, a net or mesh can be compressed to form a dual-layer net or mesh within an aneurysm sac. In an example, a net or mesh can be positioned to overlap itself to form a dual-layer net or mesh within an aneurysm sac. In an example, a net or mesh can be inverted or everted to form a dual-layer net or mesh within an aneurysm sac. In an example, a portion of a net or mesh can be compressed to form a dual-layer portion of the net or mesh within an aneurysm sac. In an example, a portion of a net or mesh can be positioned to overlap itself to form a dual-layer portion of the net or mesh within an aneurysm sac. In an example, a portion of a net or mesh can be inverted or everted to form a dual-layer portion of the net or mesh within an aneurysm sac. In an example, a proximal portion of a net or mesh can be compressed to form a dual-layer net or mesh within an aneurysm sac. In an example, a proximal portion of a net or mesh can be positioned to overlap itself to form a dual-layer net or mesh within an aneurysm sac. In an example, a proximal portion of a net or mesh can be inverted or everted to form a dual-layer net or mesh within an aneurysm sac.

In an example, a net or mesh can be compressed to form a dual-layer net or mesh prior to delivery to an aneurysm sac. In an example, a net or mesh can be positioned to overlap itself to form a dual-layer net or mesh prior to delivery to an aneurysm sac. In an example, a net or mesh can be inverted or everted to form a dual-layer net or mesh prior to delivery to an aneurysm sac. In an example, a portion of a net or mesh can be compressed to form a dual-layer portion of the net or mesh prior to delivery to an aneurysm sac. In an example, a portion of a net or mesh can be positioned to overlap itself to form a dual-layer portion of the net or mesh prior to delivery to an aneurysm sac. In an example, a portion of a net or mesh can be inverted or everted to form a dual-layer portion of the net or mesh prior to delivery to an aneurysm sac. In an example, a proximal portion of a net or mesh can be compressed to form a dual-layer net or mesh prior to delivery to an aneurysm sac. In an example, a proximal portion of a net or mesh can be positioned to overlap itself to form a dual-layer net or mesh prior to delivery to an aneurysm sac. In an example, a proximal portion of a net or mesh can be inverted or everted to form a dual-layer net or mesh prior to delivery to an aneurysm sac.

In an example, a net or mesh can self-expand and/or self-transition from a first configuration to a second configuration within an aneurysm sac. In an example, a net or mesh can be expanded and/or transitioned from a first configuration to a second configuration within an aneurysm sac by inflation of a balloon. In an example, a net or mesh can be expanded and/or transitioned from a first configuration to a second configuration within an aneurysm sac by a user pulling a wire, string, or other longitudinal member. In an example, a net or mesh can be expanded and/or transitioned from a first configuration to a second configuration within an aneurysm sac by a user pushing a wire or other longitudinal member. In an example, a net or mesh can be expanded and/or transitioned from a first configuration to a second configuration within an aneurysm sac by the application of thermal energy. In an example, a net or mesh can be expanded and/or transitioned from a first configuration to a second configuration within an aneurysm sac by the application of magnetic force.

In an example, a proximal portion of a net or mesh can self-expand and/or self-transition from a first configuration to a second configuration within an aneurysm sac. In an example, a proximal portion of a net or mesh can be expanded and/or transitioned from a first configuration to a second configuration within an aneurysm sac by inflation of a balloon. In an example, a proximal portion of a net or mesh can be expanded and/or transitioned from a first configuration to a second configuration within an aneurysm sac by a user pulling a wire, string, or other longitudinal member. In an example, a proximal portion of a net or mesh can be expanded and/or transitioned from a first configuration to a second configuration within an aneurysm sac by a user pushing a wire or other longitudinal member. In an example, a proximal portion of a net or mesh can be expanded and/or transitioned from a first configuration to a second configuration within an aneurysm sac by the application of thermal energy. In an example, a proximal portion of a net or mesh can be expanded and/or transitioned from a first configuration to a second configuration within an aneurysm sac by the application of magnetic force.

In an example, a proximal portion of a net or mesh can be in a first state while it is being delivered to an aneurysm through a catheter and can expand to a second state within the aneurysm sac. In an example, a proximal portion of a net or mesh can be in a compressed state while it is being delivered to an aneurysm through a catheter and can be in an expanded state within the aneurysm sac. In an example, a proximal portion of a net or mesh can be in a compressed state while it is being delivered to an aneurysm through a catheter and can expand to an expanded state within the aneurysm sac. In an example, a proximal portion of a net or mesh can be in a radially-constrained state while it is being delivered to an aneurysm through a catheter and can transform to a radially-expanded state within the aneurysm sac. In an example, a proximal portion of a net or mesh can be in a radially-constrained and longitudinally-expanded state while it is being delivered to an aneurysm through a catheter and can transform to a radially-expanded and longitudinally-constrained state within the aneurysm sac.

In an example, a proximal portion of a net or mesh can be in a constrained state while it is being delivered to an aneurysm through a catheter and can expand to a relaxed state within the aneurysm sac. In an example, a proximal portion of a net or mesh can be in a radially-constrained state while it is being delivered to an aneurysm through a catheter and can expand to a radially-relaxed state within the aneurysm sac. In an example, a proximal portion of a net or mesh can be in a first state with a longitudinal axis and a radial axis while it is being delivered to an aneurysm through a catheter and can change to a second state within the aneurysm sac, wherein the longitudinal axis of the resilient portion of the device is decreased in the second state (relative to first state) and the radial axis of the resilient portion of the device is increased in the second state (relative to the first configuration).

In an example, a proximal portion of an aneurysm occlusion device can be in a first state while it is being delivered to an aneurysm through a catheter and can expand to a second state within the aneurysm sac. In an example, a proximal portion of an aneurysm occlusion device can be in a compressed state while it is being delivered to an aneurysm through a catheter and can be in an expanded state within the aneurysm sac. In an example, a proximal portion of an aneurysm occlusion device can be in a compressed state while it is being delivered to an aneurysm through a catheter and can expand to an expanded state within the aneurysm sac. In an example, a proximal portion of an aneurysm occlusion device can be in a radially-constrained state while it is being delivered to an aneurysm through a catheter and can transform to a radially-expanded state within the aneurysm sac. In an example, a proximal portion of an aneurysm occlusion device can be in a radially-constrained and longitudinally-expanded state while it is being delivered to an aneurysm through a catheter and can transform to a radially-expanded and longitudinally-constrained state within the aneurysm sac.

In an example, a proximal portion of an aneurysm occlusion device can be in a constrained state while it is being delivered to an aneurysm through a catheter and can expand to a relaxed state within the aneurysm sac. In an example, a proximal portion of an aneurysm occlusion device can be in a radially-constrained state while it is being delivered to an aneurysm through a catheter and can expand to a radially-relaxed state within the aneurysm sac. In an example, a proximal portion of an aneurysm occlusion device can be in a first state with a longitudinal axis and a radial axis while it is being delivered to an aneurysm through a catheter and can change to a second state within the aneurysm sac, wherein the longitudinal axis of the resilient portion of the device is decreased in the second state (relative to first state) and the radial axis of the resilient portion of the device is increased in the second state (relative to the first configuration).

In an example, a proximal portion of a net or mesh can expand within an aneurysm sac into an upwardly-open concave shape and/or downwardly-pointing convex shape. In an example, a proximal portion of a net or mesh can expand within an aneurysm sac into a bowl, hemispherical, contact lens, paraboloid, or inverted umbrella shape which spans the interior of the aneurysm neck. In an example, a proximal portion of a net or mesh can expand within an aneurysm sac into a bowl, hemispherical, contact lens, paraboloid, or inverted umbrella shape with a diameter which is greater than the diameter of the aneurysm neck. In an example, a proximal portion of a net or mesh can expand within an aneurysm sac into a bowl, hemispherical, contact lens, paraboloid, or inverted umbrella shape with a diameter which is at least 80% of the largest diameter of the aneurysm sac.

In an example, a proximal portion of a net or mesh can expand within an aneurysm sac into a spherical, prolate spheroidal, ellipsoidal, or ovaloidal shape. In an example, a proximal portion of a net or mesh can expand within an aneurysm sac into a spherical, prolate spheroidal, ellipsoidal, or ovaloidal shape which spans the interior of the aneurysm neck. In an example, a proximal portion of a net or mesh can expand within an aneurysm sac into a spherical, prolate spheroidal, ellipsoidal, or ovaloidal shape with a diameter which is at least 80% of the largest diameter of the aneurysm sac parallel to the plane of the aneurysm neck. In an example, a proximal portion of a net or mesh can expand within an aneurysm sac into a spherical, prolate spheroidal, ellipsoidal, or ovaloidal shape and then be transformed (e.g. compressed) into a bowl, hemispherical, contact lens, paraboloid, or inverted umbrella shape. In an example, a proximal portion of a net or mesh can expand within an aneurysm sac into a spherical, prolate spheroidal, ellipsoidal, or ovaloidal shape and then be transformed (e.g. compressed) into a bowl, hemispherical, contact lens, paraboloid, or inverted umbrella shape by a user pulling (or pushing) a distal portion of the spherical, prolate spheroidal, ellipsoidal, or ovaloidal shape in a proximal direction.

In an example, a proximal portion of a net or mesh can expand within an aneurysm sac into a disk or pancake shape. In an example, a proximal portion of a net or mesh can expand within an aneurysm sac into an hourglass shape with a disk or pancake shaped portion inside the aneurysm sac and a disk or pancake portion inside the parent vessel of the aneurysm. In an example, a proximal portion of a net or mesh can expand within an aneurysm sac into a toroidal, ring, or cylindrical shape.

In an example, a proximal portion of a net or mesh can expand within an aneurysm sac into a lotus blossom or other radial-flower-petals shape. In an example, a proximal portion of a net or mesh can expand within an aneurysm sac into a lotus blossom or other radial-flower-petals shape with at least four radial petals inside the aneurysm sac. In an example, a proximal portion of a net or mesh can expand within an aneurysm sac into a lotus blossom or other radial-flower-petals shape with a plurality of radial petals inside the aneurysm sac and a plurality of radial petals in the parent vessel of the aneurysm. In an example, a proximal portion of a net or mesh can expand within an aneurysm sac into a lotus blossom or other radial-flower-petals shape with a plurality of radial petals on the inner surface of the aneurysm neck and a plurality of radial petals on the outer surface of the aneurysm neck.

In an example, a net or mesh can be in a first state while it is being delivered to an aneurysm through a catheter and can expand to a second state within the aneurysm sac. In an example, a net or mesh can be in a compressed state while it is being delivered to an aneurysm through a catheter and can be in an expanded state within the aneurysm sac. In an example, a net or mesh can be in a compressed state while it is being delivered to an aneurysm through a catheter and can expand to an expanded state within the aneurysm sac. In an example, a net or mesh can be in a radially-constrained state while it is being delivered to an aneurysm through a catheter and can transform to a radially-expanded state within the aneurysm sac. In an example, a net or mesh can be in a radially-constrained and longitudinally-expanded state while it is being delivered to an aneurysm through a catheter and can transform to a radially-expanded and longitudinally-constrained state within the aneurysm sac.

In an example, an intrasaccular aneurysm occlusion device can have a shape which is selected from the group consisting of: apple-shaped, barrel-shaped, bulbous, convex, ellipsoidal, globular, oblate spheroid, ovaloid, prolate-spheroid-shaped, spherical, and truncated-sphere-shaped. In an example, an intrasaccular aneurysm occlusion device can have a shape which is selected from the group consisting of: bowl-shaped, concave, hemispherical, and paraboloid of revolution. In an example, an intrasaccular aneurysm occlusion device can have a shape which is selected from the group consisting of: cubic, hexagon-shaped, hexahedron, octagon-shaped, octahedron, pentagonal-shaped, polyhedron-shaped, pyramidal, rectangular, square, and tetrahedronal.

In an example, a net or mesh can be in a constrained state while it is being delivered to an aneurysm through a catheter and can expand to a relaxed state within the aneurysm sac. In an example, a net or mesh can be in a radially-constrained state while it is being delivered to an aneurysm through a catheter and can expand to a radially-relaxed state within the aneurysm sac. In an example, a net or mesh can be in a first state with a longitudinal axis and a radial axis while it is being delivered to an aneurysm through a catheter and can change to a second state within the aneurysm sac, wherein the longitudinal axis of the net or mesh is decreased in the second state (relative to first state) and the radial axis of the net or mesh is increased in the second state (relative to the first state).

In an example, a net or mesh can be folded during delivery to an aneurysm and can unfold within an aneurysm sac by the accumulation of embolic members inserted into the net or mesh. In an example, a net or mesh can be inverted during delivery to an aneurysm and can be everted within an aneurysm sac by the accumulation of embolic members inserted into the net or mesh. In an example, a net or mesh can be rolled around itself during delivery to an aneurysm and unrolled within an aneurysm sac by the accumulation of embolic members inserted into the net or mesh. In an example, a net or mesh can be coiled around itself during delivery to an aneurysm and uncoiled within an aneurysm sac by the accumulation of embolic members inserted into the net or mesh. In an example, a net or mesh can overlap itself during delivery to an aneurysm and be expanded to a non-overlapping state within an aneurysm sac by the accumulation of embolic members inserted into the net or mesh. In an example, a net or mesh can be radially constrained by one or more circumferential bands during delivery to an aneurysm and can be released from these radial constraints within an aneurysm sac.

In an example, a portion of a net or mesh can be folded during delivery to an aneurysm and can unfold within an aneurysm sac by the accumulation of embolic members inserted into the net or mesh. In an example, a portion of a net or mesh can be inverted during delivery to an aneurysm and can be everted within an aneurysm sac by the accumulation of embolic members inserted into the net or mesh. In an example, a portion of a net or mesh can be rolled around itself during delivery to an aneurysm and unrolled within an aneurysm sac by the accumulation of embolic members inserted into the net or mesh. In an example, a portion of a net or mesh can be coiled around itself during delivery to an aneurysm and uncoiled within an aneurysm sac by the accumulation of embolic members inserted into the net or mesh. In an example, a portion of a net or mesh can overlap itself during delivery to an aneurysm and be expanded to a non-overlapping state within an aneurysm sac by the accumulation of embolic members inserted into the net or mesh. In an example, a portion of a net or mesh can be radially constrained by one or more circumferential bands during delivery to an aneurysm and can be released from these radial constraints within an aneurysm sac.

In an example, an intrasaccular aneurysm occlusion device can be folded during delivery to an aneurysm and can unfold within an aneurysm sac by the accumulation of embolic members inserted into the net or mesh. In an example, an intrasaccular aneurysm occlusion device can be inverted during delivery to an aneurysm and can be everted within an aneurysm sac by the accumulation of embolic members inserted into the net or mesh. In an example, an intrasaccular aneurysm occlusion device can be rolled around itself during delivery to an aneurysm and unrolled within an aneurysm sac by the accumulation of embolic members inserted into the net or mesh. In an example, an intrasaccular aneurysm occlusion device can be coiled around itself during delivery to an aneurysm and uncoiled within an aneurysm sac by the accumulation of embolic members inserted into the net or mesh. In an example, an intrasaccular aneurysm occlusion device can overlap itself during delivery to an aneurysm and be expanded to a non-overlapping state within an aneurysm sac by the accumulation of embolic members inserted into the net or mesh. In an example, an intrasaccular aneurysm occlusion device can be radially constrained by one or more circumferential bands during delivery to an aneurysm and can be released from these radial constraints within an aneurysm sac.

In an example, a proximal portion of a net or mesh can have a shape which is selected from the group consisting of: apple-shaped, barrel-shaped, bulbous, convex, ellipsoidal, globular, oblate spheroid, ovaloid, prolate-spheroid-shaped, spherical, and truncated-sphere-shaped. In an example, a proximal portion of a net or mesh can have a shape which is selected from the group consisting of: bowl-shaped, concave, hemispherical, and paraboloid of revolution. In an example, a proximal portion of a net or mesh can have a shape which is selected from the group consisting of: cubic, hexagon-shaped, hexahedron, octagon-shaped, octahedron, pentagonal-shaped, polyhedron-shaped, pyramidal, rectangular, square, and tetrahedronal.

In an example, an intrasaccular aneurysm occlusion device can have a shape which is selected from the group consisting of: circular, cylindrical, ring-shaped, and toroidal. In an example, an intrasaccular aneurysm occlusion device can have a shape which is selected from the group consisting of: conical, conic-section-shaped, tapered, and telescoping. In an example, an intrasaccular aneurysm occlusion device can have a shape which is selected from the group consisting of: disk-shaped, heart-shaped, helical, multi-planar, non-spherical surface of revolution, noodle-shaped, pancake-shaped, peanut-shaped, pear-shaped, semi-circular, and sinusoidal. In an example, an intrasaccular aneurysm occlusion device can have a shape which is selected from the group consisting of: clover-shaped, flower-petal-shaped, hub-and-spokes-shaped, multi-lobed, shape with radially-extending-protrusions, and star-shaped.

In an example, a proximal portion of a net or mesh can have a shape which is selected from the group consisting of: circular, cylindrical, ring-shaped, and toroidal. In an example, a proximal portion of a net or mesh can have a shape which is selected from the group consisting of: conical, conic-section-shaped, tapered, and telescoping. In an example, a proximal portion of a net or mesh can have a shape which is selected from the group consisting of: disk-shaped, heart-shaped, helical, multi-planar, non-spherical surface of revolution, noodle-shaped, pancake-shaped, peanut-shaped, pear-shaped, semi-circular, and sinusoidal. In an example, a proximal portion of a net or mesh can have a shape which is selected from the group consisting of: clover-shaped, flower-petal-shaped, hub-and-spokes-shaped, multi-lobed, shape with radially-extending-protrusions, and star-shaped.

In an example, at least a portion of a net or mesh for insertion into an aneurysm sac can be made from one or more materials selected from the group consisting of: nitinol (or other nickel titanium alloy), cobalt-chrome alloy (cobalt chromium), gold, palladium, platinum, steel (e.g. stainless steel), tantalum, titanium, and tungsten. In an example, at least a portion of a net or mesh for insertion into an aneurysm sac can be made from one or more materials selected from the group consisting of: polycarbonate urethane (PCU), polydimethylsiloxane (PDMS), polyesters, polyether block amide (PEBA), polyetherether ketone (PEEK), polyethylene, polyethylene glycol (PEG), polyethylene terephthalate (PET), polyglycolic acid (PGA), polylactic acid (PLA), poly-N-acetylglucosamine (PNAG), polyolefin, polyoleandlena, polypropylene, polytetrafluoroethylene (PTFE), polyurethane (PU), polywanacrakor, polyvinyl alcohol (PVA), and polyvinyl pyrrolidone (PVP).

In an example, a self-expanding proximal portion of a net or mesh can be made with a combination of materials including a first percentage of metal(s) and the distal portion of the net or mesh (which is passively expanded by the insertion and accumulation of embolic members into it) can be made with a second combination of materials including a second percentage of metal(s), wherein the second percentage is less than the first percentage. In an example, a self-expanding proximal portion of a net or mesh can be made with a combination of materials including a first percentage of polymer(s) and the distal portion of the net or mesh (which is passively expanded by the insertion and accumulation of embolic members into it) can be made with a second combination of materials including a second percentage of polymer(s), wherein the second percentage is greater than the first percentage. In an example, a self-expanding proximal portion of a net or mesh can be made primarily (or entirely) from one or more metals and the distal portion of the net or mesh (which is passively expanded by the insertion and accumulation of embolic members into it) can be made primarily (or entirely) from one or more polymers.

In an example, a self-expanding proximal portion of a net or mesh can be made with nitinol (or other nickel titanium alloy), cobalt-chrome alloy (cobalt chromium), gold, palladium, platinum, steel (e.g. stainless steel), tantalum, titanium, and/or tungsten. In an example, a flexible distal portion of a net or mesh can be made from one or more materials selected from the group consisting of: polycarbonate urethane (PCU), polydimethylsiloxane (PDMS), polyesters, polyether block amide (PEBA), polyetherether ketone (PEEK), polyethylene, polyethylene glycol (PEG), polyethylene terephthalate (PET), polyglycolic acid (PGA), polylactic acid (PLA), poly-N-acetylglucosamine (PNAG), polyolefin, polyoleandlena, polypropylene, polytetrafluoroethylene (PTFE), polyurethane (PU), polywanacrakor, polyvinyl alcohol (PVA), and polyvinyl pyrrolidone (PVP).

In an example, a self-expanding proximal portion of a net or mesh can be made with a first material and the distal portion of the net or mesh which is passively expanded by the insertion, retention, and accumulation of embolic members within it can be made with a second material. In an example, a self-expanding proximal portion of a net or mesh can be made with a first combination of materials and the distal portion of the net or mesh (which is passively expanded by the insertion and accumulation of embolic members into it) can be made with a second combination of materials.

In an example, at least a portion of a net or mesh for insertion into an aneurysm sac can be made from acrylic, nylon, and/or silk. In an example, at least a portion of a net or mesh for insertion into an aneurysm sac can be made from collagen, fibrin, fibronogen, fibronectin, gelatin, hydrogel, methylcellulose, and/or small intestinal submucosa. In an example, at least a portion of a net or mesh for insertion into an aneurysm sac can be made from, alginate, copolymer, ethylene vinyl alcohol (EVA), latex, radiopaque material, silicone, suneelium, thermoplastic elastomer, and/or water-soluble synthetic polymer.

In an example, a net or mesh which is inserted into an aneurysm sac can have a structure which is selected from the group consisting of: braided or woven shell, braided or woven structure, braided or woven tubular structure with inverted end portions, braided or woven tubular structure with tied ends, braided textile sphere, braided wire sphere, dual-layer braided or woven structure, hollow braided or woven structure, spherical braided or woven structure, and tubular braided or woven structure. In an example, a net or mesh which is inserted into an aneurysm sac can have a structure which is selected from the group consisting of: 3D-printed convex net or mesh, flexible metal mesh or net, metal hexagonal mesh or net, and polymer hexagonal mesh or net.

In an example, a net or mesh which is inserted into an aneurysm sac can have a structure which is selected from the group consisting of: containment bag, dual-layer body, flexible aneurysm liner, hollow framing structure, hollow shell structure, and thin-wall flexible metal sphere with holes. In an example, a net or mesh which is inserted into an aneurysm sac can be a balloon with holes. In an example, a net or mesh which is inserted into an aneurysm sac can be a cellular lattice or a hollow array of biological cells.

In an example, a proximal portion of a net or mesh which is inserted into an aneurysm sac can have a structure which is selected from the group consisting of: braided or woven shell, braided or woven structure, braided or woven tubular structure with inverted end portions, braided or woven tubular structure with tied ends, braided textile sphere, braided wire sphere, dual-layer braided or woven structure, hollow braided or woven structure, spherical braided or woven structure, and tubular braided or woven structure.

In an example, a proximal portion of a net or mesh which is inserted into an aneurysm sac can have a structure which is selected from the group consisting of: 3D-printed convex proximal portion of a net or mesh, flexible metal mesh or net, metal hexagonal mesh or net, and polymer hexagonal mesh or net. In an example, a proximal portion of a net or mesh which is inserted into an aneurysm sac can have a structure which is selected from the group consisting of: containment bag, dual-layer body, flexible aneurysm liner, hollow framing structure, hollow shell structure, and thin-wall flexible metal sphere with holes. In an example, a proximal portion of a net or mesh which is inserted into an aneurysm sac can be a balloon with holes. In an example, a proximal portion of a net or mesh which is inserted into an aneurysm sac can be a cellular lattice or a hollow array of biological cells.

In an example, a net or mesh for insertion into an aneurysm sac can be 3D printed. In an example, a flexible metal net or mesh can be made by 3D printing with beads or drops of liquid metal. In an example, a flexible polymer net or mesh can be made by 3D printing with beads or drops of a polymer material. In an example, a flexible polymer net or mesh can be made by 3D printing using an elastomeric polymer. In an example, a flexible polymer net or mesh can be made by 3D printing using a silicone-based polymer. In an example, a flexible polymer net or mesh can be made by 3D printing using polydimethylsiloxane (PDMS).

In an example, a generally globular or spherical net or mesh can be made using 3D printing. In an example, a flexible metal generally globular or spherical net or mesh can be made by 3D printing with metal. In an example, a flexible generally-globular polymer net or mesh can be made by 3D printing with a polymer. In an example, a flexible generally-globular polymer net or mesh can be made by 3D printing with an elastomeric polymer. In an example, a flexible generally-globular polymer net or mesh can be made by 3D printing with a silicone-based polymer. In an example, a flexible generally-globular polymer net or mesh can be made by 3D printing with polydimethylsiloxane (PDMS).

In an example, a convex hollow net or mesh can be made using 3D printing. In an example, a metal convex hollow net or mesh can be made by 3D printing with liquid metal. In an example, an elastic convex hollow polymer net or mesh can be made by 3D printing with a polymer material. In an example, an elastic convex hollow polymer net or mesh can be made by 3D printing with an elastomeric polymer. In an example, an elastic convex hollow polymer net or mesh can be made by 3D printing with a silicone-based polymer. In an example, an elastic convex hollow polymer net or mesh can be made by 3D printing with polydimethylsiloxane (PDMS).

In an example, a net or mesh with hexagonal openings (e.g. pores) can be made using 3D printing. In an example, a flexible metal net or mesh with hexagonal openings (e.g. pores) can be made by 3D printing with liquid metal. In an example, a net or mesh with hexagonal openings (e.g. pores) can be made by 3D printing with a polymer. In an example, a net or mesh with hexagonal openings (e.g. pores) can be made by 3D printing with an elastomeric polymer. In an example, a net or mesh with hexagonal openings (e.g. pores) can be made by 3D printing with a silicone-based polymer. In an example, a net or mesh with hexagonal openings (e.g. pores) can be made by 3D printing with polydimethylsiloxane (PDMS).

In an example, a net or mesh with quadrilateral openings (e.g. pores) can be made using 3D printing. In an example, a flexible metal net or mesh with quadrilateral openings (e.g. pores) can be made by 3D printing with liquid metal. In an example, a net or mesh with quadrilateral openings (e.g. pores) can be made by 3D printing with a polymer. In an example, a net or mesh with quadrilateral openings (e.g. pores) can be made by 3D printing with an elastomeric polymer. In an example, a net or mesh with quadrilateral openings (e.g. pores) can be made by 3D printing with a silicone-based polymer. In an example, a net or mesh with quadrilateral openings (e.g. pores) can be made by 3D printing with polydimethylsiloxane (PDMS).

In an example, a net or mesh with circular openings (e.g. pores) can be made using 3D printing. In an example, a flexible metal net or mesh with circular openings (e.g. pores) can be made by 3D printing with liquid metal. In an example, a net or mesh with circular openings (e.g. pores) can be made by 3D printing with a polymer. In an example, a net or mesh with circular openings (e.g. pores) can be made by 3D printing with an elastomeric polymer. In an example, a net or mesh with circular openings (e.g. pores) can be made by 3D printing with a silicone-based polymer. In an example, a net or mesh with circular openings (e.g. pores) can be made by 3D printing with polydimethylsiloxane (PDMS).

In an example, a net or mesh can be made by 3D printing material onto a form or mandrel. In an example, a flexible metal net or mesh can be made by 3D printing beads or drops of liquid metal onto a form or mandrel. In an example, a flexible metal net or mesh can be made by 3D printing beads or drops of a liquid polymer material onto a form or mandrel. In an example, a net or mesh can be made using 3D printing, creating a three-dimensional hollow shape by accumulating beads or drops of a polymer material. In an example, a net or mesh can be made using 3D printing, creating a three-dimensional hollow shape by accumulating beads or drops of two or more types of polymer. In an example, a net or mesh can be made using 3D printing, creating a three-dimensional hollow shape by accumulating beads or drops of two or more types of polymer, wherein one of the polymer types is dissolved after printing to form an inner cavity.

In an example, a generally-spherical net or mesh can be by 3D printing material onto a form or mandrel. In an example, a flexible metal net or mesh can be made by 3D printing liquid metal onto a generally-spherical form or mandrel. In an example, a flexible metal net or mesh can be made by 3D printing liquid polymer material onto a form or mandrel. In an example, a generally-spherical net or mesh can be made using 3D printing, creating a three-dimensional hollow shape by accumulating beads of liquid polymer. In an example, a generally-spherical net or mesh can be made using 3D printing, creating a three-dimensional hollow shape by accumulating beads of two or more types of polymer. In an example, a generally-spherical net or mesh can be made using 3D printing, creating a three-dimensional hollow shape by accumulating beads of two or more types of polymer, wherein one type of polymer is dissolved after printing to form an inner cavity.

In an example, a convex arcuate net or mesh can be made using 3D printing and a form or mandrel. In an example, a flexible metal net or mesh can be made by 3D printing liquid metal onto a form or mandrel. In an example, a flexible metal net or mesh can be made by 3D printing liquid polymer material onto a form or mandrel. In an example, a convex arcuate net or mesh can be made using 3D printing, creating a three-dimensional hollow shape by accumulating beads of liquid polymer. In an example, a convex arcuate net or mesh can be made using 3D printing, creating a three-dimensional hollow shape by accumulating beads of two or more types of polymer. In an example, a convex arcuate net or mesh can be made using 3D printing, creating a three-dimensional hollow shape by accumulating beads of two or more types of polymer, wherein one type of polymer is dissolved after printing to form an inner cavity. In an example, a net or mesh can be 3D printed around a polymer core which is dissolved after printing to create a hollow convex net or mesh.

In an example, a net or mesh can be made using 3D printing, wherein a first material is used to print a proximal portion of the net or mesh and a second material is used to print a distal portion of the net or mesh. In an example, a net or mesh can be made using 3D printing, wherein a first polymer is used to print a proximal portion of the net or mesh and a second polymer is used to print a distal portion of the net or mesh. In an example, a net or mesh can be made using 3D printing, wherein a first polymer with a first durometer is used to print a proximal portion of the net or mesh and a second polymer with a second durometer is used to print a distal portion of the net or mesh, wherein the second durometer is less than the first durometer. In an example, a net or mesh can be made using 3D printing, wherein a proximal portion of the net or mesh is printed with a first mesh density and a distal portion of the net or mesh is printed with a second mesh density, wherein the second density is less than the first density.

In an example, a net or mesh with multiple layers can be 3D printed. In an example, a first layer of the net or mesh can be printed using a first material and a second layer of the net or mesh can be printed using a second material. In an example, a first layer of the net or mesh can be printed with a first mesh density and a second layer of the net or mesh can be printed with a second mesh density. In an example, an outer polymer mesh layer can be printed onto an inner metal mesh layer. In an example, an outer mesh layer can be printed on only a proximal portion of an inner mesh layer so as to create lower mesh density and/or greater radial mesh strength on a proximal portion of a net or mesh. In an example, a folded net or mesh can be 3D printed in a compressed form which can be expanded later, after the net or mesh has been inserted into an aneurysm sac.

In an example, a convex hollow net or mesh can be made by dispensing lines or streams of liquid material onto a central form or mandrel, wherein the liquid material subsequently solidifies (to at least some extent) to form the net or mesh. In an example, a convex hollow metal net or mesh can be made by dispensing lines or streams of metal in liquid form onto a central form or mandrel, wherein the liquid material subsequently solidifies (to at least some extent) to form the net or mesh. In an example, a convex hollow metal net or mesh can be made by dispensing lines or streams of a polymer material in liquid form onto a central form or mandrel, wherein the liquid material subsequently solidifies (to at least some extent) to form the net or mesh. In an example, a convex hollow metal net or mesh can be made by dispensing intersecting (e.g. orthogonal) lines or streams of metal in liquid form onto a central form or mandrel, wherein the liquid material subsequently solidifies (to at least some extent) to form the net or mesh. In an example, a convex hollow metal net or mesh can be made by dispensing intersecting (e.g. orthogonal) lines or streams of a polymer material in liquid form onto a central form or mandrel, wherein the liquid material subsequently solidifies (to at least some extent) to form the net or mesh.

In an example, a net or mesh for insertion into an aneurysm sac can be made by 3D printing cells into a convex hollow structure. In an example, a net or mesh for insertion into an aneurysm sac can be made by 3D printing cells into a convex hollow lattice. In an example, a net or mesh for insertion into an aneurysm sac can be made by 3D printing tissue or other biological material into a convex hollow structure. In an example, a net or mesh for insertion into an aneurysm sac can be made by 3D printing tissue or other biological material into a convex hollow lattice.

In an example, an aneurysm occlusion device which is inserted into an aneurysm sac can have a structure which is selected from the group consisting of: braided or woven shell, braided or woven structure, braided or woven tubular structure with inverted end portions, braided or woven tubular structure with tied ends, braided textile sphere, braided wire sphere, dual-layer braided or woven structure, hollow braided or woven structure, spherical braided or woven structure, and tubular braided or woven structure. In an example, an aneurysm occlusion device which is inserted into an aneurysm sac can have a structure which is selected from the group consisting of: 3D-printed convex aneurysm occlusion device, flexible metal mesh or net, metal hexagonal mesh or net, and polymer hexagonal mesh or net.

In an example, an aneurysm occlusion device which is inserted into an aneurysm sac can have a structure which is selected from the group consisting of: containment bag, dual-layer body, flexible aneurysm liner, hollow framing structure, hollow shell structure, and thin-wall flexible metal sphere with holes. In an example, an aneurysm occlusion device which is inserted into an aneurysm sac can be a balloon with holes. In an example, an aneurysm occlusion device which is inserted into an aneurysm sac can be a cellular lattice or a hollow array of biological cells.

In an example, at least a portion of a net or mesh for insertion into an aneurysm sac can be a braided or woven braided structure; braided or woven braided sphere; braided or woven braided tube whose ends have been tied close; braided or woven braided tube whose ends have been twisted close; braided or woven braided tube whose ends have been inverted; structure with multiple braided or woven layers; structure with distal and proximal braided or woven portions; or structure made from braided or woven filaments, wires, or tubes. In an example, a proximal portion of a device can be a braided or woven braided structure; braided or woven braided sphere; braided or woven braided tube whose ends have been tied close; braided or woven braided tube whose ends have been twisted close; braided or woven braided tube whose ends have been inverted; structure with multiple braided or woven layers; structure with distal and proximal braided or woven portions; or structure made from braided or woven filaments, wires, or tubes.

In an example, at least a portion of a net or mesh for insertion into an aneurysm sac can be made from elongate filaments which are attached to each other by welding or soldering. In an example, at least a portion of a net or mesh for insertion into an aneurysm sac can be made from elongate filaments which are attached to each other by epoxy bonding or other adhesion. In an example, at least a portion of a net or mesh for insertion into an aneurysm sac can be made from elongate filaments which are attached to each other by tying or crimping. In an example, at least a portion of a net or mesh for insertion into an aneurysm sac can be made from elongate filaments with different diameters. In an example, at least a portion of a net or mesh for insertion into an aneurysm sac can be made from elongate filaments comprising different materials. In an example, at least a portion of a net or mesh for insertion into an aneurysm sac can be made from a combination of metal and polymer filaments.

In an example, a proximal portion of a net or mesh can be made with wires, tubes, fibers, strands, or yarns with a first thickness and the distal portion of the net or mesh (which is passively expanded by the insertion and accumulation of embolic members into it) can be made with wires, tubes, fibers, strands, or yarns with a second thickness, wherein the second thickness is less than the first thickness. In an example, a proximal portion of a net or mesh can be made with a first braid or weave of wires, tubes, fibers, strands, or yarns and the distal portion of the net or mesh (which is passively expanded by the insertion and accumulation of embolic members into it) can be made with a second braid or weave of wires, tubes, fibers, strands, or yarns, wherein the second braid or weave is looser, less dense, and/or more open than the first braid or weave.

In an example, a proximal portion of a net or mesh can be made with a first braid or weave of wires, tubes, fibers, strands, or yarns and the distal portion of the net or mesh (which is passively expanded by the insertion and accumulation of embolic members into it) can be made with a second braid or weave of wires, tubes, fibers, strands, or yarns, wherein the second braid or weave is different than the first braid or weave. In an example, a proximal portion of a net or mesh can be made with a first braid or weave of wires, tubes, fibers, strands, or yarns and the distal portion of the net or mesh (which is passively expanded by the insertion and accumulation of embolic members into it) can be made with a second braid or weave of wires, tubes, fibers, strands, or yarns, wherein the second braid or weave is more porous than the first braid or weave.

In an example, a first portion of a net or mesh can have a first (average) porosity level and a second portion of a net or mesh can have a second (average) porosity level. In an example, a first portion of a net or mesh can have a first (cross-sectional) shape and a second portion of a net or mesh can have a second (cross-sectional) shape. In an example, a first portion of a net or mesh can have a first (cross-sectional) size and a second portion of a net or mesh can have a second (cross-sectional) size. In an example, a first portion of a net or mesh can be made with a first material and a second portion of a net or mesh can be made with a second material. In an example, a first portion of a net or mesh can be made with a first combination of materials and a second portion of a net or mesh can be made with a second combination of materials. In an example, a first portion of a net or mesh can have a first radial strength and a second portion of a net or mesh can have a second radial strength. In an example, a first portion of a net or mesh can have a first flexibility level and a second portion of a net or mesh can have a second flexibility level.

In an example, a first portion of an intrasaccular aneurysm occlusion device can have a first (average) porosity level and a second portion of an intrasaccular occlusion device can have a second (average) porosity level. In an example, a first portion of an intrasaccular aneurysm occlusion device can have a first (cross-sectional) shape and a second portion of an intrasaccular occlusion device can have a second (cross-sectional) shape. In an example, a first portion of an intrasaccular aneurysm occlusion device can have a first (cross-sectional) size and a second portion of an intrasaccular occlusion device can have a second (cross-sectional) size. In an example, a first portion of an intrasaccular aneurysm occlusion device can be made with a first material and a second portion of an intrasaccular occlusion device can be made with a second material. In an example, a first portion of an intrasaccular aneurysm occlusion device can be made with a first combination of materials and a second portion of an intrasaccular occlusion device can be made with a second combination of materials. In an example, a first portion of an intrasaccular aneurysm occlusion device can have a first radial strength and a second portion of an intrasaccular occlusion device can have a second radial strength. In an example, a first portion of an intrasaccular aneurysm occlusion device can have a first flexibility level and a second portion of an intrasaccular occlusion device can have a second flexibility level.

In an example, a distal portion of an intrasaccular aneurysm occlusion device can have a first (average) porosity level and a proximal portion of an intrasaccular occlusion device can have a second (average) porosity level. In an example, an intrasaccular aneurysm occlusion device can comprise a first portion with a first average porosity and a second portion with a second average porosity. In an example, an intrasaccular aneurysm occlusion device can comprise a distal portion with a first average porosity and a proximal portion with a second average porosity, wherein the first average porosity is greater than the second average porosity, and wherein the proximal portion is closer to the aneurysm neck when the device has been deployed in the aneurysm sac.

In an example, a higher porosity portion of an intrasaccular aneurysm occlusion device can allow blood flow through that portion of the device but a lower porosity portion of the device does not allow blood flow through that portion of the device. In an example, the portion of a deployed intrasaccular aneurysm occlusion device which is closer to the aneurysm neck can have a lower porosity than the portion of the device which is closer to the fundus of the aneurysm. In an example, the portion of a deployed intrasaccular aneurysm occlusion device which is closer to the aneurysm neck can have a lower porosity than the portion of the device which is closer to the dome of the aneurysm. In an example, the portion of a deployed intrasaccular aneurysm occlusion device which is closer to the aneurysm neck can have a lower porosity than the portion of the device which is farther from the aneurysm neck.

In an example, a distal portion of an intrasaccular aneurysm occlusion device can have a first (cross-sectional) shape and a proximal portion of an intrasaccular occlusion device can have a second (cross-sectional) shape. In an example, a distal portion of an intrasaccular aneurysm occlusion device can have a first (cross-sectional) size and a proximal portion of an intrasaccular occlusion device can have a second (cross-sectional) size. In an example, a distal portion of an intrasaccular aneurysm occlusion device can be made with a first material and a proximal portion of an intrasaccular occlusion device can be made with a second material. In an example, a distal portion of an intrasaccular aneurysm occlusion device can be made with a first combination of materials and a proximal portion of an intrasaccular occlusion device can be made with a second combination of materials. In an example, a distal portion of an intrasaccular aneurysm occlusion device can have a first radial strength and a proximal portion of an intrasaccular occlusion device can have a second radial strength. In an example, a distal portion of an intrasaccular aneurysm occlusion device can have a first flexibility level and a proximal portion of an intrasaccular occlusion device can have a second flexibility level.

In an example, the proximal portion of a net or mesh can be made from one or more materials with a first average durometer and the distal portion of the net or mesh can be made from one or more materials with a second average durometer, wherein the second average durometer is less than the first average durometer. In an example, the proximal portion of a net or mesh can be made from one or more materials with a first average durometer within the range of 50 to 200 and the distal portion of the net or mesh can be made from one or more materials with a second average durometer within the range of 10 to 50. In an example, the proximal portion of a net or mesh can be made from one or more materials with a first average durometer within the range of 70 to 120 and the distal portion of the net or mesh can be made from one or more materials with a second average durometer within the range of 5 to 70.

In an example, the proximal portion of a net or mesh can have a first level of elasticity, the distal portion of the net or mesh can have a second level of elasticity, and the second level can be greater than the first level. In an example, the proximal portion of a net or mesh can have a first level of flexibility, the distal portion of the net or mesh can have a second level of flexibility, and the second level can be greater than the first level. In an example, the proximal portion of a net or mesh can have a first level of conformability, the distal portion of the net or mesh can have a second level of conformability, and the second level can be greater than the first level. In an example, the proximal portion of a net or mesh can have a first level of resilience, the distal portion of the net or mesh can have a second level of resilience, and the second level can be less than the first level. In an example, the proximal portion of a net or mesh can have a first level of radial strength, the distal portion of the net or mesh can have a second level of radial strength, and the second level can be less than the first level. In an example, the proximal portion of a net or mesh can have a first level of stiffness, the distal portion of the net or mesh can have a second level of stiffness, and the second level can be less than the first level.

In an example, the proximal portion of a net or mesh can have a first level of post-expansion elasticity, the distal portion of the net or mesh can have a second level of post-expansion elasticity, and the second level can be greater than the first level. In an example, the proximal portion of a net or mesh can have a first level of post-expansion flexibility, the distal portion of the net or mesh can have a second level of post-expansion flexibility, and the second level can be greater than the first level. In an example, the proximal portion of a net or mesh can have a first level of post-expansion conformability, the distal portion of the net or mesh can have a second level of post-expansion conformability, and the second level can be greater than the first level. In an example, the proximal portion of a net or mesh can have a first level of post-expansion resilience, the distal portion of the net or mesh can have a second level of post-expansion resilience, and the second level can be less than the first level. In an example, the proximal portion of a net or mesh can have a first level of post-expansion radial strength, the distal portion of the net or mesh can have a second level of post-expansion radial strength, and the second level can be less than the first level. In an example, the proximal portion of a net or mesh can have a first level of post-expansion stiffness, the distal portion of the net or mesh can have a second level of post-expansion stiffness, and the second level can be less than the first level.

In an example, a net or mesh can have a proximal-to-distal axis, wherein proximal means closer to an aneurysm neck after insertion of the net or mesh into the aneurysm and distal means farther from the aneurysm neck after insertion of the net or mesh into the aneurysm sac. In an example, this proximal-to-distal axis can be virtually divided into three equal segments—a proximal segment, a middle segment, and a distal segment. In an example, a proximal-to-middle virtual plane can be defined as a virtual plane which is orthogonal to the proximal-to-distal axis and crosses the axis between the proximal segment and the middle segment. In an example, a middle-to-distal virtual plane can be defined as a virtual plane which is orthogonal to the proximal-to-distal axis and crosses the axis between the middle segment and the distal segment. In an example, a proximal portion of the net or mesh can be located proximal to the proximal-to-middle virtual plane and the distal portion of the net or mesh can be located distal to the middle-to-distal virtual plane. In an example, a proximal portion of the net or mesh can be located proximal to the proximal-to-middle virtual plane and the distal portion of the net or mesh can be located distal to the proximal-to-middle virtual plane.

In an example, the proximal-to-distal axis can be virtually divided into a series of four equal segments—a first segment (most proximal), a second segment, a third segment, and a fourth (most distal) segment. In an example, a first-to-second virtual plane can be defined as a virtual plane which is orthogonal to the proximal-to-distal axis and crosses the axis between the first segment and the second segment. In an example, a second-to-third virtual plane can be defined as a virtual plane which is orthogonal to the proximal-to-distal axis and crosses the axis between the second segment and the third segment. In an example, a third-to-fourth virtual plane can be defined as a virtual plane which is orthogonal to the proximal-to-distal axis and crosses the axis between the third segment and the fourth segment.

In an example, a proximal portion of the net or mesh can be located proximal to the first-to-second virtual plane and the distal portion of the net or mesh can be located distal to the third-to-fourth virtual plane. In an example, a proximal portion of the net or mesh can be located proximal to the first-to-second virtual plane and the distal portion of the net or mesh can be located distal to the first-to-second virtual plane. In an example, a proximal portion of the net or mesh can be located proximal to the second-to-third virtual plane and the distal portion of the net or mesh can be located distal to the third-to-fourth virtual plane. In an example, a proximal portion of the net or mesh can be located proximal to the second-to-third virtual plane and the distal portion of the net or mesh can be located distal to the second-to-third virtual plane. In an example, a proximal portion of the net or mesh can be located proximal to the third-to-fourth virtual plane and the distal portion of the net or mesh can be located distal to the third-to-fourth virtual plane.

In an example, at least one portion of a net or mesh for insertion into an aneurysm sac can be selected from the group consisting of: 3D-printed convex net or mesh, balloon with holes, braided or woven shell, braided or woven structure, braided or woven tubular structure with inverted end portions, braided or woven tubular structure with tied ends, braided textile sphere, braided wire sphere, cellular lattice, containment bag, dual-layer body, dual-layer braided or woven structure, flexible aneurysm liner, flexible metal mesh or net, hollow braided or woven structure, hollow framing structure, hollow shell structure, hollow sphere of biological cells, metal hexagonal mesh or net, polymer hexagonal mesh or net, spherical braided or woven structure, thin-wall flexible metal sphere with holes, and tubular braided or woven structure.

In an example, at least one portion of an intrasaccular aneurysm occlusion device can be made from elongate filaments which are attached to each other by welding or soldering. In an example, at least one portion of an intrasaccular aneurysm occlusion device can be made from elongate filaments which are attached to each other by epoxy bonding or other adhesion. In an example, at least one portion of an intrasaccular aneurysm occlusion device can be made from elongate filaments which are attached to each other by tying or crimping. In an example, at least one portion of an intrasaccular aneurysm occlusion device can be made from elongate filaments with different diameters. In an example, a proximal portion of a device can be made from elongate filaments comprising different materials. In an example, at least one portion of an intrasaccular aneurysm occlusion device can be made from a combination of metal and polymer filaments.

In an example, an intrasaccular aneurysm occlusion device can have distal and proximal portions with different shapes. In an example, the proximal portion can have a shape which is selected from the group consisting of: apple-shaped, barrel-shaped, bowl-shaped, bulbous, circular, clover-shaped, concave, conical, conic-section-shaped. In an example, the proximal portion can have a shape which is selected from the group consisting of: convex, cubic, cylindrical, disk-shaped, ellipsoidal, flower-petal-shaped, and globular.

In an example, the proximal portion can have a shape which is selected from the group consisting of: heart-shaped, helical, hemispherical, hexagon-shaped, hexahedron, hub-and-spokes-shaped, multi-lobed, multi-planar, non-spherical surface of revolution, noodle-shaped, oblate spheroid, octagon-shaped, octahedron, ovaloid, and pancake-shaped. In an example, the proximal portion can have a shape which is selected from the group consisting of: paraboloid of revolution, peanut-shaped, pear-shaped, pentagonal-shaped, polyhedron-shaped, prolate-spheroid-shaped, pyramidal, rectangular, and ring-shaped. In an example, the proximal portion can have a shape which is selected from the group consisting of: semi-circular, sinusoidal, shape with radially-extending-protrusions, spherical, square, star-shaped, tapered, telescoping, tetrahedronal, toroidal, and truncated-sphere-shaped.

In an example, an intrasaccular aneurysm occlusion device can further comprise a proximal opening which is positioned within the aneurysm neck, wherein embolic members are inserted through this opening into a net or mesh in the aneurysm sac. In an example, an intrasaccular aneurysm occlusion device can further comprise a proximal opening which is positioned within the aneurysm neck, wherein embolic members are inserted through this opening into the interior space of a net or mesh in the aneurysm sac. In an example, this opening can be closed after the appropriate quantity, length, or volume embolic members has been inserted into the net or mesh to prevent the embolic members from escaping (through the aneurysm neck) out of the net or mesh.

In an example, an opening through which embolic members are inserted into a net or mesh can be closed by a clamp which is remotely shut on the opening after the embolic members have been delivered. In an example, an opening through which embolic members are inserted into a net or mesh can be closed by a plug which is pushed or pulled into the opening. In an example, an opening through which embolic members are inserted into a net or mesh can be closed by a spring and/or elastic perimeter which is held open by a catheter (e.g. tube) during delivery of embolic members and then contracts when the catheter (e.g. tube) is removed after the embolic members have been delivered. In an example, an opening through which embolic members are inserted into a net or mesh can be closed by a spring-tensioned flap or cover which is held open by a catheter during delivery of embolic members and then closes when the catheter is removed after the embolic members have been delivered. In an example, an opening through which embolic members are inserted into a net or mesh can be closed by a tension member which exerts force to close the opening, wherein a piece props the opening open until it is melted, removed, or cut.

In an example, an opening through which embolic members are inserted into a net or mesh can be closed by an elastic perimeter (e.g. elastic ring) which is held open by a catheter (e.g. tube) during delivery of embolic members and then contracts when the catheter (e.g. tube) is removed after the embolic members have been delivered. In an example, an opening through which embolic members are inserted into a net or mesh can be closed by application of thermal and/or electromagnetic energy which melts, fuses, and/or welds the opening shut. In an example, an opening through which embolic members are inserted into a net or mesh can be closed by injection of adhesive material which glues the opening shut. In an example, an opening through which embolic members are inserted into a net or mesh can be closed by a user pulling a string, suture, wire or other longitudinal member which at least partially encircles and closes the opening. In an example, an opening through which embolic members are inserted into a net or mesh can be closed by the release or activation of one or more magnets whose magnetic attraction closes the opening.

In an example, an intrasaccular aneurysm occlusion device can further comprise a positioning mechanism (near the distal end of the catheter) which enables a user to remotely adjust and/or orient the position of the device relative to the orientation of an aneurysm sac and/or neck. In an example, a central neck-to-fundus axis of an aneurysm can be defined as a virtual line extending orthogonally into the aneurysm (toward the fundus of the aneurysm) from the center of the aneurysm neck. In an example, an intrasaccular aneurysm occlusion device can further comprise a positioning mechanism (near the distal end of the catheter) which enables a user to remotely align the longitudinal axis of the device with the central neck-to-fundus axis of an aneurysm. In an example, a positioning mechanism can comprise a set of grasp-and-release arms which can be remotely moved (e.g. rotated) by a user. In an example, a positioning mechanism can comprise a ball-and-socket joint which can be remotely moved (e.g. rotated) by a user. In an example, a positioning mechanism can comprise a remote 3D steering mechanism.

In an example, an intrasaccular aneurysm occlusion device can further comprise a retrieval mechanism which enables retrieving a net or mesh from an aneurysm sac and repositioning the net or mesh within the aneurysm sac. In an example, a retrieval mechanism can be selected from the group consisting of: a lasso-based retrieval mechanism; a magnetic retrieval mechanism; a pull-string or pull-wire mechanism; a retrieval mechanism with grasping arms; a sheath which is slid over the net or mesh; and a suction-based retrieval mechanism. In an example, an intrasaccular aneurysm occlusion device can further comprise a retrieval mechanism which enables retrieval of embolic members from a net or mesh within the aneurysm sac. In an example, a retrieval mechanism can be selected from the group consisting of: a lasso-based retrieval mechanism; a magnetic retrieval mechanism; a pull-string or pull-wire mechanism; a retrieval mechanism with grasping arms; a sheath which is slid over the net or mesh; and a suction-based retrieval mechanism.

In an example, a net or mesh for insertion into an aneurysm sac can be made from one or more materials selected from the group consisting of: acrylic, alginate, cobalt-chrome alloy (cobalt chromium), collagen, copolymer, ethylene vinyl alcohol (EVA), fibrin, fibrinogen, fibronectin, gelatin, gold, hydrogel, latex, and methylcellulose. In an example, a net or mesh for insertion into an aneurysm sac can be made from one or more materials selected from the group consisting of: nitinol (or other nickel titanium alloy), nylon, palladium, platinum, polycarbonate urethane (PCU), polydimethylsiloxane (PDMS), polyesters, polyether block amide (PEBA), and polyetherether ketone (PEEK), polyethylene.

In an example, a net or mesh for insertion into an aneurysm sac can be made from one or more materials selected from the group consisting of: polyethylene glycol (PEG), polyethylene terephthalate (PET), polyglycolic acid (PGA), polylactic acid (PLA), poly-N-acetylglucosamine (PNAG), polyolefin, polyoleandlena, polypropylene, polytetrafluoroethylene (PTFE), polyurethane (PU), polywanacrakor, polyvinyl alcohol (PVA), and polyvinyl pyrrolidone (PVP). In an example, a net or mesh for insertion into an aneurysm sac can be made from one or more materials selected from the group consisting of: radiopaque material, silicone, silk, small intestinal submucosa, steel (e.g. stainless steel), suneelium, tantalum, thermoplastic elastomer, titanium, tungsten, water-soluble synthetic polymer, and zirconium-based alloy.

In an example, a portion of a net or mesh can be made from polyvinyl alcohol (PVA). In an example, a portion of a net or mesh can be made from polyetherether ketone (PEEK). In an example, a portion of a net or mesh can be made from polyesters. In an example, a portion of a net or mesh can be made from alginate. In an example, a portion of a net or mesh can be made from tungsten. In an example, a portion of a net or mesh can be made from nylon. In an example, a portion of a net or mesh can be made from polyethylene terephthalate (PET).

In an example, a portion of a net or mesh can be made from silicone. In an example, a portion of a net or mesh can be made from cobalt-chrome alloy (cobalt chromium). In an example, a portion of a net or mesh can be made from polyglycolic acid (PGA). In an example, a portion of a net or mesh can be made from water-soluble synthetic polymer. In an example, a portion of a net or mesh can be made from collagen. In an example, a portion of a net or mesh can be made from polylactic acid (PLA). In an example, a portion of a net or mesh can be made from zirconium-based alloy. In an example, a portion of a net or mesh can be made from copolymer. In an example, a portion of a net or mesh can be made from poly-N-acetylglucosamine (PNAG).

In an example, a portion of a net or mesh can be made from gold. In an example, a portion of a net or mesh can be made from tantalum. In an example, a portion of a net or mesh can be made from ethylene vinyl alcohol (EVA). In an example, a portion of a net or mesh can be made from polyolefin. In an example, a portion of a net or mesh can be made from fibrin. In an example, a portion of a net or mesh can be made from fibrinogen. In an example, a portion of a net or mesh can be made from polyethylene glycol (PEG). In an example, a portion of a net or mesh can be made from polyethylene. In an example, a portion of a net or mesh can be made from gelatin. In an example, a portion of a net or mesh can be made from thermoplastic elastomer.

In an example, a portion of a net or mesh can be made from fibronectin. In an example, a portion of a net or mesh can be made from titanium. In an example, a portion of a net or mesh can be made from platinum. In an example, a portion of a net or mesh can be made from polyvinyl pyrrolidone (PVP). In an example, a portion of a net or mesh can be made from nitinol (or other nickel titanium alloy). In an example, a portion of a net or mesh can be made from silk. In an example, a portion of a net or mesh can be made from acrylic. In an example, a portion of a net or mesh can be made from polytetrafluoroethylene (PTFE). In an example, a portion of a net or mesh can be made from methylcellulose. In an example, a portion of a net or mesh can be made from small intestinal submucosa.

In an example, a portion of a net or mesh can be made from hydrogel. In an example, a portion of a net or mesh can be made from polyoleandlena. In an example, a portion of a net or mesh can be made from suneelium. In an example, a portion of a net or mesh can be made from polyether block amide (PEBA). In an example, a portion of a net or mesh can be made from palladium. In an example, a portion of a net or mesh can be made from radiopaque material. In an example, a portion of a net or mesh can be made from polydimethylsiloxane (PDMS). In an example, a portion of a net or mesh can be made from polywanacrakor.

In an example, a portion of a net or mesh can be made from polyurethane (PU). In an example, a portion of a net or mesh can be made from latex. In an example, a portion of a net or mesh can be made from polypropylene. In an example, a portion of a net or mesh can be made from steel (e.g. stainless steel). In an example, a portion of a net or mesh can be made from polycarbonate urethane (PCU).

In an example, an intrasaccular aneurysm occlusion device can be selected from the group consisting of: net; mesh; lattice; balloon; bag; and liner. In an example, intrasaccular aneurysm occlusion device can have an expanded shape selected from the group consisting of: sphere; ellipsoid; oval; egg shape; water-drop shape; pumpkin shape; torus; and disk. In an example, an intrasaccular aneurysm occlusion device can include a ring-like expandable stent, a cylindrical expandable stent, or an ellipsoid expandable stent. In an example, an intrasaccular aneurysm occlusion device can include an embolic ellipsoid which has a first orientation as it travels through a catheter and a second orientation after it exits the longitudinal lumen, wherein in the first orientation the longitudinal axis of the ellipsoid is substantively parallel to the longitudinal axis of the longitudinal lumen and wherein in the second orientation the longitudinal axis of the ellipsoid is substantially perpendicular to its prior orientation traveling through the longitudinal lumen. In an example, the embolic ellipsoid can be a wire structure. In an example, an intrasaccular aneurysm occlusion device can include an expandable torus-shaped proximal portion which self expands in an aneurysm sac. In an example, an expandable torus-shaped proximal portion can self expand because it comprises shape memory material.

In an example, a net or mesh can receive and retain a plurality of embolic members, causing the net or mesh to expand and to come into contact with and generally conform with an interior wall of the aneurysm, thereby substantially occluding the aneurysm and retaining the net or mesh enclosure within the aneurysm. In an example, a net or mesh can be folded and/or compressed while it is intravascularly guided through the body. In an example, a net or mesh can be folded as it travels through a lumen and then be unfolded within an aneurysm sac. In an example, a net or mesh can be elastic or stretchable. In an example, a net or mesh can be sufficiently elastic or stretchable that it expands when filled with an accumulation of embolic members, but not so elastic or stretchable that it allows embolic members to escape. In an example, intrasaccular aneurysm occlusion device can have an irregular expanded arcuate three-dimensional shape which conforms to the walls of an irregularly-shaped aneurysm sac. In an example, intrasaccular aneurysm occlusion device can have a first (pre-expansion) configuration in which it is folded or pleated and a second (post-expansion) configuration in which it is unfolded or unpleated.

In an example, a net or mesh can comprise at least one of: a nylon material, a polypropylene material, a polyester material, a polytetrafluorethylene material, and a polytetrafluoroethene material. In an example, a net or mesh can be radiolucent, echogenic, and/or MR-visible. In an example, a net or mesh enclosure need not have uniform tensile strength, flexibility, plasticity, and/or elasticity. In an example, a net or mesh enclosure can have non-uniform tensile strength, flexibility, plasticity, and/or elasticity. In an example, different portions of a net or mesh enclosure can have different levels of tensile strength, flexibility, plasticity, and/or elasticity. In an example, a net or mesh can be configured with at least one of a differential strength, differential flexibility, differential plasticity, or differential elasticity between different regions of the net or mesh enclosure.

In an example, an intrasacular aneurysm occlusion device can comprise a high-flexibility distal portion and a low-flexibility proximal portion. In an example, an intrasacular aneurysm occlusion device can have a distal portion with a first level of flexibility and a proximal portion with a second level of flexibility, wherein the second level is less than the first level. In an example, an intrasacular aneurysm occlusion device can have a distal portion with a first level of elasticity and a proximal portion with a second level of elasticity, wherein the second level is less than the first level. In an example, the high-flexibility distal portion of an intrasacular aneurysm occlusion device can have an irregular expanded arcuate three-dimensional shape which conforms to the walls of an irregularly-shaped aneurysm sac, while the low-flexibility proximal portion prevents the intrasacular aneurysm occlusion device from protruding out of the aneurysm sac.

In an example, an aneurysm occlusion device can have a first, compressed configuration as it travels through a catheter to an aneurysm. In an example, an aneurysm occlusion device can transition from the first, compressed configuration to a second, expanded, generally spherical configuration within the aneurysm sac. In an example, an aneurysm occlusion device can transition from the second, expanded, generally spherical configuration to a third, generally hemispherical configuration covering the interior of the aneurysm neck. In an example, an aneurysm occlusion device can form a double-thickness wire mesh which covers the aneurysm neck. In an example, distal and proximal portions of an aneurysm occlusion device can be fused, adhered, or otherwise joined together in an overlapping configuration.

In an example, an aneurysm occlusion device can comprise an intrasacular arcuate stent which is filled with embolic members. In an example, an intrasacular arcuate stent can be a self-expanding wire mesh or lattice. In an example, an intrasacular arcuate stent can have an expanded shape which is selected from the group consisting of: sphere; ellipsoid; cylinder; ring; egg shape; water drop shape; pumpkin, onion, or pear shape; folded paper lantern shape; and torus. In an example, an intrasacular arcuate stent can have a central axis which is generally perpendicular to the plane of the aneurysm neck. In an example, an intrasacular arcuate stent can have a first (compressed) configuration as it travels through a catheter into an aneurysm sac and a second (expanded) configuration after it exits the catheter within the aneurysm sac. In an example, the second (expanded) configuration can have a maximum width (in a plane parallel to the plane of the aneurysm neck) which is greater than the width of the aneurysm neck.

In an example, a net or mesh can have a proximal opening that is in open communication with a catheter. In an example, the embolic members can be introduced into the net or mesh through this proximal opening. In an example, this opening can be closed by user pulling a cord that weaves around the opening. The cord can be pulled from its proximal end at a remote location outside the body. In other examples, the opening can be closed by a wire, a tie-off, a threaded member, a shape-memory material, a clasp, an adhesive, or fusion. In an example, the opening can be closed by an elastic closure ring. In an example, an opening can have a one-way valve through which embolic members can be inserted, but cannot exit.

In an example, embolic members which are inserted into a net or mesh can be embolic coils or ribbons. In an example, embolic members which are inserted into a net or mesh can be pieces of foam or gel (such as hydrogel). In an example, embolic members which are inserted into a net or mesh can be microballs or microspheres. In an example, embolic members which are inserted into a net or mesh can be microsponges. In an example, embolic members which are inserted into a net or mesh can be filaments or yarns. In an example, liquid embolic material can be inserted into a net or mesh.

In an example, embolic members which are inserted into a net or mesh can be selected from the group consisting of: pieces of gel; pieces of foam; and micro-sponges. In an example, embolic members which are inserted into a net or mesh can be pieces of gel, such as hydrogel. In an example, embolic members which are inserted into a net or mesh can be pieces of foam. In an example, embolic members which are inserted into a net or mesh can be micro-sponges. In an example, embolic members which are inserted into a net or mesh can be microscale gel balls. In an example, embolic members which are inserted into a net or mesh can be microscale foam balls. In an example, embolic members which are inserted into a net or mesh can be microscale sponge balls. In an example, embolic members which are inserted into a net or mesh can be microscale gel polyhedrons. In an example, embolic members which are inserted into a net or mesh can be microscale foam polyhedrons. In an example, embolic members which are inserted into a net or mesh can be microscale sponge polyhedrons.

In an example, embolic members which are inserted into a net or mesh can have generally spherical or globular shapes. In an example, embolic members which are inserted into a net or mesh can have generally prolate spherical, ellipsoidal, or ovaloid shapes. In an example, embolic members which are inserted into a net or mesh can have apple, barrel, or pair shapes. In an example, embolic members which are inserted into a net or mesh can have torus or ring shapes. In an example, embolic members which are inserted into a net or mesh can have disk or pancake shapes. In an example, embolic members which are inserted into a net or mesh can have peanut or hour-glass shapes. In an example, embolic members which are inserted into a net or mesh can be polyhedrons comprised of hexagonal surfaces. In an example, embolic members which are inserted into a net or mesh can be polyhedrons comprised of quadrilateral surfaces. In an example, embolic members which are inserted into a net or mesh can be polyhedrons comprised of triangular surfaces.

In an example, an embolic member can have a shape which is selected from the group consisting of: apple-shaped, barrel-shaped, bulbous, convex, ellipsoidal, globular, oblate spheroid, ovaloid, prolate-spheroid-shaped, spherical, and truncated-sphere-shaped. In an example, an embolic member can have a shape which is selected from the group consisting of: bowl-shaped, concave, hemispherical, and paraboloid of revolution. In an example, an embolic member can have a shape which is selected from the group consisting of: cubic, hexagon-shaped, hexahedron, octagon-shaped, octahedron, pentagonal-shaped, polyhedron-shaped, pyramidal, rectangular, square, and tetrahedronal.

In an example, embolic members which are inserted into a net or mesh can have a (diameter) size within the range of 0.5 to 2 millimeters. In an example, embolic members which are inserted into a net or mesh can have a (diameter) size within the range of 1 to 5 millimeters. In an example, embolic members which are inserted into a net or mesh can have a (diameter) size within the range of 2 to 10 millimeters. In an example, embolic members which are inserted into a net or mesh can have a (diameter) size within the range of 5 to 20 millimeters. In an example, embolic members which are inserted into a net or mesh can have a (diameter) size within the range of 0.5 to 2 microns. In an example, embolic members which are inserted into a net or mesh can have a (diameter) size within the range of 1 to 5 microns. In an example, embolic members which are inserted into a net or mesh can have a (diameter) size within the range of 2 to 10 microns. In an example, embolic members which are inserted into a net or mesh can have a (diameter) size within the range of 5 to 20 microns.

In an example, between 5 and 20 embolic members can be inserted into a net or mesh. In an example, between 10 and 50 embolic members can be inserted into a net or mesh. In an example, between 20 and 100 embolic members can be inserted into a net or mesh. In an example, between 50 and 500 embolic members can be inserted into a net or mesh.

In an example, embolic members which are inserted into a net or mesh can expand in size within the net or mesh. In an example, embolic members can have a first (average) size while being delivered to an aneurysm sac via a micro-catheter and a second (average) size after expansion within the aneurysm sac, wherein the second (average) size is 10% to 50% larger than the first (average) size. In an example, embolic members can have a first (average) size while being delivered to an aneurysm sac via a micro-catheter and a second (average) size after expansion within the aneurysm sac, wherein the second (average) size is 40% to 100% larger than the first (average) size. In an example, embolic members can have a first (average) size while being delivered to an aneurysm sac via a micro-catheter and a second (average) size after expansion within the aneurysm sac, wherein the second (average) size is more than twice the first (average) size.

In an example, embolic members can self-expand within a net or mesh after they are released from a delivery catheter. In an example, embolic members can swell upon hydration from interaction with blood or other body fluid. In an example, embolic members can be expanded within the net or mesh by one or more mechanisms selected from the group consisting of: expansion due to interaction with body fluid; expansion due to application of thermal energy; expansion due to exposure to a chemical agent; and expansion due to exposure to light energy. In an example, embolics can expand by a factor of 2-5 times. In an example, embolics can expand by a factor of 4-10 times. In an example, embolics can expand by a factor of more than 10 times. In an example, embolic members can expand to a sufficiently-large size that they cannot escape from the net or mesh after insertion into the net or mesh.

In an example, three-dimensional embolic members which are inserted into a net or mesh can be soft and compressible. In an example, three-dimensional embolic members which are inserted into a net or mesh can have a durometer less than 50. In an example, three-dimensional embolic members which are inserted into a net or mesh can have an average durometer within the range of 10 to 30. In an example, three-dimensional embolic members which are inserted into a net or mesh can have an average durometer within the range of 25 to 50. In an example, three-dimensional embolic members which are inserted into a net or mesh can have an average durometer which is less than 70.

In an example, embolic members which are inserted into a net or mesh can be made from a polymer. In an example, embolic members which are inserted into a net or mesh can be made from an elastomeric polymer. In an example, embolic members which are inserted into a net or mesh can be made from a silicone-based polymer. In an example, embolic members which are inserted into a net or mesh can be made from polydimethylsiloxane (PDMS).

In an example, an embolic member can further comprise one or more layers made with different materials. In an example, an inner layer of an embolic member can be made from a first material and an outer layer of an embolic member can be made from a second material. In an example, an inner layer of an embolic member can be made from a first material with a first durometer and an outer layer of an embolic member can be made from a second material with a second durometer, wherein the second durometer is less than the first durometer. In an example, an embolic member can have an outer layer which is adhesive. In an example, an embolic member can have an outer layer with an adhesive property which is activated by application of electromagnetic and/or thermal energy. In an example, an embolic member can have an outer layer with an adhesive property which is activated by interaction with blood.

In an example, there can be a first average durometer of embolic members which are inserted into the net or mesh at a first time and a second average durometer of embolic members which are inserted into the net or mesh at a second time, wherein the second average durometer is greater than the first average durometer. In an example, there can be a first average durometer of embolic members which are inserted into the net or mesh at a first time and a second average durometer of embolic members which are inserted into the net or mesh at a second time, wherein the second average durometer is less than the first average durometer.

In an example, there can be a first average length of longitudinal strands between proximal pairs of embolic members which are inserted into a net or mesh at a first time, a second average length of longitudinal strands between proximal pairs of embolic members which are inserted into the net or mesh at a second time, and the second average length can be greater than the first average length. In an example, there can be a first average length of longitudinal strands between proximal pairs of embolic members which are inserted into a net or mesh at a first time, a second average length of longitudinal strands between proximal pairs of embolic members which are inserted into the net or mesh at a second time, and the second average length can be less than the first average length.

In an example, there can be a first set of embolic members which are inserted into a net or mesh at a first time and a second set of embolic members which are inserted into the net or mesh at a second time, wherein the second set of embolic members are closer together than the first set of embolic members. In an example, there can be a first set of embolic members which are inserted into a net or mesh at a first time and a second set of embolic members which are inserted into the net or mesh at a second time, wherein the first set of embolic members are closer together than the second set of embolic members. In an example, there can be a longitudinal series of embolic members connected by one or more longitudinal strands which is inserted into a net or mesh within an aneurysm sac, wherein embolic members in the longitudinal series are progressively closer to each other moving along the length of the series in a distal to proximal manner. In an example, there can be a longitudinal series of embolic members connected by one or more longitudinal strands which is inserted into a net or mesh within an aneurysm sac, wherein embolic members in the longitudinal series are progressively farther from each other moving along the length of the series in a distal to proximal manner.

In an example, embolic members which are inserted into the net or mesh at a first time can have first shapes, embolic members which are inserted into the net or mesh at a second time can have second shapes, and the second shape can be different than the first shape. In an example, embolic members which are inserted into the net or mesh at a first time can be made with a first (combination of) material, embolic members which are inserted into the net or mesh at a second time can be made with a second (combination of) material, and the second (combination of) material can be different from the first (combination of) material. In an example, embolic members which are inserted into the net or mesh at a first time can be made with a first (combination of) material, embolic members which are inserted into the net or mesh at a second time can be made with a second (combination of) material, and the second (combination of) material can be more flexible, elastic, and/or compliant than the first (combination of) material.

In an example, embolic members which are inserted into the net or mesh at a first time can be made with a first (combination of) material, embolic members which are inserted into the net or mesh at a second time can be made with a second (combination of) material, and the second (combination of) material can have a lower durometer than the first (combination of) material. In an example, embolic members which are inserted into the net or mesh at a first time can be made with a first (combination of) material, embolic members which are inserted into the net or mesh at a second time can be made with a second (combination of) material, and the second (combination of) material can be less flexible, elastic, and/or compliant than the first (combination of) material. In an example, embolic members which are inserted into the net or mesh at a first time can be made with a first (combination of) material, embolic members which are inserted into the net or mesh at a second time can be made with a second (combination of) material, and the second (combination of) material can have a higher durometer than the first (combination of) material.

In an example, there can be a first average size of embolic members which are inserted into the net or mesh at a first time, a second average size of embolic members which are inserted into the net or mesh at a second time, and the second average size can be greater than the first average size. In an example, there can be a first average size of embolic members which are inserted into the net or mesh at a first time, a second average size of embolic members which are inserted into the net or mesh at a second time, and the second average size can be less than the first average size.

In an example, a net or mesh can be delivered into an aneurysm sac via a catheter and/or delivery tube. In an example, a plurality of embolic members can be delivered into the net or mesh via the same catheter and/or delivery tube. In an example, a net or mesh can be delivered into an aneurysm sac via a first catheter and/or delivery tube and a plurality of embolic members can be delivered into the net or mesh via a second catheter and/or delivery tube.

In an example, embolic members can be made from ethylene vinyl alcohol (EVA). In an example, embolic members can be made from polyolefin. In an example, embolic members can be made from fibrinogen. In an example, embolic members can be made from polylactic acid (PLA). In an example, embolic members can be made from polyethylene terephthalate (PET). In an example, embolic members can be made from steel (e.g. stainless steel). In an example, embolic members can be made from methylcellulose.

In an example, embolic members can be made from acrylic. In an example, embolic members can be made from polyethylene glycol (PEG). In an example, embolic members can be made from silk. In an example, embolic members can be made from suneelarorium (SA). In an example, embolic members can be made from alginate. In an example, embolic members can be made from gold. In an example, embolic members can be made from polyethylene. In an example, embolic members can be made from polyoleandlena. In an example, embolic members can be made from tantalum. In an example, embolic members can be made from cobalt-chrome alloy (cobalt chromium).

In an example, embolic members can be made from polyetherether ketone (PEEK). In an example, embolic members can be made from polywanacrakor. In an example, embolic members can be made from thermoplastic elastomer. In an example, embolic members can be made from polycarbonate urethane (PCU). In an example, embolic members can be made from water-soluble synthetic polymer. In an example, embolic members can be made from collagen. In an example, embolic members can be made from polyvinyl alcohol (PVA).

In an example, embolic members can be made from titanium. In an example, embolic members can be made from polyether block amide (PEBA). In an example, embolic members can be made from radiopaque material. In an example, embolic members can be made from copolymer. In an example, embolic members can be made from polyvinyl pyrrolidone (PVP). In an example, embolic members can be made from polydimethylsiloxane (PDMS). In an example, embolic members can be made from zirconium-based alloy. In an example, embolic members can be made from polyesters. In an example, embolic members can be made from hydrogel. In an example, embolic members can be made from silicone. In an example, embolic members can be made from nitinol (or other nickel titanium alloy).

In an example, embolic members can be made from polyglycolic acid (PGA). In an example, embolic members can be made from small intestinal submucosa. In an example, embolic members can be made from nylon. In an example, embolic members can be made from polypropylene. In an example, embolic members can be made from platinum. In an example, embolic members can be made from polyurethane (PU). In an example, embolic members can be made from tungsten. In an example, embolic members can be made from fibrin.

In an example, embolic members can be made from poly-N-acetylglucosamine (PNAG). In an example, embolic members can be made from latex. In an example, embolic members can be made from fibronectin. In an example, embolic members can be made from palladium. In an example, embolic members can be made from polytetrafluoroethylene (PTFE). In an example, embolic members can be made from gelatin.

In an example, a selected quantity, series, length, and/or volume of embolic members can be selectively dispensed and/or detached into the net or mesh in situ by a mechanism selected from the group consisting of: breaking a connection between embolic members in a series of embolic members; cutting a connection between embolic members in a series of embolic members (e.g. with a cutting edge or laser); dissolving a connection between embolic members in a series of embolic members (e.g. with thermal energy or a chemical); electrolytic mechanism; hydraulic mechanism; injecting a flow of embolic members suspended in a liquid or gel into a net or mesh; melting a connection between embolic members in a series of embolic members (e.g. with thermal or light energy); progressing embolic members into a net or mesh via a conveyor belt (e.g. chain-based conveyor); progressing embolic members into a net or mesh via a helical conveyor (e.g. with an Archimedes' screw); pushing embolic members into a net or mesh using the force of a liquid flow; pusher rod and/or plunger; release detachment mechanism; and thermal detachment mechanism.

In an example, embolic members can differ among themselves with respect to one or more characteristics selected from the group consisting of: porosity, shape, size, material, composition, coating, radiopacity, strength, stiffness, and type.

In an example, a plurality of embolic members can be delivered into a net or mesh in a linear (longitudinal) array or series of inter-connected embolic members. In an example, a plurality of embolic members can be delivered into a net or mesh in a linear (longitudinal) array of connected embolic members, wherein this linear array can be cut, separated, and/or detached in situ (in a remote manner) at one or more selected locations by the user of the device in order to deliver a selected quantity, length, or volume or embolic members. In an example, a plurality of embolic members can be delivered into a net or mesh in a planar array of inter-connected embolic members. In an example, a plurality of embolic members can be delivered into a net or mesh in a three-dimensional array of inter-connected embolic members.

In an example, a series of embolic members can be delivered into a net or mesh, wherein successive embolic members in the series are closer together. In an example, a series of embolic members can be delivered into a net or mesh, wherein embolic members in the series are progressively closer together (as one progresses along the series in a distal to proximal manner). In an example, a series of embolic members can be delivered into a net or mesh, wherein successive embolic members in the series are farther apart from each other. In an example, a series of embolic members can be delivered into a net or mesh, wherein embolic members in the series are progressively farther apart (as one progresses along the series in a distal to proximal manner).

In an example, a series of embolic members can be delivered into a net or mesh, wherein successive embolic members in the series decrease in durometer. In an example, a series of embolic members can be delivered into a net or mesh, wherein embolic members in the series have progressively lower durometer values (as one progresses along the series in a distal to proximal manner). In an example, a series of embolic members can be delivered into a net or mesh, wherein successive embolic members in the series increase in durometer. In an example, a series of embolic members can be delivered into a net or mesh, wherein embolic members in the series have progressively higher durometer values (as one progresses along the series in a distal to proximal manner).

In an example, a series of embolic members can be delivered into a net or mesh, wherein successive embolic members in the series are made of different materials. In an example, a series of embolic members can be delivered into a net or mesh, wherein successive embolic members in the series are made of different materials, wherein these materials differ in porosity. In an example, a series of embolic members can be delivered into a net or mesh, wherein successive embolic members in the series are made of different materials, wherein these materials differ in radiopacity. In an example, a series of embolic members can be delivered into a net or mesh, wherein successive embolic members in the series are made of different materials, wherein these materials differ in stiffness. In an example, a series of embolic members can be delivered into a net or mesh, wherein successive embolic members in the series are made of different materials, wherein these materials differ in durometer.

In an example, a series of embolic members can be delivered into a net or mesh, wherein successive embolic members in the series decrease in porosity. In an example, a series of embolic members can be delivered into a net or mesh, wherein embolic members in the series become progressively less porous (as one progresses along the series in a distal to proximal manner). In an example, a series of embolic members can be delivered into a net or mesh, wherein successive embolic members in the series increase in porosity. In an example, a series of embolic members can be delivered into a net or mesh, wherein embolic members in the series become progressively more porous (as one progresses along the series in a distal to proximal manner).

In an example, a series of embolic members can be delivered into a net or mesh, wherein successive embolic members in the series differ in shape. In an example, a series of embolic members can be delivered into a net or mesh, wherein successive embolic members in the series differ in their degree of convexity. In an example, a series of embolic members can be delivered into a net or mesh, wherein successive embolic members in the series differ in their degree of concavity.

In an example, a series of embolic members can be delivered into a net or mesh, wherein successive embolic members in the series decrease in size. In an example, a series of embolic members can be delivered into a net or mesh, wherein embolic members in the series become progressively smaller (as one progresses along the series in a distal to proximal manner). In an example, a series of embolic members can be delivered into a net or mesh, wherein successive embolic members in the series increase in size. In an example, a series of embolic members can be delivered into a net or mesh, wherein embolic members in the series become progressively larger (as one progresses along the series in a distal to proximal manner).

In an example, embolic members can be soft, compressible members such as microsponges or blobs of gel. In an example, embolic members can be made from sponge, foam, or gel. In an example, embolic members can be hard, uncompressible members such as hard polymer spheres or beads. In an example, embolic members can be made from one or more materials selected from the group consisting of: cellulose, collagen, acetate, alginic acid, carboxy methyl cellulose, chitin, collagen glycosaminoglycan, divinylbenzene, ethylene glycol, ethylene glycol dimethylmathacrylate, ethylene vinyl acetate, hyaluronic acid, hydrocarbon polymer, hydroxyethylmethacrylate, methlymethacrylate, polyacrylic acid, polyamides, polyesters, polyolefins, polysaccharides, polyurethane, polyvinyl alcohol, silicone, urethane, and vinyl stearate.

In an example, embolic members can have a shape selected from the group consisting of: ball or sphere, ovoid, ellipsoid, and polyhedron. In an example, embolic members can have a Shore 00 value, indicative of softness or hardness, within a range of 5 to about 50. In an example, embolic members can have a diameter or like size within a range of 50 micrometers to 2000 micrometers. In an example, differently-sized embolic members can be used. In an example two or more different sizes of embolic members can be inserted into a net or mesh to occlude an aneurysm. In an example, embolic members can include small balls and large balls. In an example, it may be advantageous to first fill a net or mesh with larger balls and then continue filling the net or mesh with smaller balls. In another example, it may be advantageous to first fill a net or mesh with smaller balls and then continue filling the net or mesh with larger balls.

In an example, an intrasaccular aneurysm occlusion device can be filled with a "string of pearls" string (or wire) connected sequence of embolic members. In an example, an intrasaccular aneurysm occlusion device can include a series of embolic members which are connected by a strand. In an example, a device can include a string of pearls" series of embolic members which are linked by a strand (e.g. a thin flexible member). In an example, a device can include a string of pearls" series of embolic members which are centrally linked by a strand (e.g. a thin flexible member). In an example, a "string of pearls" string-or-wire connected sequence of embolic members can comprise a plurality of embolic members which are separate from each other, but pair-wise connected to each other by at least one string or wire. In an example, a plurality of members can be unevenly-spaced along the longitudinal axis of a flexible member. In an example, uneven spacing of the embolic members can be selected based on the size and shape of an aneurysm to be occluded. In an example, the distances between embolic members can vary. In an example, the space between embolic members can differ for occlusion of narrow-neck aneurysms vs. wide-neck aneurysms. In an example, distances between embolic members can become progressively shorter in a distal to proximal direction.

In an example, a line which connects embolic members can be a wire, spring, or chain. In an example, a connecting line can be a string, thread, band, fiber, or suture. In an example, embolic members can be centrally connected to each other by a connecting line. In an example, the centroids of embolic members can be connected by a connecting line. In an example, expanding arcuate embolic members can slide (e.g. up or down) along a connecting line. In an example, embolic members can slide along a connecting line, but only in one direction. In an example, a connecting line can have a ratchet structure which allows embolic members to slide closer to each other but not slide further apart. In an example, this device can further comprise a locking mechanism which stops embolic members from sliding along a connecting line. In an example, application of electromagnetic energy to a connecting line can fuse the line with the embolic members and stop them from sliding, effectively locking them in proximity to each other.

In an example, embolic members can be conveyed through a lumen to an aneurysm in a fluid flow, wherein the fluid escapes out from a net or mesh and the embolic members are retained within the net or mesh. In an example, embolic members can be conveyed through a lumen to an aneurysm by means of a moving belt or wire loop. In an example, embolic members can be conveyed through a lumen to an aneurysm by means of an Archimedes screw.

In an example, an aneurysm can be non-invasively imaged prior to delivery of a net or mesh into the aneurysm sac in order to estimate the optimal quantity, length, and/or volume of embolic members which should be inserted into the net or mesh based on the aneurysm sac size and/or shape before the procedure. In an example, an aneurysm can be non-invasively imaged using MRI, MRA, and/or 3D CTA prior to delivery of a net or mesh into the aneurysm sac in order to estimate the optimal quantity, length, and/or volume of embolic members which should be inserted into the net or mesh based on the aneurysm sac size and/or shape. In an example, a device can further comprise a mechanism which automatically tracks the quantity, length, and/or volume of embolic members which is inserted into the aneurysm. In an example, a device can further comprise a mechanism which automatically inserts the optimal quantity, length, and/or volume of embolic members into the net or mesh based on the optimal quantity, length, and/or volume of embolic members which was estimated by prior medical imaging.

In an example, an intrasaccular aneurysm occlusion device can further comprise a pressure sensor which is inserted into the net or mesh within the aneurysm sac during the procedure in order to monitor changes in intrasaccular pressure due to the accumulation of embolic members within the net or mesh. This can help to avoid under-filling or over-filling the net or mesh and, thus, avoid under-filling or over-filling the aneurysm sac. In an example, this pressure sensor can be withdrawn (along with the catheter) when the device has been fully deployed. In an example, insertion of embolic members can into the net or mesh can continue until the intrasaccular pressure level reaches a selected amount. In an example, insertion of embolic members into the net or mesh can be stopped if the intrasaccular pressure level reaches a selected amount. In an example, insertion of embolic members can into the net or mesh can continue automatically until the intrasaccular pressure level reaches a selected amount. In an example, insertion of embolic members into the net or mesh can be automatically stopped if the intrasaccular pressure level reaches a selected amount.

In an example, a plurality of embolic members which are inserted into a net or mesh can be connected to each other by one or more longitudinal members selected from the group consisting of: chain, fiber, filament, monofilament, ribbon, rod, strand, string, suture, tether, thread, tie, tube, wire, and yarn. In an example, a plurality of embolic members which are inserted into a net or mesh can be centrally inter-connected by one or more longitudinal members selected from the group consisting of: chain, fiber, filament, monofilament, ribbon, rod, strand, string, suture, tether, thread, tie, tube, wire, and yarn. In an example, a plurality of embolic members which are inserted into a net or mesh can be inter-connected by one or more longitudinal members which extend through openings in the embolic members, wherein these longitudinal members are selected from the group consisting of: chain, fiber, filament, monofilament, ribbon, rod, strand, string, suture, tether, thread, tie, tube, wire, and yarn.

In an example, the (average) length of a longitudinal strand between two embolic members can be within the range of 0.5 to 2 times the average diameter of the embolic members. In an example, the (average) length of a longitudinal strand between embolic members can be within the range of 2 to 10 times the average diameter of the embolic members. In an example, the (average) length of a longitudinal strand between embolic members can be within the range of 0.5 to 2 millimeters. In an example, the (average) length of a longitudinal strand between embolic members can be within the range of 1 to 5 millimeters. In an example, the (average) length of a longitudinal strand between embolic members can be within the range of 2 to 10 millimeters. In an example, the (average) length of a longitudinal strand between embolic members can be within the range of 5 to 20 millimeters. In an example, the (average) length of a longitudinal strand between embolic members can be within the range of 10 to 50 millimeters.

In an example, one or more longitudinal strands can connect embolic members in a linear manner like a string of pearls. In an example, a single continuous longitudinal strand can connect a plurality of embolic members. In an example, embolic members can be free to slide along the length of the single continuous longitudinal strand. In an example, embolic members can be connected to one or more longitudinal strands at fixed locations which do not slide along the one or more longitudinal strands. In an example, some embolic members in a longitudinal sequent of embolic members can be free to slide along longitudinal strands and other embolic members in the longitudinal sequence of embolic members can be fixed at selected locations which do not move. In an example, embolic members can be centrally connected to one or more longitudinal strands. In an example, one or more longitudinal strands can be connected to the centers and/or centroids of embolic members. In an example, one or more longitudinal strands can extend through holes in the centers and/or centroids of embolic members.

In an example, each pair of embolic members which are inserted into a net or mesh can be connected by a single longitudinal strand. In an example, each pair of embolic members which are inserted into a net or mesh can be centrally connected by a single longitudinal strand. In an example, each pair of embolic members which are inserted into a net or mesh can be connected by two or more longitudinal strands. In an example, each pair of embolic members which are inserted into a net or mesh can be connected by a braid of two or more longitudinal strands.

In an example, one or more longitudinal strands which connect embolic members can be strings, threads, fibers, or sutures. In an example, one or more longitudinal strands which connect embolic members can be wires, metal tubes, or filaments. In an example, one or more longitudinal strands which connect embolic members can be ribbons or bands. In an example, one or more longitudinal strands which connect embolic members can be coils or springs. In an example, one or more longitudinal strands which connect embolic members can be chains. In an example, one or more longitudinal strands which connect embolic members can be made from one or more metals. In an example, one or more longitudinal strands which connect embolic members can be made from one or more polymers. In an example, one or more longitudinal strands which connect embolic members can be made from one or more natural textile materials. In an example, one or more longitudinal strands which connect embolic members can be elastic and/or stretchable. In an example, one or more longitudinal strands which connect embolic members can be made from an elastomeric polymer. In an example, one or more longitudinal strands which connect embolic members can be made from an elastomeric silicone-based polymer. In an example, one or more longitudinal strands which connect embolic members can be made from polydimethylsiloxane (PDMS).

In an example, an intrasaccular aneurysm occlusion device can comprise: (a) an expandable net or mesh which is inserted into an aneurysm sac; wherein a proximal portion of the expandable net or mesh is configured to be a first distance from the aneurysm neck after the net or mesh has been inserted into the aneurysm sac; wherein a distal portion of the expandable net or mesh is configured to be a second distance from the aneurysm neck after the net or mesh has been inserted into the aneurysm sac; wherein the second distance is greater than the first distance; wherein the proximal portion of the expandable net or mesh has a first level of flexibility, elasticity, conformability, and/or compliance; wherein the distal portion of the expandable net or mesh has a second level of flexibility, elasticity, conformability, and/or compliance; and wherein second level of flexibility, elasticity, conformability, and/or compliance is greater than the first level of flexibility, elasticity, conformability, and/or compliance; and (b) an embolic coil which is inserted into and retained within the expandable net or mesh after the net or mesh has been inserted into the aneurysm sac.

In an example, an intrasaccular aneurysm occlusion device can comprise: (a) an expandable net or mesh which is inserted into an aneurysm sac; wherein a proximal portion of the expandable net or mesh is configured to be a first distance from the aneurysm neck after the net or mesh has been inserted into the aneurysm sac; wherein a distal portion of the expandable net or mesh is configured to be a second distance from the aneurysm neck after the net or mesh has been inserted into the aneurysm sac; wherein the second distance is greater than the first distance; wherein the proximal portion of the expandable net or mesh has a first level of flexibility, elasticity, conformability, and/or compliance; wherein the distal portion of the expandable net or mesh has a second level of flexibility, elasticity, conformability, and/or compliance; and wherein second level of flexibility, elasticity, conformability, and/or compliance is greater than the first level of flexibility, elasticity, conformability, and/or compliance; and (b) an embolic hydrogel mass which is inserted into and retained within the expandable net or mesh after the net or mesh has been inserted into the aneurysm sac.

In an example, an intrasaccular aneurysm occlusion device can comprise: (a) an expandable net or mesh which is inserted into an aneurysm sac; wherein a proximal portion of the expandable net or mesh is configured to be a first distance from the aneurysm neck after the net or mesh has been inserted into the aneurysm sac; wherein a distal portion of the expandable net or mesh is configured to be a second distance from the aneurysm neck after the net or mesh has been inserted into the aneurysm sac; wherein the second distance is greater than the first distance; wherein the proximal portion of the expandable net or mesh has a first level of flexibility, elasticity, conformability, and/or compliance; wherein the distal portion of the expandable net or mesh has a second level of flexibility, elasticity, conformability, and/or compliance; and wherein second level of flexibility, elasticity, conformability, and/or compliance is greater than the first level of flexibility, elasticity, conformability, and/or compliance; and (b) an embolic liquid which is inserted into, retained within, and congealed within the expandable net or mesh after the net or mesh has been inserted into the aneurysm sac.

In an example, an intrasaccular aneurysm occlusion device can comprise: (a) an expandable net or mesh which is inserted into an aneurysm sac; wherein a proximal portion of the expandable net or mesh is configured to be a first distance from the aneurysm neck after the net or mesh has been inserted into the aneurysm sac; wherein a distal portion of the expandable net or mesh is configured to be a second distance from the aneurysm neck after the net or mesh has been inserted into the aneurysm sac; wherein the second distance is greater than the first distance; wherein the proximal portion of the expandable net or mesh has a first level of flexibility, elasticity, conformability, and/or compliance; wherein the distal portion of the expandable net or mesh has a second level of flexibility, elasticity, conformability, and/or compliance; and wherein second level of flexibility, elasticity, conformability, and/or compliance is greater than the first level of flexibility, elasticity, conformability, and/or compliance; and (b) an undulating embolic ribbon which is inserted into and retained within the expandable net or mesh after the net or mesh has been inserted into the aneurysm sac.

In an example, an undulating embolic ribbon which is inserted into a net or mesh can have a sinusoidal shape. In an example, the right and left sides of the undulating embolic ribbon can be sinusoidal, wherein the right and left sides of the ribbon are 180-degrees out of phase with each other. In an example, the right and left sides of the undulating embolic ribbon can be sinusoidal, wherein the right and left sides of the ribbon are 90-degrees out of phase with each other. In an example, the right and left sides of the undulating embolic ribbon can be sinusoidal, wherein the right and left sides of the undulating embolic ribbon are symmetric with respect to the longitudinal axis of the undulating embolic ribbon.

In an example, an intrasaccular aneurysm occlusion device can comprise: an expandable net or mesh which is inserted into an aneurysm sac; wherein a proximal portion of the expandable net or mesh is configured to be a first distance from the aneurysm neck after the net or mesh has been inserted into the aneurysm sac; wherein a distal portion of the expandable net or mesh is configured to be a second distance from the aneurysm neck after the net or mesh has been inserted into the aneurysm sac; wherein the second distance is greater than the first distance; wherein the proximal portion of the expandable net or mesh has a first level of flexibility, elasticity, conformability, and/or compliance; wherein the distal portion of the expandable net or mesh has a second level of flexibility, elasticity, conformability, and/or compliance; wherein second level of flexibility, elasticity, conformability, and/or compliance is greater than the first level of flexibility, elasticity, conformability, and/or compliance; wherein the proximal portion of the net or mesh is made from one or more materials with a first average durometer and the distal portion of the net or mesh is made from one or more materials with a second average durometer, wherein the second average durometer is less than the first average durometer; and wherein the proximal portion of the net or mesh self expands after the net or mesh has been inserted into the aneurysm sac and the distal portion of the net or mesh is expanded by insertion and retention of the plurality of embolic members inside the net or mesh after the net or mesh has been inserted into the aneurysm sac; a plurality of three-dimensional embolic members which are inserted into and retained within the expandable net or mesh after the net or mesh has been inserted into the aneurysm sac; and one or more longitudinal strands which are inserted into the aneurysm sac, wherein the one or more longitudinal strands connect embolic members in the plurality of three-dimensional embolic members to each other.

In an example, an intrasaccular aneurysm occlusion device can comprise: an expandable net or mesh which is inserted into an aneurysm sac; wherein a proximal portion of the expandable net or mesh is configured to be a first distance from the aneurysm neck after the net or mesh has been inserted into the aneurysm sac; wherein a distal portion of the expandable net or mesh is configured to be a second distance from the aneurysm neck after the net or mesh has been inserted into the aneurysm sac; wherein the second distance is greater than the first distance; wherein the proximal portion of the expandable net or mesh has a first level of flexibility, elasticity, conformability, and/or compliance; wherein the distal portion of the expandable net or mesh has a second level of flexibility, elasticity, conformability, and/or compliance; and wherein second level of flexibility, elasticity, conformability, and/or compliance is greater than the first level of flexibility, elasticity, conformability, and/or compliance; a plurality of three-dimensional embolic members which are inserted into and retained within the expandable net or mesh after the net or mesh has been inserted into the aneurysm sac; wherein there is a first average size of embolic members which are inserted into the net or mesh at a first time, wherein there is a second average size of embolic members which are inserted into the net or mesh at a second time, and wherein the second size is less than the first size; and one or more longitudinal strands which are inserted into the aneurysm sac, wherein the one or more longitudinal strands connect embolic members in the plurality of three-dimensional embolic members to each other; wherein the one or more longitudinal strands connect embolic members in a linear pair-wise manner like a string of pearls; and wherein the one or more longitudinal strands are selected from the group consisting of: string, thread, suture, fiber, band, wire, coil, spring, and chain.

In an example, an intrasaccular aneurysm occlusion device can comprise: an expandable net or mesh which is inserted into an aneurysm sac; three-dimensional embolic members which are inserted into and retained within the expandable net or mesh after the net or mesh has been inserted into the aneurysm sac; and one or more strands which connect embolic members to each other; wherein the expandable net or mesh further comprises a radially-resilient proximal portion which self-expands within the aneurysm sac into a bowl shape, hemispherical shape, and/or inverted-umbrella shape which covers the aneurysm neck from inside the aneurysm sac; and wherein the expandable net or mesh further comprises a flexible distal portion which is expanded by the insertion and retention of embolic members within the net or mesh to conform to the shape of remaining portion of the aneurysm sac which is not filled by the proximal portion.

In an example, an intrasaccular aneurysm occlusion device can comprise: an expandable net or mesh which is inserted into an aneurysm sac; three-dimensional embolic members which are inserted into and retained within the expandable net or mesh after the net or mesh has been inserted into the aneurysm sac; and one or more strands which connect embolic members to each other; wherein the expandable net or mesh further comprises a radially-resilient proximal portion which self-expands within the aneurysm sac into an ellipsoidal or ovaliod shape which covers the aneurysm neck from inside the aneurysm sac; and wherein the expandable net or mesh further comprises a flexible distal portion which is expanded by the insertion and retention of embolic members within the net or mesh to conform to the shape of remaining portion of the aneurysm sac which is not filled by the proximal portion.

In an example, an intrasaccular aneurysm occlusion device can comprise: an expandable net or mesh which is inserted into an aneurysm sac; three-dimensional embolic members which are inserted into and retained within the expandable net or mesh after the net or mesh has been inserted into the aneurysm sac; and one or more strands which connect embolic members to each other; wherein the expandable net or mesh further comprises a radially-resilient proximal portion which self-expands within the aneurysm sac into a toroidal shape which covers the aneurysm neck from inside the aneurysm sac; and wherein the expandable net or mesh further comprises a flexible distal portion which is expanded by the insertion and retention of embolic members within the net or mesh to conform to the shape of remaining portion of the aneurysm sac which is not filled by the proximal portion.

In an example, an intrasaccular aneurysm occlusion device can comprise: an expandable net or mesh with hexagonal openings (e.g. pores) which is inserted into an aneurysm sac; three-dimensional embolic members which are inserted into and retained within the expandable net or mesh after the net or mesh has been inserted into the aneurysm sac; and one or more strands which connect embolic members to each other; wherein the expandable net or mesh further comprises a radially-resilient proximal portion which self-expands within the aneurysm sac to cover the aneurysm neck from inside the aneurysm sac; and wherein the expandable net or mesh further comprises a flexible distal portion which is expanded by the insertion and retention of embolic members within the net or mesh to conform to the shape of remaining portion of the aneurysm sac which is not filled by the proximal portion.

In an example, an intrasaccular aneurysm occlusion device can comprise: an expandable net or mesh with quadrilateral openings (e.g. pores) which is inserted into an aneurysm sac; three-dimensional embolic members which are inserted into and retained within the expandable net or mesh after the net or mesh has been inserted into the aneurysm sac; and one or more strands which connect embolic members to each other; wherein the expandable net or mesh further comprises a radially-resilient proximal portion which self-expands within the aneurysm sac to cover the aneurysm neck from inside the aneurysm sac; and wherein the expandable net or mesh further comprises a flexible distal portion which is expanded by the insertion and retention of embolic members within the net or mesh to conform to the shape of remaining portion of the aneurysm sac which is not filled by the proximal portion.

In an example, an intrasaccular aneurysm occlusion device can comprise: an expandable net or mesh which is inserted into an aneurysm sac; three-dimensional embolic members which are inserted into and retained within the expandable net or mesh after the net or mesh has been inserted into the aneurysm sac; and one or more strands which connect embolic members to each other; wherein the expandable net or mesh further comprises a metal proximal portion which self-expands within the aneurysm sac to cover the aneurysm neck from inside the aneurysm sac; and wherein the expandable net or mesh further comprises a polymer distal portion which is expanded by the insertion and retention of embolic members within the net or mesh to conform to the shape of remaining portion of the aneurysm sac which is not filled by the proximal portion.

In an example, an intrasaccular aneurysm occlusion device can comprise: an expandable net or mesh which is inserted into an aneurysm sac; three-dimensional embolic members which are inserted into and retained within the expandable net or mesh after the net or mesh has been inserted into the aneurysm sac; and one or more strands which connect embolic members to each other; wherein the expandable net or mesh further comprises a double-layer proximal portion which self-expands within the aneurysm sac to cover the aneurysm neck from inside the aneurysm sac; and wherein the expandable net or mesh further comprises a single layer distal portion which is expanded by the insertion and retention of embolic members within the net or mesh to conform to the shape of remaining portion of the aneurysm sac which is not filled by the proximal portion.

In an example, an intrasaccular aneurysm occlusion device can comprise: an expandable net or mesh which is inserted into an aneurysm sac; three-dimensional embolic members which are inserted into and retained within the expandable net or mesh after the net or mesh has been inserted into the aneurysm sac; and one or more strands which connect embolic members to each other; wherein the expandable net or mesh further comprises a multi-layer proximal portion which self-expands within the aneurysm sac to cover the aneurysm neck from inside the aneurysm sac; and wherein the expandable net or mesh further comprises a single layer distal portion which is expanded by the insertion and retention of embolic members within the net or mesh to conform to the shape of remaining portion of the aneurysm sac which is not filled by the proximal portion.

In an example, an intrasaccular aneurysm occlusion device can comprise: an expandable net or mesh which is inserted into an aneurysm sac; three-dimensional embolic members which are inserted into and retained within the expandable net or mesh after the net or mesh has been inserted into the aneurysm sac; and one or more strands which connect embolic members to each other; wherein the expandable net or mesh further comprises a high-density proximal portion which self-expands within the aneurysm sac to cover the aneurysm neck from inside the aneurysm sac; and wherein the expandable net or mesh further comprises a low-density distal portion which is expanded by the insertion and retention of embolic members within the net or mesh to conform to the shape of remaining portion of the aneurysm sac which is not filled by the proximal portion.

In an example, an intrasaccular aneurysm occlusion device can comprise: an expandable net or mesh which is inserted into an aneurysm sac; three-dimensional embolic members which are inserted into and retained within the expandable net or mesh after the net or mesh has been inserted into the aneurysm sac; and one or more strands which connect embolic members to each other; wherein the expandable net or mesh further comprises an double-layer inverted (or everted) proximal portion which self-expands within the aneurysm sac to cover the aneurysm neck from inside the aneurysm sac; and wherein the expandable net or mesh further comprises a single-layer distal portion which is expanded by the insertion and retention of embolic members within the net or mesh to conform to the shape of remaining portion of the aneurysm sac which is not filled by the proximal portion.

In an example, an intrasaccular aneurysm occlusion device can comprise: an expandable net or mesh which is inserted into an aneurysm sac; three-dimensional embolic members which are inserted into and retained within the expandable net or mesh after the net or mesh has been inserted into the aneurysm sac; and one or more strands which connect embolic members to each other; wherein the expandable net or mesh further comprises a proximal portion which self-expands within the aneurysm sac to cover the aneurysm neck from inside the aneurysm sac; and wherein the expandable net or mesh further comprises a distal portion which is expanded by the insertion and retention of embolic members within the net or mesh to conform to the shape of remaining portion of the aneurysm sac which is not filled by the proximal portion; wherein the proximal portion has a first level of flexibility, elasticity, conformability, and/or compliance; wherein the distal portion has a second level of flexibility, elasticity, conformability, and/or compliance; and wherein second level of flexibility, elasticity, conformability, and/or compliance is greater than the first level of flexibility, elasticity, conformability, and/or compliance.

In an example, an intrasaccular aneurysm occlusion device can comprise: a longitudinal catheter with an average catheter diameter; an expandable net or mesh which is delivered to an aneurysm sac through the catheter and inserted into the aneurysm sac, wherein a proximal portion of the expandable net or mesh is configured to be a first (average) distance from the aneurysm neck after the net or mesh has been inserted into the aneurysm sac, wherein a distal portion of the expandable net or mesh is configured to be a second (average) distance from the aneurysm neck after the net or mesh has been inserted into the aneurysm sac, wherein the second (average) distance is greater than the first (average) distance; wherein the proximal portion of the expandable net or mesh has a first level of flexibility, elasticity, conformability, and/or compliance; wherein the distal portion of the expandable net or mesh has a second level of flexibility, elasticity, conformability, and/or compliance; wherein second level of flexibility, elasticity, conformability, and/or compliance is greater than the first level of flexibility, elasticity, conformability, and/or compliance; and wherein proximal portion of the expandable net or mesh has openings with an average mesh opening diameter; and a plurality of three-dimensional embolic members which are connected to each other by one or more longitudinal strands (similar to a string of pearls), wherein the embolic members are delivered to the net or mesh through the catheter, wherein the embolic members are inserted into the net or mesh after the net or mesh has been inserted into the aneurysm sac, wherein the embolic members have an average pre-insertion embolic member diameter while they are being delivered through the catheter, wherein the embolic members have an average post-insertion embolic member diameter after their insertion into the net or mesh, wherein the average pre-insertion embolic member diameter is less than the average catheter diameter, and wherein the average post-insertion embolic member diameter is greater than the average mesh opening diameter.

In an example, an intrasaccular aneurysm occlusion device can comprise: a longitudinal catheter with an average catheter diameter; an expandable net or mesh which is delivered to an aneurysm sac through the catheter and inserted into the aneurysm sac, wherein a proximal portion of the expandable net or mesh is configured to be a first (average) distance from the aneurysm neck after the net or mesh has been inserted into the aneurysm sac, wherein a distal portion of the expandable net or mesh is configured to be a second (average) distance from the aneurysm neck after the net or mesh has been inserted into the aneurysm sac, wherein the second (average) distance is greater than the first (average) distance; wherein the proximal portion of the expandable net or mesh has a first level of flexibility, elasticity, conformability, and/or compliance; wherein the distal portion of the expandable net or mesh has a second level of flexibility, elasticity, conformability, and/or compliance; wherein second level of flexibility, elasticity, conformability, and/or compliance is greater than the first level of flexibility, elasticity, conformability, and/or compliance; and wherein proximal portion of the expandable net or mesh has openings with an average mesh opening diameter; and a plurality of three-dimensional embolic members which are connected to each other by one or more longitudinal strands (similar to a string of pearls), wherein the embolic members are delivered to the net or mesh through the catheter, wherein the embolic members are inserted into the net or mesh after the net or mesh has been inserted into the aneurysm sac, wherein the embolic members have an average pre-insertion embolic member diameter while they are being delivered through the catheter, wherein the embolic members have an average post-insertion embolic member diameter after their insertion into the net or mesh, wherein the average pre-insertion embolic member diameter is less the average catheter diameter, and wherein the average post-insertion embolic member diameter is at least 20% greater than the average mesh opening diameter.

In an example, an intrasaccular aneurysm occlusion device can comprise: a longitudinal catheter with an average catheter diameter; an expandable net or mesh which is delivered to an aneurysm sac through the catheter and inserted into the aneurysm sac, wherein a proximal portion of the expandable net or mesh is configured to be a first (average) distance from the aneurysm neck after the net or mesh has been inserted into the aneurysm sac, wherein a distal portion of the expandable net or mesh is configured to be a second (average) distance from the aneurysm neck after the net or mesh has been inserted into the aneurysm sac, wherein the second (average) distance is greater than the first (average) distance; wherein the proximal portion of the expandable net or mesh has a first level of flexibility, elasticity, conformability, and/or compliance; wherein the distal portion of the expandable net or mesh has a second level of flexibility, elasticity, conformability, and/or compliance; wherein second level of flexibility, elasticity, conformability, and/or compliance is greater than the first level of flexibility, elasticity, conformability, and/or compliance; and wherein proximal portion of the expandable net or mesh has openings with an average mesh opening diameter; and a plurality of three-dimensional embolic members which are connected to each other by one or more longitudinal strands (similar to a string of pearls), wherein the embolic members are delivered to the net or mesh through the catheter, wherein the embolic members are inserted into the net or mesh after the net or mesh has been inserted into the aneurysm sac, wherein the embolic members have an average pre-insertion embolic member diameter while they are being delivered through the catheter, wherein the embolic members have an average post-insertion embolic member diameter after their insertion into the net or mesh, wherein the average post-insertion embolic member diameter is at least 30% greater than the average pre-insertion embolic member diameter, wherein the average pre-insertion embolic member diameter is less the average catheter diameter, and wherein the average post-insertion embolic member diameter is at least 30% greater than the average mesh opening diameter.

In an example, an intrasaccular aneurysm occlusion device can comprise: a longitudinal catheter; an expandable net or mesh which is delivered to an aneurysm sac through the catheter and inserted into the aneurysm sac, wherein a proximal portion of the expandable net or mesh is configured to be a first (average) distance from the aneurysm neck after the net or mesh has been inserted into the aneurysm sac, wherein a distal portion of the expandable net or mesh is configured to be a second (average) distance from the aneurysm neck after the net or mesh has been inserted into the aneurysm sac, wherein the second (average) distance is greater than the first (average) distance; wherein the proximal portion of the expandable net or mesh has a first level of flexibility, elasticity, conformability, and/or compliance; wherein the distal portion of the expandable net or mesh has a second level of flexibility, elasticity, conformability, and/or compliance; wherein second level of flexibility, elasticity, conformability, and/or compliance is greater than the first level of flexibility, elasticity, conformability, and/or compliance; and a plurality of three-dimensional embolic members which are connected to each other by one or more longitudinal strands (similar to a string of pearls), wherein the embolic members are delivered through the catheter by a liquid or gelatinous flow.

In an example, an intrasaccular aneurysm occlusion device can comprise: a longitudinal catheter; an expandable net or mesh which is delivered to an aneurysm sac through the catheter and inserted into the aneurysm sac, wherein a proximal portion of the expandable net or mesh is configured to be a first (average) distance from the aneurysm neck after the net or mesh has been inserted into the aneurysm sac, wherein a distal portion of the expandable net or mesh is configured to be a second (average) distance from the aneurysm neck after the net or mesh has been inserted into the aneurysm sac, wherein the second (average) distance is greater than the first (average) distance; wherein the proximal portion of the expandable net or mesh has a first level of flexibility, elasticity, conformability, and/or compliance; wherein the distal portion of the expandable net or mesh has a second level of flexibility, elasticity, conformability, and/or compliance; wherein second level of flexibility, elasticity, conformability, and/or compliance is greater than the first level of flexibility, elasticity, conformability, and/or compliance; and a plurality of three-dimensional embolic members which are connected to each other by one or more longitudinal strands (similar to a string of pearls), wherein the embolic members are pushed through the catheter and into the net or mesh by the force of a liquid or gelatinous flow through the catheter.

In an example, an intrasaccular aneurysm occlusion device can comprise: a longitudinal catheter; an expandable net or mesh which is delivered to an aneurysm sac through the catheter and inserted into the aneurysm sac, wherein a proximal portion of the expandable net or mesh is configured to be a first (average) distance from the aneurysm neck after the net or mesh has been inserted into the aneurysm sac, wherein a distal portion of the expandable net or mesh is configured to be a second (average) distance from the aneurysm neck after the net or mesh has been inserted into the aneurysm sac, wherein the second (average) distance is greater than the first (average) distance; wherein the proximal portion of the expandable net or mesh has a first level of flexibility, elasticity, conformability, and/or compliance; wherein the distal portion of the expandable net or mesh has a second level of flexibility, elasticity, conformability, and/or compliance; wherein second level of flexibility, elasticity, conformability, and/or compliance is greater than the first level of flexibility, elasticity, conformability, and/or compliance; and a plurality of three-dimensional embolic members which are connected to each other by one or more longitudinal strands (similar to a string of pearls), wherein the embolic members are pushed through the catheter and into the net or mesh by the force of a flow of saline solution or blood plasma through the catheter.

In an example, an intrasaccular aneurysm occlusion device can comprise: a net or mesh which is inserted into within an aneurysm sac; and a string-of-pearls plurality of embolic members which are inserted into the net or mesh, wherein the embolic members are (pair-wise) interconnected by one or more longitudinal strands, and wherein the net or mesh is at least partly expanded by the insertion, retention, and accumulation of the embolic members in the net or mesh.

In an example, an intrasaccular aneurysm occlusion device can comprise: a net or mesh which is inserted into and expanded within an aneurysm sac, wherein the net or mesh has a plurality of openings, wherein the average diameter of openings in the plurality of openings after expansion of the net or mesh is a first distance; and a string-of-pearls plurality of embolic members which are inserted into the net or mesh, wherein the net or mesh is at least partly expanded by the insertion, retention, and accumulation of the embolic members in the net or mesh, wherein the average diameter of embolic members in the plurality of embolic members is a second distance, wherein the embolic members are interconnected by one or more longitudinal strands, wherein the average length of a longitudinal strand between two embolic members is a third distance, wherein the second distance is greater than the first distance, and wherein the third distance is greater than the first distance.

In an example, an intrasaccular aneurysm occlusion device can comprise: a net or mesh which is inserted into and expanded within an aneurysm sac, wherein the net or mesh has a plurality of openings, wherein the maximum diameter of openings in the plurality of openings after expansion of the net or mesh is a first distance; and a string-of-pearls plurality of embolic members which are inserted into the net or mesh, wherein the net or mesh is at least partly expanded by the insertion, retention, and accumulation of the embolic members in the net or mesh, wherein the minimum diameter of embolic members in the plurality of embolic members is a second distance, wherein the embolic members are interconnected by one or more longitudinal strands, wherein the minimum length of a longitudinal strand between two embolic members is a third distance, wherein the second distance is greater than the first distance, and wherein the third distance is greater than the first distance. The maximum diameter of openings in the net or mesh refers to openings in the main body of the net or mesh, not including a possible dedicated, closable opening in a proximal portion of the net or mesh for the insertion of embolic members into the net or mesh.

In an example, an intrasaccular aneurysm occlusion device can comprise: a net or mesh which is inserted into and expanded within an aneurysm sac, wherein the net or mesh has a plurality of openings, wherein the average diameter of openings in the plurality of openings after expansion of the net or mesh is a first distance; and a string-of-pearls plurality of embolic members which are inserted into the net or mesh, wherein the net or mesh is at least partly expanded by the insertion, retention, and accumulation of the embolic members in the net or mesh, wherein the average diameter of embolic members in the plurality of embolic members is a second distance, wherein the embolic members are interconnected by one or more longitudinal strands, wherein the average length of a longitudinal strand between two embolic members is a third distance, wherein the second distance is at least 25% greater than the first distance, and wherein the third distance is at least 25% greater than the first distance.

In an example, an intrasaccular aneurysm occlusion device can comprise: a net or mesh which is inserted into and expanded within an aneurysm sac, wherein the net or mesh has a plurality of openings, wherein the average diameter of openings in the plurality of openings after expansion of the net or mesh is a first distance; and a string-of-pearls plurality of embolic members which are inserted into the net or mesh, wherein the net or mesh is at least partly expanded by the insertion, retention, and accumulation of the embolic members in the net or mesh, wherein the average diameter of embolic members in the plurality of embolic members is a second distance, wherein the embolic members are interconnected by one or more longitudinal strands, wherein the average length of a longitudinal strand between two embolic members is a third distance, wherein the second distance is at least twice the first distance, and wherein the third distance is at least twice the first distance.

In an example, an intrasaccular aneurysm occlusion device can comprise: a net or mesh which is inserted into and expanded within an aneurysm sac, wherein the net or mesh has a plurality of openings, wherein the average diameter of openings in the plurality of openings after expansion of the net or mesh is a first distance; and a string-of-pearls plurality of embolic members which are inserted into the net or mesh, wherein the net or mesh is at least partly expanded by the insertion, retention, and accumulation of the embolic members in the net or mesh, wherein the average diameter of embolic members in the plurality of embolic members is a second distance, wherein the embolic members are interconnected by one or more longitudinal strands, wherein the average length of a longitudinal strand between two embolic members is a third distance, wherein the second distance is greater than the first distance, and wherein the third distance is greater than the second distance.

In an example, an intrasaccular aneurysm occlusion device can comprise: a net or mesh which is inserted into and expanded within an aneurysm sac, wherein the net or mesh has a plurality of openings, wherein the average diameter of openings in the plurality of openings after expansion of the net or mesh is a first distance; and a string-of-pearls plurality of embolic members which are inserted into the net or mesh, wherein the net or mesh is at least partly expanded by the insertion, retention, and accumulation of the embolic members in the net or mesh, wherein the average diameter of embolic members in the plurality of embolic members is a second distance, wherein the embolic members are interconnected by one or more longitudinal strands, wherein the average length of a longitudinal strand between two embolic members is a third distance, wherein the second distance is at least 25% greater than the first distance, and wherein the third distance is at least 25% greater than the second distance.

In an example, an intrasacular aneurysm occlusion device can have a distal component (such as a distal mesh) and a proximal component (such as a proximal mesh). The distal component (e.g. mesh) is farther from the aneurysm neck and the proximal component (e.g. mesh) is closer to the aneurysm neck. In an example, the distal component (e.g. mesh) can have a first centroid which is a first distance from the aneurysm neck and the proximal component (e.g. mesh) can have a second centroid which is a second distance from the aneurysm neck, wherein the second distance is less than the first distance. In an example, the proximal component (e.g. mesh) can span or bridge the aneurysm neck. In an example, the proximal component (e.g. mesh) can cover the aneurysm neck.

In an example, if a proximal component (e.g. mesh) has a distal-facing concavity, then a proximal portion of a distal component (e.g. mesh) can be nested within this concavity. In an example, a distal component (e.g. mesh) and a proximal component (e.g. mesh) can be connected. In an example, a distal component (e.g. mesh) and a proximal component (e.g. mesh) can be centrally connected. In an example, a distal component (e.g. mesh) and a proximal component (e.g. mesh) can be axially aligned. In an example, a distal component (e.g. mesh) and a proximal component (e.g. mesh) can be axially aligned and connected along their common axis.

In an example, a (multi-part) non-uniform surface aneurysm occlusion device can have a distal portion and a proximal portion, wherein the distal portion is farther from the aneurysm neck and the proximal portion is closer to the aneurysm neck. In an example, the distal portion can have a first centroid which is a first distance from the aneurysm neck and the proximal portion can have a second centroid which is a second distance from the aneurysm neck, wherein the second distance is less than the first distance. In an example, the proximal portion can span or bridge the aneurysm neck. In an example, the proximal portion can cover the aneurysm neck.

In an example, a distal mesh can be made with a polymer material. In an example, a distal mesh can be made with a metal. In an example, a distal mesh can be braided or woven from metal wires. In an example, a distal mesh can be made from both polymer material and metal wires. In an example, a proximal mesh can be made with a polymer material. In an example, a proximal mesh can be made with metal. In an example, a proximal mesh can be braided or woven from metal wires. In an example, a proximal mesh can be made from both polymer material and metal wires.

In an example, a distal mesh and/or a proximal mesh can be filled with embolic material (such as microsponges, hydrogels, or coils). In an example, a distal mesh can be filled with embolic material (such as microsponges, hydrogels, or coils). In an example, a proximal mesh can be filled with embolic material (such as microsponges, hydrogels, or coils). In an example, a distal mesh can be expanded by being filled with embolic material (such as microsponges, hydrogels, or coils). In an example, a proximal mesh can be expanded by being filled with embolic material (such as microsponges, hydrogels, or coils).

An aneurysm occlusion device can comprise: a generally spherical (wire and/or polymer) mesh (or net or porous balloon) which is inserted into an aneurysm sac; wherein the generally spherical mesh has a first elasticity level; wherein the generally spherical mesh centroid is a first distance from the aneurysm neck; and a bowl or paraboloid shaped (wire) mesh inserted into the aneurysm sac; wherein the bowl or paraboloid shaped mesh has a second elasticity level which is less than the first elasticity level; wherein the bowl or paraboloid shaped mesh centroid is a second distance from the aneurysm neck; wherein the second distance is less than the first distance; wherein the bowl or paraboloid shaped mesh spans the aneurysm neck; wherein the generally spherical mesh and the bowl or paraboloid shaped mesh are nested and/or connected to each other; and wherein the generally spherical mesh and/or the bowl or paraboloid shaped mesh are filled with embolic material (such as microsponges, hydrogels, or coils). An aneurysm occlusion device can comprise: a generally spherical mesh (or net or porous balloon) which is inserted into an aneurysm sac; wherein the generally spherical mesh has a first elasticity level; wherein the generally spherical mesh centroid is a first distance from the aneurysm neck; and a bowl or paraboloid shaped (wire) mesh inserted into the aneurysm sac; wherein the bowl or paraboloid shaped mesh has a second elasticity level which is less than the first elasticity level; wherein the bowl or paraboloid shaped mesh centroid is a second distance from the aneurysm neck; wherein the second distance is less than the first distance; wherein the bowl or paraboloid shaped mesh spans the aneurysm neck; wherein a portion of the generally spherical mesh is within the concavity of the bowl or paraboloid shaped mesh; and wherein the bowl or paraboloid shaped mesh is (centrally) connected to the generally spherical mesh.

An aneurysm occlusion device can comprise: a generally-spherical distal (wire and/or polymer) mesh (or net or porous balloon) which is inserted into an aneurysm sac; wherein the distal mesh has a first elasticity level; and a proximal mesh inserted into the aneurysm sac; wherein the proximal mesh is bowl or paraboloid shaped with a distal-facing concavity; wherein the proximal mesh has a second elasticity level which is less than the first elasticity level; wherein the proximal mesh spans the aneurysm neck; and wherein the proximal mesh is inside the distal mesh. An aneurysm occlusion device can comprise: a generally-spherical distal (wire and/or polymer) mesh (or net or porous balloon) which is inserted into an aneurysm sac; wherein the distal mesh has a first elasticity level; wherein the distal mesh centroid is a first distance from the aneurysm neck; and a proximal mesh inserted into the aneurysm sac; wherein the proximal mesh is bowl or paraboloid shaped with a distal-facing concavity; wherein the proximal mesh has a second elasticity level which is less than the first elasticity level; wherein the proximal mesh centroid is a second distance from the aneurysm neck; wherein the second distance is less than the first distance; wherein the proximal mesh spans the aneurysm neck; and wherein the distal mesh and/or proximal mesh are filled with embolic material (such as microsponges, hydrogels, or coils).

An aneurysm occlusion device can comprise: a generally-spherical distal mesh (or net or porous balloon) which is inserted into an aneurysm sac; wherein the distal mesh has a first elasticity level; and a proximal mesh inserted into the aneurysm sac; wherein the proximal mesh is bowl or paraboloid shaped with a distal-facing concavity; wherein the proximal mesh has a second elasticity level which is less than the first elasticity level; wherein the proximal mesh spans the aneurysm neck. An aneurysm occlusion device can comprise: a generally-spherical distal mesh (or net or porous balloon) which is inserted into an aneurysm sac; wherein the distal mesh has a first elasticity level; and a proximal mesh inserted into the aneurysm sac; wherein the proximal mesh is bowl or paraboloid shaped with a distal-facing concavity; wherein the proximal mesh has a second elasticity level which is less than the first elasticity level; wherein the proximal mesh spans the aneurysm neck; and wherein the distal mesh and/or proximal mesh are filled with embolic material (such as microsponges, hydrogels, or coils).

An aneurysm occlusion device can comprise: a generally-spherical distal mesh (or net or porous balloon) which is inserted into an aneurysm sac; wherein the distal mesh has a first elasticity level; wherein the distal mesh centroid is a first distance from the aneurysm neck; and a proximal mesh inserted into the aneurysm sac; wherein the proximal mesh is bowl or paraboloid shaped with a distal-facing concavity; wherein the proximal mesh has a second elasticity level which is less than the first elasticity level; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils). An aneurysm occlusion device can comprise: a generally-spherical distal mesh (or net or porous balloon) which is inserted into an aneurysm sac; wherein the distal mesh has a first level of elasticity, modulus of elasticity, and/or Young's modulus; wherein the distal mesh centroid is a first distance from the aneurysm neck; and a bowl shaped proximal mesh inserted into the aneurysm sac; wherein the proximal mesh has a second level of elasticity, modulus of elasticity, and/or Young's modulus which is less than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: a generally-spherical distal wire mesh inserted into an aneurysm sac; wherein the distal wire mesh has a first elasticity level; wherein the distal wire mesh is filled with embolic material (such as microsponges, hydrogels, or coils); and a proximal wire mesh inserted into the aneurysm sac; wherein the proximal mesh has a bowl, parabola, hemisphere, or inverted-umbrella shape with a distal-facing concavity; and wherein the proximal mesh has a second elasticity level which is less than the first elasticity level; wherein the proximal mesh spans the aneurysm neck. An aneurysm occlusion device can comprise: a generally-spherical flexible polymer mesh (or net) which is inserted into an aneurysm sac; wherein the polymer mesh (or net) is filled with embolic material; and a wire mesh inserted into the aneurysm sac; wherein the wire mesh has a bowl, parabola, hemisphere, or inverted-umbrella shape with a distal-facing concavity; wherein the wire mesh has a second elasticity level which is less than the first elasticity level; and wherein the wire mesh spans the aneurysm neck.

An aneurysm occlusion device can comprise: a disk or ellipsoidal shaped distal (wire and/or polymer) mesh (or net or porous balloon) which is inserted into an aneurysm sac; wherein the distal mesh has a first level of elasticity, modulus of elasticity, and/or Young's modulus; wherein the distal mesh centroid is a first distance from the aneurysm neck; and a bowl shaped proximal mesh inserted into the aneurysm sac; wherein the proximal mesh has a second level of elasticity, modulus of elasticity, and/or Young's modulus which is less than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a disk or ellipsoidal shaped distal wire mesh inserted into an aneurysm sac; wherein the distal wire mesh has a first elasticity level; wherein the distal wire mesh is filled with embolic material (such as microsponges, hydrogels, or coils); and a proximal wire mesh inserted into the aneurysm sac; wherein the proximal mesh has a bowl, parabola, hemisphere, or inverted-umbrella shape with a distal-facing concavity; wherein the proximal mesh has a second elasticity level which is less than the first elasticity level; wherein the proximal mesh spans the aneurysm neck.

An aneurysm occlusion device can comprise: a distal 3D-printed mesh inserted into an aneurysm sac; wherein the distal 3D-printed mesh is generally spherical, ball shaped, bulbous, circular, and/or globular; wherein the distal 3D-printed mesh centroid is a first distance from the aneurysm neck; and a proximal 3D-printed mesh inserted into the aneurysm sac; wherein the proximal polymer 3D-printed mesh is bowl shaped; wherein the proximal 3D-printed mesh centroid is a second distance from the aneurysm neck; wherein the second distance is less than the first distance; wherein the proximal 3D-printed mesh spans the aneurysm neck; wherein a portion of the distal 3D-printed mesh is within the concavity of the proximal 3D-printed mesh; wherein the proximal 3D-printed mesh is connected to the distal 3D-printed mesh; wherein the proximal 3D-printed mesh is axially-aligned with the distal 3D-printed mesh; and wherein the distal 3D-printed mesh and/or proximal 3D-printed mesh are filled with embolic material (such as microsponges, hydrogels, or coils). An aneurysm occlusion device can comprise: a distal 3D-printed mesh inserted into an aneurysm sac; wherein the distal 3D-printed mesh is generally spherical, ball shaped, bulbous, circular, and/or globular; wherein the distal 3D-printed mesh centroid is a first distance from the aneurysm neck; and a proximal 3D-printed mesh inserted into the aneurysm sac; wherein the proximal polymer 3D-printed mesh is bowl shaped; wherein the proximal 3D-printed mesh centroid is a second distance from the aneurysm neck; wherein the second distance is less than the first distance; wherein the proximal 3D-printed mesh spans the aneurysm neck; wherein a portion of the distal 3D-printed mesh is within the concavity of the proximal 3D-printed mesh; wherein the proximal 3D-printed mesh is connected to the distal 3D-printed mesh; and wherein the proximal 3D-printed mesh is axially-aligned with the distal 3D-printed mesh.

An aneurysm occlusion device can comprise: a distal metal mesh inserted into an aneurysm sac; wherein the distal metal mesh is generally spherical, ball shaped, bulbous, circular, and/or globular; wherein the distal metal mesh centroid is a first distance from the aneurysm neck; and a proximal metal mesh inserted into the aneurysm sac; wherein the proximal polymer metal mesh is bowl shaped; wherein the proximal metal mesh centroid is a second distance from the aneurysm neck; wherein the second distance is less than the first distance; wherein the proximal metal mesh spans the aneurysm neck; wherein a portion of the distal metal mesh is within the concavity of the proximal metal mesh; wherein the proximal metal mesh is connected to the distal metal mesh; wherein the proximal metal mesh is axially-aligned with the distal metal mesh; and wherein the distal metal mesh and/or proximal metal mesh are filled with embolic material (such as microsponges, hydrogels, or coils). An aneurysm occlusion device can comprise: a distal metal mesh inserted into an aneurysm sac; wherein the distal metal mesh is generally spherical, ball shaped, bulbous, circular, and/or globular; wherein the distal metal mesh centroid is a first distance from the aneurysm neck; and a proximal metal mesh inserted into the aneurysm sac; wherein the proximal polymer metal mesh is bowl shaped; wherein the proximal metal mesh centroid is a second distance from the aneurysm neck; wherein the second distance is less than the first distance; wherein the proximal metal mesh spans the aneurysm neck; wherein a portion of the distal metal mesh is within the concavity of the proximal metal mesh; wherein the proximal metal mesh is connected to the distal metal mesh; and wherein the proximal metal mesh is axially-aligned with the distal metal mesh.

An aneurysm occlusion device can comprise: a distal polymer mesh (or net) which is inserted into an aneurysm sac; wherein the distal mesh or net is generally spherical; wherein the distal mesh or net has a first elasticity level; wherein the distal mesh or net centroid is a first distance from the aneurysm neck; and a proximal polymer mesh (or net) which is inserted into the aneurysm sac; wherein the proximal mesh or net is also generally spherical; wherein the proximal mesh or net has a second elasticity level which is less than the first elasticity level; wherein the proximal mesh or net centroid is a second distance from the aneurysm neck; wherein the second distance is less than the first distance; wherein the proximal mesh or net spans across the inside of the aneurysm neck; wherein the proximal mesh or net is (centrally) connected to the distal mesh or net; and wherein the distal mesh or net and/or proximal mesh or net are filled with embolic material (such as microsponges, hydrogels, or coils). An aneurysm occlusion device can comprise: a distal polymer mesh (or net) which is inserted into an aneurysm sac; wherein the distal mesh or net is generally spherical; wherein the distal mesh or net has a first elasticity level; wherein the distal mesh or net centroid is a first distance from the aneurysm neck; and a proximal polymer mesh (or net) which is inserted into the aneurysm sac; wherein the proximal mesh or net is also generally spherical; wherein the proximal mesh or net has a second elasticity level which is less than the first elasticity level; wherein the proximal mesh or net centroid is a second distance from the aneurysm neck; wherein the second distance is less than the first distance; wherein the proximal mesh or net spans across the inside of the aneurysm neck; and wherein the proximal mesh or net is (centrally) connected to the distal mesh or net.

An aneurysm occlusion device can comprise: a distal polymer mesh (or net) which is inserted into an aneurysm sac; wherein the distal polymer mesh (or net) has a first elasticity level; wherein the distal polymer mesh (or net) is filled with embolic material (such as microsponges, hydrogels, or coils); and a proximal wire mesh inserted into the aneurysm sac; wherein the proximal wire mesh has a bowl, parabola, hemisphere, or inverted-umbrella shape with a distal-facing concavity; wherein the proximal wire mesh has a second elasticity level which is less than the first elasticity level; wherein the proximal wire mesh spans the aneurysm neck; and wherein a portion of the distal polymer mesh (or net) is within the concavity of the proximal wire mesh. An aneurysm occlusion device can comprise: a distal polymer mesh inserted into an aneurysm sac; wherein the distal polymer mesh is generally spherical, ball shaped, bulbous, circular, and/or globular; wherein the distal polymer mesh centroid is a first distance from the aneurysm neck; and a proximal polymer mesh inserted into the aneurysm sac; wherein the proximal polymer mesh is bowl shaped; wherein the proximal polymer mesh centroid is a second distance from the aneurysm neck; wherein the second distance is less than the first distance; wherein the proximal polymer mesh spans the aneurysm neck; wherein a portion of the distal polymer mesh is within the concavity of the proximal polymer mesh; wherein the proximal polymer mesh is connected to the distal polymer mesh; wherein the proximal polymer mesh is axially-aligned with the distal polymer mesh; and wherein the distal polymer mesh and/or proximal polymer mesh are filled with embolic material (such as microsponges, hydrogels, or coils).

An aneurysm occlusion device can comprise: a distal polymer mesh inserted into an aneurysm sac; wherein the distal polymer mesh is generally spherical, ball shaped, bulbous, circular, and/or globular; wherein the distal polymer mesh centroid is a first distance from the aneurysm neck; and a proximal polymer mesh inserted into the aneurysm sac; wherein the proximal polymer mesh is bowl shaped; wherein the proximal polymer mesh centroid is a second distance from the aneurysm neck; wherein the second distance is less than the first distance; wherein the proximal polymer mesh spans the aneurysm neck; wherein a portion of the distal polymer mesh is within the concavity of the proximal polymer mesh; wherein the proximal polymer mesh is connected to the distal polymer mesh; and wherein the proximal polymer mesh is axially-aligned with the distal polymer mesh. An aneurysm occlusion device can comprise: a distal porous balloon which is inserted into an aneurysm sac; wherein the distal porous balloon is generally spherical; wherein the distal porous balloon has a first elasticity level; wherein the distal porous balloon centroid is a first distance from the aneurysm neck; and a proximal porous balloon which is inserted into the aneurysm sac; wherein the proximal porous balloon is also generally spherical; wherein the proximal porous balloon has a second elasticity level which is less than the first elasticity level; wherein the proximal porous balloon centroid is a second distance from the aneurysm neck; wherein the second distance is less than the first distance; wherein the proximal porous balloon spans across the inside of the aneurysm neck; wherein the proximal porous balloon is (centrally) connected to the distal porous balloon; and wherein the distal porous balloon and/or proximal porous balloon are filled with embolic material (such as microsponges, hydrogels, or coils).

An aneurysm occlusion device can comprise: a distal porous balloon which is inserted into an aneurysm sac; wherein the distal porous balloon is generally spherical; wherein the distal porous balloon has a first elasticity level; wherein the distal porous balloon centroid is a first distance from the aneurysm neck; and a proximal porous balloon which is inserted into the aneurysm sac; wherein the proximal porous balloon is also generally spherical; wherein the proximal porous balloon has a second elasticity level which is less than the first elasticity level; wherein the proximal porous balloon centroid is a second distance from the aneurysm neck; wherein the second distance is less than the first distance; wherein the proximal porous balloon spans across the inside of the aneurysm neck; and wherein the proximal porous balloon is (centrally) connected to the distal porous balloon. An aneurysm occlusion device can comprise: a flexible irregularly shaped mesh (or net or porous balloon) which is inserted into an aneurysm sac; wherein the flexible irregularly shaped mesh has a first elasticity level; wherein the flexible irregularly shaped mesh (or net or porous balloon) centroid is a first distance from the aneurysm neck; and a bowl or paraboloid shaped (wire) mesh inserted into the aneurysm sac; wherein the bowl or paraboloid shaped wire mesh has a second elasticity level which is less than the first elasticity level; wherein the bowl or paraboloid shaped wire mesh centroid is a second distance from the aneurysm neck; wherein the second distance is less than the first distance; wherein the bowl or paraboloid shaped wire mesh spans the aneurysm neck; and wherein the bowl or paraboloid shaped wire mesh is nested within the flexible irregularly shaped wire mesh.

An aneurysm occlusion device can comprise: a flexible irregularly shaped mesh (or net or porous balloon) which is inserted into an aneurysm sac; wherein the flexible irregularly shaped mesh has a first elasticity level; wherein the flexible irregularly shaped mesh (or net or porous balloon) centroid is a first distance from the aneurysm neck; and a bowl or paraboloid shaped (wire) mesh inserted into the aneurysm sac; wherein the bowl or paraboloid shaped wire mesh has a second elasticity level which is less than the first elasticity level; wherein the bowl or paraboloid shaped wire mesh centroid is a second distance from the aneurysm neck; wherein the second distance is less than the first distance; wherein the bowl or paraboloid shaped wire mesh spans the aneurysm neck; and wherein the flexible irregularly shaped mesh and/or the bowl or paraboloid shaped wire mesh are filled with embolic material (such as microsponges, hydrogels, or coils). An aneurysm occlusion device can comprise: a flexible polymer mesh (or net) which is inserted into an aneurysm sac; wherein the polymer mesh (or net) is filled with embolic material; and a wire mesh inserted into the aneurysm sac; wherein the wire mesh has a bowl, parabola, hemisphere, or inverted-umbrella shape with a distal-facing concavity; wherein the wire mesh has a second elasticity level which is less than the first elasticity level; wherein the wire mesh spans the aneurysm neck.

An aneurysm occlusion device can comprise: a generally spherical (wire and/or polymer) mesh (or net or porous balloon) which is inserted into an aneurysm sac; wherein the generally spherical mesh centroid is a first distance from the aneurysm neck; and a bowl or paraboloid shaped (wire) mesh inserted into the aneurysm sac; wherein the bowl or paraboloid shaped mesh centroid is a second distance from the aneurysm neck; wherein the second distance is less than the first distance; wherein the bowl or paraboloid shaped mesh spans the aneurysm neck; and wherein the bowl or paraboloid shaped mesh is within a proximal portion of the generally spherical mesh. An aneurysm occlusion device can comprise: a generally spherical (wire and/or polymer) mesh (or net or porous balloon) which is inserted into an aneurysm sac; wherein the generally spherical mesh centroid is a first distance from the aneurysm neck; and a bowl or paraboloid shaped (wire) mesh inserted into the aneurysm sac; wherein the bowl or paraboloid shaped mesh centroid is a second distance from the aneurysm neck; wherein the second distance is less than the first distance; wherein the bowl or paraboloid shaped mesh spans the aneurysm neck; and wherein the generally spherical mesh and the bowl or paraboloid shaped mesh are connected to each other.

An aneurysm occlusion device can comprise: a generally spherical (wire and/or polymer) mesh (or net or porous balloon) which is inserted into an aneurysm sac; wherein the generally spherical mesh has a first elasticity level; wherein the generally spherical mesh (or net or porous balloon) centroid is a first distance from the aneurysm neck; and an ellipsoidal (wire) mesh inserted into the aneurysm sac; wherein the disk or ellipsoidal shaped mesh has a second elasticity level which is less than the first elasticity level; wherein the disk or ellipsoidal shaped mesh centroid is a second distance from the aneurysm neck; wherein the second distance is less than the first distance; wherein the disk or ellipsoidal shaped mesh spans the aneurysm neck; and wherein the generally spherical mesh and/or disk or ellipsoidal shaped mesh are filled with embolic material (such as microsponges, hydrogels, or coils). An aneurysm occlusion device can comprise: a generally spherical (wire and/or polymer) mesh (or net or porous balloon) which is inserted into an aneurysm sac; wherein the generally spherical mesh has a first elasticity level; wherein the generally spherical mesh centroid is a first distance from the aneurysm neck; and an ellipsoidal (wire) mesh inserted into the aneurysm sac; wherein the disk or ellipsoidal shaped mesh has a second elasticity level which is less than the first elasticity level; wherein the disk or ellipsoidal shaped mesh centroid is a second distance from the aneurysm neck; wherein the second distance is less than the first distance; wherein the disk or ellipsoidal shaped mesh spans the aneurysm neck; wherein the disk or ellipsoidal shaped mesh is (centrally) connected to the generally spherical mesh; and wherein the generally spherical mesh and/or the disk or ellipsoidal shaped mesh are filled with embolic material (such as microsponges, hydrogels, or coils).

An aneurysm occlusion device can comprise: a generally spherical (wire and/or polymer) mesh (or net or porous balloon) which is inserted into an aneurysm sac; wherein the generally spherical mesh has a first elasticity level; wherein the generally spherical mesh centroid is a first distance from the aneurysm neck; and an ellipsoidal (wire) mesh inserted into the aneurysm sac; wherein the disk or ellipsoidal shaped mesh has a second elasticity level which is less than the first elasticity level; wherein the disk or ellipsoidal shaped mesh centroid is a second distance from the aneurysm neck; wherein the second distance is less than the first distance; wherein the disk or ellipsoidal shaped mesh spans the aneurysm neck; and wherein the generally spherical mesh and/or the disk or ellipsoidal shaped mesh are filled with embolic material (such as microsponges, hydrogels, or coils). An aneurysm occlusion device can comprise: a generally spherical mesh (or net or porous balloon) which is inserted into an aneurysm sac; wherein the generally spherical mesh centroid is a first distance from the aneurysm neck; and a bowl or paraboloid shaped (wire) mesh inserted into the aneurysm sac; wherein the bowl or paraboloid shaped mesh centroid is a second distance from the aneurysm neck; wherein the second distance is less than the first distance; wherein the bowl or paraboloid shaped mesh spans the aneurysm neck; and wherein a portion of the generally spherical mesh is within the concavity of bowl or paraboloid shaped mesh.

An aneurysm occlusion device can comprise: a generally spherical mesh (or net or porous balloon) which is inserted into an aneurysm sac; wherein the generally spherical mesh centroid is a first distance from the aneurysm neck; and a bowl or paraboloid shaped (wire) mesh inserted into the aneurysm sac; wherein the bowl or paraboloid shaped mesh centroid is a second distance from the aneurysm neck; wherein the second distance is less than the first distance; wherein the bowl or paraboloid shaped mesh spans the aneurysm neck; wherein a portion of the generally spherical mesh is within the concavity of the bowl or paraboloid shaped mesh; and wherein the bowl or paraboloid shaped mesh is (centrally) connected to the generally spherical mesh. An aneurysm occlusion device can comprise: a generally spherical mesh (or net or porous balloon) which is inserted into an aneurysm sac; wherein the generally spherical mesh centroid is a first distance from the aneurysm neck; and a bowl or paraboloid shaped (wire) mesh inserted into the aneurysm sac; wherein the bowl or paraboloid shaped mesh centroid is a second distance from the aneurysm neck; wherein the second distance is less than the first distance; wherein the bowl or paraboloid shaped mesh spans the aneurysm neck; wherein the generally spherical mesh and the bowl or paraboloid shaped mesh are nested and/or connected to each other; and wherein the generally spherical mesh and/or the bowl or paraboloid shaped mesh are filled with embolic material.

An aneurysm occlusion device can comprise: a generally spherical mesh (or net or porous balloon) which is inserted into an aneurysm sac; wherein the generally spherical mesh has a first elasticity level; wherein the generally spherical mesh (or net or porous balloon) centroid is a first distance from the aneurysm neck; and an ellipsoidal (wire) mesh inserted into the aneurysm sac; wherein the disk or ellipsoidal shaped mesh has a second elasticity level which is less than the first elasticity level; wherein the disk or ellipsoidal shaped mesh centroid is a second distance from the aneurysm neck; wherein the second distance is less than the first distance; wherein the disk or ellipsoidal shaped mesh spans the aneurysm neck; and wherein the disk or ellipsoidal shaped mesh is nested within the generally spherical mesh. An aneurysm occlusion device can comprise: a generally spherical mesh (or net or porous balloon) which is inserted into an aneurysm sac; wherein the generally spherical mesh has a first elasticity level; wherein the generally spherical mesh centroid is a first distance from the aneurysm neck; and an ellipsoidal (wire) mesh inserted into the aneurysm sac; wherein the disk or ellipsoidal shaped mesh has a second elasticity level which is less than the first elasticity level;

wherein the disk or ellipsoidal shaped mesh centroid is a second distance from the aneurysm neck; wherein the second distance is less than the first distance; wherein the disk or ellipsoidal shaped mesh spans the aneurysm neck; and wherein the disk or ellipsoidal shaped mesh is (centrally) connected to the generally spherical mesh.

An aneurysm occlusion device can comprise: a generally spherical mesh (or net or porous balloon) which is inserted into an aneurysm sac; wherein the generally spherical mesh has a first elasticity level; wherein the generally spherical mesh centroid is a first distance from the aneurysm neck; and an ellipsoidal (wire) mesh inserted into the aneurysm sac; wherein the disk or ellipsoidal shaped mesh has a second elasticity level which is less than the first elasticity level; wherein the disk or ellipsoidal shaped mesh centroid is a second distance from the aneurysm neck; wherein the second distance is less than the first distance; wherein the disk or ellipsoidal shaped mesh spans the aneurysm neck; and wherein the disk or ellipsoidal shaped mesh is nested within the generally spherical wire mesh. An aneurysm occlusion device can comprise: a generally spherical non-uniform surface (wire and/or polymer) mesh inserted into an aneurysm sac; wherein the mesh further comprises a distal portion with a first elasticity level and a proximal portion; wherein the proximal portion has a second elasticity level which is less than the first elasticity level; wherein the proximal portion spans the aneurysm neck.

An aneurysm occlusion device can comprise: a generally spherical non-uniform surface mesh (or net or porous balloon) which is inserted into an aneurysm sac; wherein the mesh further comprises a distal portion with a first elasticity level and a proximal portion; wherein the proximal portion has a second elasticity level which is less than the first elasticity level; wherein the proximal portion spans the aneurysm neck; and wherein the mesh is filled with embolic material (such as microsponges, hydrogels, or coils). An aneurysm occlusion device can comprise: a generally spherical polymer and metal mesh inserted into an aneurysm sac; wherein the distal mesh has a first ratio of polymer material to metal material; and a bowl-shaped polymer and metal mesh inserted into the aneurysm sac; wherein the proximal mesh has a second ratio of polymer material to metal material which is less than the first ratio; wherein the bowl-shaped mesh spans the aneurysm; and wherein the distal mesh and/or the proximal mesh are filled with embolic material (such as microsponges, hydrogels, or coils).

An aneurysm occlusion device can comprise: a generally spherical, ball shaped, bulbous, circular, and/or globular distal mesh (or net or porous balloon) which is inserted into an aneurysm sac; wherein the distal mesh centroid is a first distance from the aneurysm neck; and a bowl shaped proximal mesh inserted into the aneurysm sac; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a generally spherical, ball shaped, bulbous, circular, and/or globular distal (wire and/or polymer) mesh (or net or porous balloon) which is inserted into an aneurysm sac; wherein the distal mesh centroid is a first distance from the aneurysm neck; and a bowl shaped proximal mesh inserted into the aneurysm sac; wherein the proximal mesh centroid is a second distance from the aneurysm neck; wherein the second distance is less than the first distance; wherein the proximal mesh spans the aneurysm neck; and wherein the proximal mesh is axially-aligned with the distal mesh.

An aneurysm occlusion device can comprise: a generally-spherical distal (wire and/or polymer) mesh (or net or porous balloon) which is inserted into an aneurysm sac; wherein the distal mesh centroid is a first distance from the aneurysm neck; and a bowl shaped proximal mesh inserted into the aneurysm sac;

wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils). An aneurysm occlusion device can comprise: a generally-spherical distal (wire and/or polymer) mesh (or net or porous balloon) which is inserted into an aneurysm sac; wherein the distal mesh has a first elasticity level; wherein the distal mesh centroid is a first distance from the aneurysm neck; and a proximal mesh (or net or porous balloon) which is inserted into the aneurysm sac; wherein the proximal mesh is also generally spherical; wherein the proximal mesh has a second elasticity level which is less than the first elasticity level; wherein the proximal mesh centroid is a second distance from the aneurysm neck; wherein the second distance is less than the first distance; wherein the proximal mesh spans across the inside of the aneurysm neck; wherein the proximal mesh is (centrally) connected to the distal mesh; and wherein the distal mesh and/or proximal mesh are filled with embolic material (such as microsponges, hydrogels, or coils).

An aneurysm occlusion device can comprise: a generally-spherical distal (wire and/or polymer) mesh (or net or porous balloon) which is inserted into an aneurysm sac; wherein the distal mesh has a first flexibility level; and a proximal mesh inserted into the aneurysm sac; wherein the proximal mesh is bowl or paraboloid shaped with a distal-facing concavity; wherein the proximal mesh has a second flexibility level which is less than the first flexibility level; wherein the proximal mesh spans the aneurysm neck; wherein a portion of the distal mesh is within the concavity of the proximal mesh; and wherein the distal mesh and/or proximal mesh are filled with embolic material (such as microsponges, hydrogels, or coils). An aneurysm occlusion device can comprise: a generally-spherical distal (wire and/or polymer) mesh (or net or porous balloon) which is inserted into an aneurysm sac; wherein the distal mesh has a first flexibility level; and a proximal mesh inserted into the aneurysm sac; wherein the proximal mesh is bowl or paraboloid shaped with a distal-facing concavity; wherein the proximal mesh has a second flexibility level which is less than the first flexibility level; wherein the proximal mesh spans the aneurysm neck; and wherein the proximal mesh is inside the distal mesh.

An aneurysm occlusion device can comprise: a generally-spherical distal (wire and/or polymer) mesh (or net or porous balloon) which is inserted into an aneurysm sac; wherein the distal mesh has a first flexibility level; wherein the distal mesh centroid is a first distance from the aneurysm neck; and a proximal mesh inserted into the aneurysm sac; wherein the proximal mesh is bowl or paraboloid shaped with a distal-facing concavity; wherein the proximal mesh has a second flexibility level which is less than the first flexibility level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; and wherein the distal mesh and/or proximal mesh are filled with embolic material (such as microsponges, hydrogels, or coils). An aneurysm occlusion device can comprise: a generally-spherical distal (wire and/or polymer) mesh (or net or porous balloon) which is inserted into an aneurysm sac; wherein the distal mesh has a first level of conformability, deformable, malleability, and/or plasticity; wherein the distal mesh centroid is a first distance from the aneurysm neck; and a bowl shaped proximal mesh inserted into the aneurysm sac; wherein the proximal mesh has a second level of conformability, deformable, malleability, and/or plasticity which is less than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is connected to the distal mesh; and wherein the distal mesh and/or proximal mesh are filled with embolic material (such as microsponges, hydrogels, or coils).

An aneurysm occlusion device can comprise: a generally-spherical distal (wire and/or polymer) mesh (or net or porous balloon) which is inserted into an aneurysm sac; wherein the distal mesh has a first level of elasticity, modulus of elasticity, and/or Young's modulus; wherein the distal mesh centroid is a first distance from the aneurysm neck; and a disk or ellipsoidal shaped proximal mesh inserted into the aneurysm sac; wherein the proximal mesh has a second level of elasticity, modulus of elasticity, and/or Young's modulus which is less than the first level; wherein the proximal mesh centroid is a second distance from the aneurysm neck; wherein the second distance is less than the first distance; wherein the proximal mesh spans the aneurysm neck; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a generally-spherical distal (wire and/or polymer) mesh (or net or porous balloon) which is inserted into an aneurysm sac; wherein the distal mesh has a first level of softness, durometer, and/or hardness; wherein the distal mesh centroid is a first distance from the aneurysm neck; and a bowl shaped proximal mesh inserted into the aneurysm sac; wherein the proximal mesh has a second level of softness, durometer, and/or hardness; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: a generally-spherical distal (wire and/or polymer) mesh (or net or porous balloon) which is inserted into an aneurysm sac; wherein the distal mesh has a first level of tensile strength; wherein the distal mesh centroid is a first distance from the aneurysm neck; and a bowl shaped proximal mesh inserted into the aneurysm sac; wherein the proximal mesh has a second level of tensile strength which is greater than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a generally-spherical distal (wire and/or polymer) mesh (or net or porous balloon) which is inserted into an aneurysm sac; wherein the distal mesh has a first porosity level; and a proximal mesh inserted into the aneurysm sac; wherein the proximal mesh is bowl or paraboloid shaped with a distal-facing concavity; wherein the proximal mesh has a second porosity level which is less than the first porosity level; wherein the proximal mesh spans the aneurysm neck.

An aneurysm occlusion device can comprise: a generally-spherical distal (wire and/or polymer) mesh (or net or porous balloon) which is inserted into an aneurysm sac; wherein the distal mesh has a first porosity level; wherein the distal mesh centroid is a first distance from the aneurysm neck; and a bowl shaped proximal mesh inserted into the aneurysm sac; wherein the proximal mesh has a second porosity level which is less than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is connected to the distal mesh; and wherein the distal mesh and/or proximal mesh are filled with embolic material (such as microsponges, hydrogels, or coils). An aneurysm occlusion device can comprise: a generally-spherical distal (wire and/or polymer) mesh (or net or porous balloon) which is inserted into an aneurysm sac; wherein the distal mesh has a first porosity level; wherein the distal mesh centroid is a first distance from the aneurysm neck; and a proximal mesh inserted into the aneurysm sac; wherein the proximal mesh is bowl or paraboloid shaped with a distal-facing concavity; wherein the proximal mesh has a second porosity level which is less than the first porosity level; wherein the proximal mesh centroid is a second distance from the aneurysm neck; wherein the second distance is less than the first distance; wherein the proximal mesh spans the aneurysm neck; and wherein the distal mesh and/or proximal mesh are filled with embolic material (such as microsponges, hydrogels, or coils).

An aneurysm occlusion device can comprise: a generally-spherical distal mesh (or net or porous balloon) which is inserted into an aneurysm sac; and a proximal mesh inserted into the aneurysm sac; wherein the proximal mesh is bowl or paraboloid shaped with a distal-facing concavity; wherein the proximal mesh spans the aneurysm neck. An aneurysm occlusion device can comprise: a generally-spherical distal mesh (or net or porous balloon) which is inserted into an aneurysm sac; wherein the distal mesh has a first elasticity level; wherein the distal mesh centroid is a first distance from the aneurysm neck; and a proximal (wire and/or polymer) mesh (or net or porous balloon) which is inserted into the aneurysm sac; wherein the proximal mesh is also generally spherical; wherein the proximal mesh has a second elasticity level which is less than the first elasticity level; wherein the proximal mesh centroid is a second distance from the aneurysm neck; wherein the second distance is less than the first distance; wherein the proximal mesh spans across the inside of the aneurysm neck; and wherein the proximal mesh is (centrally) connected to the distal mesh.

An aneurysm occlusion device can comprise: a generally-spherical distal mesh (or net or porous balloon) which is inserted into an aneurysm sac; wherein the distal mesh has a first flexibility level; and a proximal mesh inserted into the aneurysm sac; wherein the proximal mesh is bowl or paraboloid shaped with a distal-facing concavity; wherein the proximal mesh has a second flexibility level which is less than the first flexibility level; wherein the proximal mesh spans the aneurysm neck; and wherein a portion of the distal mesh is within the concavity of the proximal mesh. An aneurysm occlusion device can comprise: a generally-spherical distal mesh (or net or porous balloon) which is inserted into an aneurysm sac; wherein the distal mesh has a first flexibility level; wherein the distal mesh centroid is a first distance from the aneurysm neck; and a proximal mesh inserted into the aneurysm sac; wherein the proximal mesh is bowl or paraboloid shaped with a distal-facing concavity; wherein the proximal mesh has a second flexibility level which is less than the first flexibility level; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils).

An aneurysm occlusion device can comprise: a generally-spherical distal mesh (or net or porous balloon) which is inserted into an aneurysm sac; wherein the distal mesh has a first level of compliance and/or compressibility; wherein the distal mesh centroid is a first distance from the aneurysm neck; and a bowl shaped proximal mesh inserted into the aneurysm sac; wherein the proximal mesh has a second level of compliance and/or compressibility which is less than the first level; wherein the proximal mesh centroid is a second distance from the aneurysm neck; wherein the second distance is less than the first distance; wherein the proximal mesh spans the aneurysm neck; wherein the proximal mesh is connected to the distal mesh; and wherein the distal mesh and/or proximal mesh are filled with embolic material (such as microsponges, hydrogels, or coils). An aneurysm occlusion device can comprise: a generally-spherical distal mesh (or net or porous balloon) which is inserted into an aneurysm sac; wherein the distal mesh has a first level of elasticity, modulus of elasticity, and/or Young's modulus; wherein the distal mesh centroid is a first distance from the aneurysm neck; and a generally spherical proximal mesh inserted into the aneurysm sac; wherein the proximal mesh has a second level of elasticity, modulus of elasticity, and/or Young's modulus which is less than the first level; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils).

An aneurysm occlusion device can comprise: a generally-spherical distal mesh (or net or porous balloon) which is inserted into an aneurysm sac; wherein the distal mesh has a first level of porosity; wherein the distal mesh centroid is a first distance from the aneurysm neck; and a bowl shaped proximal mesh inserted into the aneurysm sac; wherein the proximal mesh has a second level of porosity which is less than the first level; wherein the proximal mesh centroid is a second distance from the aneurysm neck; wherein the second distance is less than the first distance; wherein the proximal mesh spans the aneurysm neck; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a generally-spherical distal mesh (or net or porous balloon) which is inserted into an aneurysm sac; wherein the distal mesh has a first level of stretchability and/or ductility; wherein the distal mesh centroid is a first distance from the aneurysm neck; and a bowl shaped proximal mesh inserted into the aneurysm sac; wherein the proximal mesh has a second level of stretchability and/or ductility which is less than the first level; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils).

An aneurysm occlusion device can comprise: a generally-spherical distal mesh (or net or porous balloon) which is inserted into an aneurysm sac; wherein the distal mesh has a first porosity level; and a proximal mesh inserted into the aneurysm sac; wherein the proximal mesh is bowl or paraboloid shaped with a distal-facing concavity; wherein the proximal mesh has a second porosity level which is less than the first porosity level; wherein the proximal mesh spans the aneurysm neck; and wherein the distal mesh and/or proximal mesh are filled with embolic material (such as microsponges, hydrogels, or coils). An aneurysm occlusion device can comprise: a generally-spherical distal mesh (or net or porous balloon) which is inserted into an aneurysm sac; wherein the distal mesh has a first porosity level; and a proximal mesh inserted into the aneurysm sac; wherein the proximal mesh is bowl or paraboloid shaped with a distal-facing concavity; wherein the proximal mesh has a second porosity level which is less than the first porosity level; wherein the proximal mesh spans the aneurysm neck; and wherein the proximal mesh is inside the distal mesh.

An aneurysm occlusion device can comprise: a generally-spherical distal mesh (or net or porous balloon) which is inserted into an aneurysm sac; wherein the distal mesh has a first porosity level; wherein the distal mesh centroid is a first distance from the aneurysm neck; and a proximal mesh inserted into the aneurysm sac; wherein the proximal mesh is bowl or paraboloid shaped with a distal-facing concavity; wherein the proximal mesh has a second porosity level which is less than the first porosity level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a generally-spherical distal wire mesh inserted into an aneurysm sac; wherein the distal wire mesh has a first elasticity level; wherein the distal wire mesh centroid is a first distance from the aneurysm neck; and a proximal wire mesh inserted into the aneurysm sac; wherein the proximal wire mesh is also generally spherical; wherein the proximal wire mesh has a second elasticity level which is less than the first elasticity level; wherein the proximal wire mesh centroid is a second distance from the aneurysm neck; wherein the second distance is less than the first distance; wherein the proximal wire mesh spans across the inside of the aneurysm neck; wherein the proximal wire mesh is (centrally) connected to the distal wire mesh; and wherein the distal wire mesh and/or proximal wire mesh are filled with embolic material (such as microsponges, hydrogels, or coils).

An aneurysm occlusion device can comprise: a generally-spherical distal wire mesh inserted into an aneurysm sac; wherein the distal wire mesh has a first elasticity level; wherein the distal wire mesh centroid is a first distance from the aneurysm neck; and a proximal wire mesh inserted into the aneurysm sac; wherein the proximal wire mesh is also generally spherical; wherein the proximal wire mesh has a second elasticity level which is less than the first elasticity level; wherein the proximal wire mesh centroid is a second distance from the aneurysm neck; wherein the second distance is less than the first distance; wherein the proximal wire mesh spans across the inside of the aneurysm neck; and wherein the proximal wire mesh is (centrally) connected to the distal wire mesh. An aneurysm occlusion device can comprise: a peanut or hourglass shaped distal (wire and/or polymer) mesh inserted into an aneurysm sac; wherein the distal mesh has a first level of elasticity, modulus of elasticity, and/or Young's modulus; wherein the distal mesh centroid is a first distance from the aneurysm neck; and a bowl shaped proximal mesh inserted into the aneurysm sac; wherein the proximal mesh has a second level of elasticity, modulus of elasticity, and/or Young's modulus which is less than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; and wherein the proximal mesh is connected to the distal mesh.

An aneurysm occlusion device can comprise: a peanut or hourglass shaped distal mesh inserted into an aneurysm sac; wherein the distal mesh has a first elasticity level; wherein the distal mesh centroid is a first distance from the aneurysm neck; and a bowl shaped proximal mesh inserted into the aneurysm sac; wherein the proximal mesh has a second elasticity level which is less than the first elasticity level; wherein the proximal mesh centroid is a second distance from the aneurysm neck; wherein the second distance is less than the first distance; wherein the proximal mesh spans the aneurysm neck; and wherein the proximal mesh is connected to the distal mesh. An aneurysm occlusion device can comprise: an apple or barrel shaped distal (wire and/or polymer) mesh inserted into an aneurysm sac; wherein the distal mesh has a first level of elasticity, modulus of elasticity, and/or Young's modulus; wherein the distal mesh centroid is a first distance from the aneurysm neck; and a bowl shaped proximal mesh inserted into the aneurysm sac; wherein the proximal mesh has a second level of elasticity, modulus of elasticity, and/or Young's modulus which is less than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: an apple or barrel shaped distal mesh inserted into an aneurysm sac; wherein the distal mesh has a first elasticity level; wherein the distal mesh centroid is a first distance from the aneurysm neck; and a bowl shaped proximal mesh inserted into the aneurysm sac; wherein the proximal mesh has a second elasticity level which is less than the first elasticity level; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils). An aneurysm occlusion device can comprise: an irregular (3D-printed) shaped distal (wire and/or polymer) mesh (or net or porous balloon) which is inserted into an aneurysm sac; wherein the distal mesh has a first elasticity level; wherein the distal mesh centroid is a first distance from the aneurysm neck; and a bowl shaped proximal mesh inserted into the aneurysm sac; wherein the proximal mesh has a second elasticity level which is less than the first elasticity level; wherein the proximal mesh centroid is a second distance from the aneurysm neck; wherein the second distance is less than the first distance; wherein the proximal mesh spans the aneurysm neck; wherein the proximal mesh is connected to the distal mesh; and wherein the distal mesh and/or proximal mesh are filled with embolic material (such as microsponges, hydrogels, or coils).

An aneurysm occlusion device can comprise: an irregular (3D-printed) shaped distal (wire and/or polymer) mesh (or net or porous balloon) which is inserted into an aneurysm sac; wherein the distal mesh has a first level of elasticity, modulus of elasticity, and/or Young's modulus; wherein the distal mesh centroid is a first distance from the aneurysm neck; and a bowl shaped proximal mesh inserted into the aneurysm sac; wherein the proximal mesh has a second level of elasticity, modulus of elasticity, and/or Young's modulus which is less than the first level; wherein the proximal mesh centroid is a second distance from the aneurysm neck; wherein the second distance is less than the first distance; wherein the proximal mesh spans the aneurysm neck; and wherein the distal mesh and/or proximal mesh are filled with embolic material (such as microsponges, hydrogels, or coils). An aneurysm occlusion device can comprise: a disk or ellipsoidal shaped distal (wire and/or polymer) mesh (or net or porous balloon) which is inserted into an aneurysm sac; wherein the distal mesh has a first flexibility level; wherein the distal mesh centroid is a first distance from the aneurysm neck; and a bowl shaped proximal mesh inserted into the aneurysm sac; wherein the proximal mesh has a second flexibility level which is less than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: a disk or ellipsoidal shaped distal (wire and/or polymer) mesh (or net or porous balloon) which is inserted into an aneurysm sac; wherein the distal mesh has a first level of conformability, deformable, malleability, and/or plasticity; wherein the distal mesh centroid is a first distance from the aneurysm neck; and a bowl shaped proximal mesh inserted into the aneurysm sac; wherein the proximal mesh has a second level of conformability, deformable, malleability, and/or plasticity which is less than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a disk or ellipsoidal shaped distal (wire and/or polymer) mesh (or net or porous balloon) which is inserted into an aneurysm sac; wherein the distal mesh has a first level of softness, durometer, and/or hardness; wherein the distal mesh centroid is a first distance from the aneurysm neck; and a bowl shaped proximal mesh inserted into the aneurysm sac; wherein the proximal mesh has a second level of softness, durometer, and/or hardness; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: a disk or ellipsoidal shaped distal (wire and/or polymer) mesh (or net or porous balloon) which is inserted into an aneurysm sac; wherein the distal mesh has a first level of tensile strength; wherein the distal mesh centroid is a first distance from the aneurysm neck; and a bowl shaped proximal mesh inserted into the aneurysm sac; wherein the proximal mesh has a second level of tensile strength which is greater than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a disk or ellipsoidal shaped distal mesh (or net or porous balloon) which is inserted into an aneurysm sac; wherein the distal mesh centroid is a first distance from the aneurysm neck; and a bowl shaped proximal mesh inserted into the aneurysm sac; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: a disk or ellipsoidal shaped distal mesh (or net or porous balloon) which is inserted into an aneurysm sac; wherein the distal mesh centroid is a first distance from the aneurysm neck; and a proximal mesh inserted into the aneurysm sac; wherein the proximal mesh is hemispherical, bowl shaped, dome shaped, inverted dome shaped, inverted umbrella shaped, parabolic, paraboloid shaped, prolate hemisphere shaped, reflected parabola shaped, semi-circular, and/or umbrella shaped; wherein the proximal mesh centroid is a second distance from the aneurysm neck; wherein the second distance is less than the first distance; wherein the proximal mesh spans the aneurysm neck; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a disk or ellipsoidal shaped distal mesh (or net or porous balloon) which is inserted into an aneurysm sac; wherein the distal mesh has a first elasticity level; wherein the distal mesh centroid is a first distance from the aneurysm neck; and a bowl shaped proximal mesh inserted into the aneurysm sac; wherein the proximal mesh has a second elasticity level which is less than the first elasticity level; wherein the proximal mesh centroid is a second distance from the aneurysm neck; wherein the second distance is less than the first distance; wherein the proximal mesh spans the aneurysm neck; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: a disk or ellipsoidal shaped distal mesh (or net or porous balloon) which is inserted into an aneurysm sac; wherein the distal mesh has a first level of compliance and/or compressibility; wherein the distal mesh centroid is a first distance from the aneurysm neck; and a bowl shaped proximal mesh inserted into the aneurysm sac; wherein the proximal mesh has a second level of compliance and/or compressibility which is greater than the first level; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils). An aneurysm occlusion device can comprise: a disk or ellipsoidal shaped distal mesh (or net or porous balloon) which is inserted into an aneurysm sac; wherein the distal mesh has a first level of porosity; wherein the distal mesh centroid is a first distance from the aneurysm neck; and a bowl shaped proximal mesh inserted into the aneurysm sac; wherein the proximal mesh has a second level of porosity which is less than the first level; wherein the proximal mesh centroid is a second distance from the aneurysm neck; wherein the second distance is less than the first distance; wherein the proximal mesh spans the aneurysm neck; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: a disk or ellipsoidal shaped distal mesh (or net or porous balloon) which is inserted into an aneurysm sac; wherein the distal mesh has a first level of stretchability and/or ductility; wherein the distal mesh centroid is a first distance from the aneurysm neck; and a bowl shaped proximal mesh inserted into the aneurysm sac; wherein the proximal mesh has a second level of stretchability and/or ductility which is less than the first level; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils). An aneurysm occlusion device can comprise: a disk or ellipsoidal shaped distal mesh (or net or porous balloon) which is inserted into an aneurysm sac; wherein the distal mesh has a first porosity level; wherein the distal mesh centroid is a first distance from the aneurysm neck; and a bowl shaped proximal mesh inserted into the aneurysm sac; wherein the proximal mesh has a second porosity level which is less than the first level; wherein the proximal mesh centroid is a second distance from the aneurysm neck; wherein the second distance is less than the first distance; wherein the proximal mesh spans the aneurysm neck; wherein the proximal mesh is connected to the distal mesh; and wherein the distal mesh and/or proximal mesh are filled with embolic material (such as microsponges, hydrogels, or coils).

An aneurysm occlusion device can comprise: a disk or ellipsoidal shaped distal (wire and/or polymer) mesh (or net or porous balloon) which is inserted into an aneurysm sac; wherein the distal mesh has a first level of elasticity, modulus of elasticity, and/or Young's modulus; wherein the distal mesh centroid is a first distance from the aneurysm neck; and a bowl shaped proximal mesh inserted into the aneurysm sac; wherein the proximal mesh has a second level of elasticity, modulus of elasticity, and/or Young's modulus which is less than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a distal (wire and/or polymer) mesh (or net or porous balloon) which is inserted into an aneurysm sac; wherein the distal mesh has is barrel shaped, apple shaped, hourglass shaped, peanut shaped, and/or pumpkin shaped; wherein the distal mesh centroid is a first distance from the aneurysm neck; and a proximal mesh inserted into the aneurysm sac; wherein the proximal mesh is hemispherical, bowl shaped, dome shaped, inverted dome shaped, inverted umbrella shaped, parabolic, paraboloid shaped, prolate hemisphere shaped, reflected parabola shaped, semi-circular, and/or umbrella shaped; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: a distal (wire and/or polymer) mesh (or net or porous balloon) which is inserted into an aneurysm sac; wherein the distal mesh is barrel shaped, apple shaped, hourglass shaped, peanut shaped, and/or pumpkin shaped; wherein the distal mesh centroid is a first distance from the aneurysm neck; and a proximal mesh inserted into the aneurysm sac; wherein the proximal mesh is hemispherical, bowl shaped, dome shaped, inverted dome shaped, inverted umbrella shaped, parabolic, paraboloid shaped, prolate hemisphere shaped, reflected parabola shaped, semi-circular, and/or umbrella shaped; wherein the proximal mesh centroid is a second distance from the aneurysm neck; wherein the second distance is less than the first distance; wherein the proximal mesh spans the aneurysm neck; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a distal (wire and/or polymer) mesh (or net or porous balloon) which is inserted into an aneurysm sac; wherein the distal mesh is concave; wherein the distal mesh centroid is a first distance from the aneurysm neck; and a bowl shaped proximal mesh inserted into the aneurysm sac; wherein the proximal mesh centroid is a second distance from the aneurysm neck; wherein the second distance is less than the first distance; wherein the proximal mesh spans the aneurysm neck; wherein the proximal mesh is connected to the distal mesh; and wherein the distal mesh and/or proximal mesh are filled with embolic material (such as microsponges, hydrogels, or coils).

An aneurysm occlusion device can comprise: a distal (wire and/or polymer) mesh (or net or porous balloon) which is inserted into an aneurysm sac; wherein the distal mesh is convex; wherein the distal mesh centroid is a first distance from the aneurysm neck; and a bowl shaped proximal mesh inserted into the aneurysm sac; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; and wherein the distal mesh and/or proximal mesh are filled with embolic material (such as microsponges, hydrogels, or coils). An aneurysm occlusion device can comprise: a distal (wire and/or polymer) mesh (or net or porous balloon) which is inserted into an aneurysm sac; wherein the distal mesh is ellipsoidal, compressed sphere shaped, elliptical, oblate spheroid shaped, oblong, oval shaped, and/or ovaloid; wherein the distal mesh centroid is a first distance from the aneurysm neck; and a bowl shaped proximal mesh inserted into the aneurysm sac; wherein the proximal mesh centroid is a second distance from the aneurysm neck; wherein the second distance is less than the first distance; wherein the proximal mesh spans the aneurysm neck; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: a distal (wire and/or polymer) mesh (or net or porous balloon) which is inserted into an aneurysm sac; wherein the distal mesh is generally ellipsoidal, egg shaped, or apple shaped; wherein the distal mesh has a first elasticity level; wherein the distal mesh centroid is a first distance from the aneurysm neck; and a proximal mesh inserted into the aneurysm sac; wherein the proximal mesh is bowl or paraboloid shaped with a distal-facing concavity; wherein the proximal mesh has a second elasticity level which is less than the first elasticity level; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils). An aneurysm occlusion device can comprise: a distal (wire and/or polymer) mesh (or net or porous balloon) which is inserted into an aneurysm sac; wherein the distal mesh is generally ellipsoidal, egg shaped, or apple shaped; wherein the distal mesh has a first elasticity level; and a proximal mesh inserted into the aneurysm sac; wherein the proximal mesh is bowl or paraboloid shaped with a distal-facing concavity; wherein the proximal mesh has a second elasticity level which is less than the first elasticity level; wherein the proximal mesh spans the aneurysm neck; and wherein the distal mesh and/or proximal mesh are filled with embolic material (such as microsponges, hydrogels, or coils).

An aneurysm occlusion device can comprise: a distal (wire and/or polymer) mesh (or net or porous balloon) which is inserted into an aneurysm sac; wherein the distal mesh is generally ellipsoidal, egg shaped, or apple shaped; wherein the distal mesh has a first elasticity level; and a proximal mesh inserted into the aneurysm sac; wherein the proximal mesh is bowl or paraboloid shaped with a distal-facing concavity; wherein the proximal mesh has a second elasticity level which is less than the first elasticity level; wherein the proximal mesh spans the aneurysm neck; and wherein the proximal mesh is inside the distal mesh. An aneurysm occlusion device can comprise: a distal (wire and/or polymer) mesh (or net or porous balloon) which is inserted into an aneurysm sac; wherein the distal mesh is helical; wherein the distal mesh centroid is a first distance from the aneurysm neck; and a bowl shaped proximal mesh inserted into the aneurysm sac; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: a distal (wire and/or polymer) mesh (or net or porous balloon) which is inserted into an aneurysm sac; wherein the distal mesh is helical; wherein the distal mesh centroid is a first distance from the aneurysm neck; and a proximal mesh inserted into the aneurysm sac; wherein the proximal mesh is hemispherical, bowl shaped, dome shaped, inverted dome shaped, inverted umbrella shaped, parabolic, paraboloid shaped, prolate hemisphere shaped, reflected parabola shaped, semi-circular, and/or umbrella shaped; wherein the proximal mesh centroid is a second distance from the aneurysm neck; wherein the second distance is less than the first distance; wherein the proximal mesh spans the aneurysm neck; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a distal (wire and/or polymer) mesh (or net or porous balloon) which is inserted into an aneurysm sac; wherein the distal mesh is hemispherical, bowl shaped, dome shaped, inverted dome shaped, inverted umbrella shaped, parabolic, paraboloid shaped, prolate hemisphere shaped, reflected parabola shaped, semi-circular, and/or umbrella shaped; wherein the distal mesh centroid is a first distance from the aneurysm neck; and a proximal mesh inserted into the aneurysm sac; wherein the proximal mesh centroid is a second distance from the aneurysm neck; wherein the second distance is less than the first distance; wherein the proximal mesh spans the aneurysm neck; and wherein the distal mesh and/or proximal mesh are filled with embolic material (such as microsponges, hydrogels, or coils).

An aneurysm occlusion device can comprise: a distal 3D-printed mesh inserted into an aneurysm sac; wherein the distal 3D-printed mesh centroid is a first distance from the aneurysm neck; and a proximal 3D-printed mesh inserted into the aneurysm sac; wherein the proximal polymer 3D-printed mesh is bowl shaped; wherein the proximal 3D-printed mesh centroid is a second distance from the aneurysm neck; wherein the second distance is less than the first distance; wherein the proximal 3D-printed mesh spans the aneurysm neck; wherein a portion of the distal 3D-printed mesh is within the concavity of the proximal 3D-printed mesh; wherein the proximal 3D-printed mesh is connected to the distal 3D-printed mesh; and wherein the distal 3D-printed mesh and/or proximal 3D-printed mesh are filled with embolic material (such as microsponges, hydrogels, or coils). An aneurysm occlusion device can comprise: a distal 3D-printed mesh inserted into an aneurysm sac; wherein the distal 3D-printed mesh centroid is a first distance from the aneurysm neck; and a proximal 3D-printed mesh inserted into the aneurysm sac; wherein the proximal polymer 3D-printed mesh is bowl shaped; wherein the proximal 3D-printed mesh centroid is a second distance from the aneurysm neck; wherein the second distance is less than the first distance; wherein the proximal 3D-printed mesh spans the aneurysm neck; wherein a portion of the distal 3D-printed mesh is within the concavity of the proximal 3D-printed mesh; and wherein the proximal 3D-printed mesh is connected to the distal 3D-printed mesh.

An aneurysm occlusion device can comprise: a distal mesh (or net or porous balloon) which is inserted into an aneurysm sac; wherein the distal mesh has is barrel shaped, apple shaped, hourglass shaped, peanut shaped, and/or pumpkin shaped; wherein the distal mesh centroid is a first distance from the aneurysm neck; and a bowl shaped proximal mesh inserted into the aneurysm sac; wherein the proximal mesh centroid is a second distance from the aneurysm neck; wherein the second distance is less than the first distance; wherein the proximal mesh spans the aneurysm neck; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a distal mesh (or net or porous balloon) which is inserted into an aneurysm sac; wherein the distal mesh is cardioid, crescent shaped, and/or kidney shaped; wherein the distal mesh centroid is a first distance from the aneurysm neck; and a bowl shaped proximal mesh inserted into the aneurysm sac; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: a distal mesh (or net or porous balloon) which is inserted into an aneurysm sac; wherein the distal mesh is concave; wherein the distal mesh centroid is a first distance from the aneurysm neck; and a proximal mesh inserted into the aneurysm sac; wherein the proximal mesh is hemispherical, bowl shaped, dome shaped, inverted dome shaped, inverted umbrella shaped, parabolic, paraboloid shaped, prolate hemisphere shaped, reflected parabola shaped, semi-circular, and/or umbrella shaped; wherein the proximal mesh centroid is a second distance from the aneurysm neck; wherein the second distance is less than the first distance; wherein the proximal mesh spans the aneurysm neck; wherein the proximal mesh is connected to the distal mesh; and wherein the distal mesh and/or proximal mesh are filled with embolic material (such as microsponges, hydrogels, or coils).

An aneurysm occlusion device can comprise: a distal mesh (or net or porous balloon) which is inserted into an aneurysm sac; wherein the distal mesh is convex; wherein the distal mesh centroid is a first distance from the aneurysm neck; and a proximal mesh inserted into the aneurysm sac; wherein the proximal mesh is hemispherical, bowl shaped, dome shaped, inverted dome shaped, inverted umbrella shaped, parabolic, paraboloid shaped, prolate hemisphere shaped, reflected parabola shaped, semi-circular, and/or umbrella shaped; wherein the proximal mesh centroid is a second distance from the aneurysm neck; wherein the second distance is less than the first distance; wherein the proximal mesh spans the aneurysm neck; wherein the proximal mesh is connected to the distal mesh; and wherein the distal mesh and/or proximal mesh are filled with embolic material (such as microsponges, hydrogels, or coils).

An aneurysm occlusion device can comprise: a distal mesh (or net or porous balloon) which is inserted into an aneurysm sac; wherein the distal mesh is ellipsoidal, compressed sphere shaped, elliptical, oblate spheroid shaped, oblong, oval shaped, and/or ovaloid; wherein the distal mesh centroid is a first distance from the aneurysm neck; and a proximal mesh inserted into the aneurysm sac; wherein the proximal mesh is hemispherical, bowl shaped, dome shaped, inverted dome shaped, inverted umbrella shaped, parabolic, paraboloid shaped, prolate hemisphere shaped, reflected parabola shaped, semi-circular, and/or umbrella shaped; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a distal mesh (or net or porous balloon) which is inserted into an aneurysm sac; wherein the distal mesh is generally ellipsoidal, egg shaped, or apple shaped; wherein the distal mesh has a first elasticity level; and a proximal mesh inserted into the aneurysm sac; wherein the proximal mesh is bowl or paraboloid shaped with a distal-facing concavity; wherein the proximal mesh has a second elasticity level which is less than the first elasticity level; wherein the proximal mesh spans the aneurysm neck; and wherein a portion of the distal mesh is within the concavity of the proximal mesh.

An aneurysm occlusion device can comprise: a distal mesh (or net or porous balloon) which is inserted into an aneurysm sac; wherein the distal mesh is generally ellipsoidal, egg shaped, or apple shaped; wherein the distal mesh has a first elasticity level; wherein the distal mesh centroid is a first distance from the aneurysm neck; and a proximal mesh inserted into the aneurysm sac; wherein the proximal mesh is bowl or paraboloid shaped with a distal-facing concavity; wherein the proximal mesh has a second elasticity level which is less than the first elasticity level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; and wherein the distal mesh and/or proximal mesh are filled with embolic material (such as microsponges, hydrogels, or coils). An aneurysm occlusion device can comprise: a distal mesh (or net or porous balloon) which is inserted into an aneurysm sac; wherein the distal mesh is globular and multi-lobed; wherein the distal mesh has a first elasticity level; wherein the distal mesh centroid is a first distance from the aneurysm neck; and a proximal (wire and/or polymer) mesh (or net or porous balloon) which is inserted into the aneurysm sac; wherein the proximal mesh is also globular and multi-lobed; wherein the proximal mesh has a second elasticity level which is less than the first elasticity level; wherein the proximal mesh centroid is a second distance from the aneurysm neck; wherein the second distance is less than the first distance; wherein the proximal mesh spans across the inside of the aneurysm neck; wherein the proximal mesh is (centrally) connected to the distal mesh; and wherein the distal mesh and/or proximal mesh are filled with embolic material (such as microsponges, hydrogels, or coils).

An aneurysm occlusion device can comprise: a distal mesh (or net or porous balloon) which is inserted into an aneurysm sac; wherein the distal mesh is globular and multi-lobed; wherein the distal mesh has a first elasticity level; wherein the distal mesh centroid is a first distance from the aneurysm neck; and a proximal (wire and/or polymer) mesh (or net or porous balloon) which is inserted into the aneurysm sac; wherein the proximal mesh is also globular and multi-lobed; wherein the proximal mesh has a second elasticity level which is less than the first elasticity level; wherein the proximal mesh centroid is a second distance from the aneurysm neck; wherein the second distance is less than the first distance; wherein the proximal mesh spans across the inside of the aneurysm neck; and wherein the proximal mesh is (centrally) connected to the distal mesh. An aneurysm occlusion device can comprise: a distal mesh (or net or porous balloon) which is inserted into an aneurysm sac; wherein the distal mesh is hemispherical, bowl shaped, dome shaped, inverted dome shaped, inverted umbrella shaped, parabolic, paraboloid shaped, prolate hemisphere shaped, reflected parabola shaped, semi-circular, and/or umbrella shaped; wherein the distal mesh centroid is a first distance from the aneurysm neck; and a proximal mesh inserted into the aneurysm sac; wherein the proximal mesh is hemispherical, bowl shaped, dome shaped, inverted dome shaped, inverted umbrella shaped, parabolic, paraboloid shaped, prolate hemisphere shaped, reflected parabola shaped, semi-circular, and/or umbrella shaped; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: a first (wire and/or polymer) mesh (or net or porous balloon) which is inserted into an aneurysm sac, wherein the distal mesh has a sinusoidal shape (such as a 3D shape created by rotating a sinusoidal curve), and wherein the distal mesh centroid is a first distance from the aneurysm neck; and a proximal mesh (such as a wire mesh) which is inserted into the aneurysm sac; wherein the proximal mesh is hemispherical, bowl shaped, dome shaped, inverted dome shaped, inverted umbrella shaped, parabolic, paraboloid shaped, prolate hemisphere shaped, reflected parabola shaped, semi-circular, and/or umbrella shaped; wherein the proximal mesh centroid is a second distance from the aneurysm neck; wherein the second distance is less than the first distance; wherein the proximal mesh spans the aneurysm neck; wherein the proximal mesh is (centrally) connected to the distal mesh. An aneurysm occlusion device can comprise: a first (wire and/or polymer) mesh (or net or porous balloon) which is inserted into an aneurysm sac; wherein the first mesh has a first level of elasticity; wherein the first mesh is sufficiently flexible to conform to the walls of even an irregularly-shaped aneurysm; wherein the first mesh is expanded by being filled with embolic material (such as microsponges, hydrogels, or coils); and a second mesh inserted into the aneurysm sac; wherein the second mesh encircles the first mesh; wherein the second mesh has a second level of elasticity which is less than the first level of elasticity.

An aneurysm occlusion device can comprise: a first (wire and/or polymer) mesh (or net or porous balloon) which is inserted into an aneurysm sac; wherein the first mesh has a first level of elasticity; wherein the first mesh is sufficiently flexible to conform to the walls of even an irregularly-shaped aneurysm; wherein the first mesh is expanded by being filled with embolic material (such as microsponges, hydrogels, or coils); and a second mesh inserted into the aneurysm sac; wherein the second mesh encircles the widest circumference of the first mesh; wherein the second mesh has a second level of elasticity which is less than the first level of elasticity.

An aneurysm occlusion device can comprise: a first mesh (or net or porous balloon) which is inserted into an aneurysm sac, wherein the distal mesh has a sinusoidal shape (such as a 3D shape created by rotating a sinusoidal curve), and wherein the distal mesh centroid is a first distance from the aneurysm neck; and a proximal mesh (such as a wire mesh) which is inserted into the aneurysm sac; wherein the proximal mesh is bowl shaped; wherein the proximal mesh centroid is a second distance from the aneurysm neck; wherein the second distance is less than the first distance; wherein the proximal mesh spans the aneurysm neck; wherein the proximal mesh is (centrally) connected to the distal mesh.

An aneurysm occlusion device can comprise: a first mesh (or net or porous balloon) which is inserted into an aneurysm sac; wherein the distal mesh has a sinusoidal shape; wherein the distal mesh has a first level of elasticity, modulus of elasticity, and/or Young's modulus; wherein the distal mesh centroid is a first distance from the aneurysm neck; and a disk or ellipsoidal shaped proximal mesh inserted into the aneurysm sac; wherein the proximal mesh has a second level of elasticity, modulus of elasticity, and/or Young's modulus which is less than the first level; wherein the proximal mesh centroid is a second distance from the aneurysm neck; wherein the second distance is less than the first distance; wherein the proximal mesh spans the aneurysm neck. An aneurysm occlusion device can comprise: a first mesh (or net or porous balloon) which is inserted into an aneurysm sac; wherein the first mesh has a first level of elasticity; wherein the first mesh is sufficiently flexible to conform to the walls of even an irregularly-shaped aneurysm; wherein the first mesh is expanded by being filled with embolic material; and a second mesh inserted into the aneurysm sac; wherein the second mesh encircles the middle of the first mesh; wherein the second mesh has a second level of elasticity which is less than the first level of elasticity.

An aneurysm occlusion device can comprise: a flexible irregularly shaped mesh (or net or porous balloon) which is inserted into an aneurysm sac; wherein the flexible irregularly shaped mesh has a first elasticity level; wherein the flexible irregularly shaped mesh (or net or porous balloon) centroid is a first distance from the aneurysm neck; and an ellipsoidal (wire) mesh inserted into the aneurysm sac; wherein the disk or ellipsoidal shaped mesh has a second elasticity level which is less than the first elasticity level; wherein the disk or ellipsoidal shaped mesh centroid is a second distance from the aneurysm neck; wherein the second distance is less than the first distance; wherein the disk or ellipsoidal shaped mesh spans the aneurysm neck; and wherein the disk or ellipsoidal shaped mesh is nested within the flexible irregularly shaped wire mesh. An aneurysm occlusion device can comprise: a flexible irregularly shaped mesh (or net or porous balloon) which is inserted into an aneurysm sac; wherein the flexible irregularly shaped mesh has a first elasticity level; wherein the flexible irregularly shaped mesh (or net or porous balloon) centroid is a first distance from the aneurysm neck; and an ellipsoidal (wire) mesh inserted into the aneurysm sac; wherein the disk or ellipsoidal shaped mesh has a second elasticity level which is less than the first elasticity level; wherein the disk or ellipsoidal shaped mesh centroid is a second distance from the aneurysm neck; wherein the second distance is less than the first distance; wherein the disk or ellipsoidal shaped mesh spans the aneurysm neck; and wherein the flexible irregularly shaped mesh and/or the disk or ellipsoidal shaped mesh are filled with embolic material (such as microsponges, hydrogels, or coils).

An aneurysm occlusion device can comprise: a frustum shaped distal (wire and/or polymer) mesh inserted into an aneurysm sac; wherein the distal mesh has a first level of elasticity, modulus of elasticity, and/or Young's modulus; wherein the distal mesh centroid is a first distance from the aneurysm neck; and a bowl shaped proximal mesh inserted into the aneurysm sac; wherein the proximal mesh has a second level of elasticity, modulus of elasticity, and/or Young's modulus which is less than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a frustum shaped distal mesh inserted into an aneurysm sac; wherein the distal mesh has a first elasticity level; wherein the distal mesh centroid is a first distance from the aneurysm neck; and a bowl shaped proximal mesh inserted into the aneurysm sac; wherein the proximal mesh has a second elasticity level which is less than the first elasticity level; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils).

An aneurysm occlusion device can comprise: a generally spherical (wire and/or polymer) mesh (or net or porous balloon) which is inserted into an aneurysm sac; wherein the generally spherical mesh (or net or porous balloon) centroid is a first distance from the aneurysm neck; and an ellipsoidal (wire) mesh inserted into the aneurysm sac; wherein the disk or ellipsoidal shaped mesh centroid is a second distance from the aneurysm neck; wherein the second distance is less than the first distance; wherein the disk or ellipsoidal shaped mesh spans the aneurysm neck; and wherein the disk or ellipsoidal shaped mesh is (centrally) connected to the generally spherical mesh. An aneurysm occlusion device can comprise: a generally spherical (wire and/or polymer) mesh (or net or porous balloon) which is inserted into an aneurysm sac; wherein the generally spherical mesh centroid is a first distance from the aneurysm neck; and an ellipsoidal (wire) mesh inserted into the aneurysm sac; wherein the disk or ellipsoidal shaped mesh centroid is a second distance from the aneurysm neck; wherein the second distance is less than the first distance; wherein the disk or ellipsoidal shaped mesh spans the aneurysm neck; and wherein the disk or ellipsoidal shaped mesh is nested within a proximal portion of the generally spherical wire mesh.

An aneurysm occlusion device can comprise: a generally spherical (wire and/or polymer) mesh (or net or porous balloon) which is inserted into an aneurysm sac; wherein the generally spherical mesh centroid is a first distance from the aneurysm neck; and an ellipsoidal (wire) mesh inserted into the aneurysm sac; wherein the disk or ellipsoidal shaped mesh centroid is a second distance from the aneurysm neck; wherein the second distance is less than the first distance; wherein the disk or ellipsoidal shaped mesh spans the aneurysm neck; and wherein the ellipsoidal (wire) mesh is (centrally) connected to the generally spherical wire mesh.

An aneurysm occlusion device can comprise: a generally spherical (wire and/or polymer) mesh (or net or porous balloon) which is inserted into an aneurysm sac; wherein the generally spherical mesh centroid is a first distance from the aneurysm neck; and an ellipsoidal (wire) mesh inserted into the aneurysm sac; wherein the disk or ellipsoidal shaped mesh centroid is a second distance from the aneurysm neck; wherein the second distance is less than the first distance; wherein the disk or ellipsoidal shaped mesh spans the aneurysm neck; wherein the disk or ellipsoidal shaped mesh is (centrally) connected to the generally spherical mesh; and wherein the generally spherical mesh and/or the disk or ellipsoidal shaped mesh are filled with embolic material (such as microsponges, hydrogels, or coils).

An aneurysm occlusion device can comprise: a generally spherical (wire and/or polymer) mesh (or net or porous balloon) which is inserted into an aneurysm sac; wherein the generally spherical mesh has a first elasticity level; and a ring-shaped (wire) mesh inserted into the aneurysm sac; wherein the ring-shaped mesh spans the circumference the spherical mesh (either inside or outside the mesh); and wherein the ring-shaped mesh has a second elasticity level which is less than the first elasticity level. An aneurysm occlusion device can comprise: a generally spherical mesh (or net or porous balloon) which is inserted into an aneurysm sac; wherein the generally spherical mesh (or net or porous balloon) centroid is a first distance from the aneurysm neck; and an ellipsoidal (wire) mesh inserted into the aneurysm sac; wherein the disk or ellipsoidal shaped mesh centroid is a second distance from the aneurysm neck; wherein the second distance is less than the first distance; wherein the disk or ellipsoidal shaped mesh spans the aneurysm neck; and wherein the disk or ellipsoidal shaped mesh is nested within the generally spherical mesh.

An aneurysm occlusion device can comprise: a generally spherical mesh (or net or porous balloon) which is inserted into an aneurysm sac; wherein the generally spherical mesh centroid is a first distance from the aneurysm neck; and an ellipsoidal (wire) mesh inserted into the aneurysm sac; wherein the disk or ellipsoidal shaped mesh centroid is a second distance from the aneurysm neck; wherein the second distance is less than the first distance; wherein the disk or ellipsoidal shaped mesh spans the aneurysm neck; and wherein the disk or ellipsoidal shaped mesh is (centrally) connected to the generally spherical mesh. An aneurysm occlusion device can comprise: a generally spherical mesh (or net or porous balloon) which is inserted into an aneurysm sac; wherein the generally spherical mesh has a first elasticity level; and a ring-shaped (wire) mesh inserted into the aneurysm sac; wherein the ring-shaped mesh spans the circumference the spherical mesh (either inside or outside the mesh); wherein the ring-shaped mesh has a second elasticity level which is less than the first elasticity level; and wherein the generally spherical mesh is filled with embolic material (such as microsponges, hydrogels, or coils).

An aneurysm occlusion device can comprise: a generally spherical non-uniform surface (wire and/or polymer) mesh (or net or porous balloon) which is inserted into an aneurysm sac; wherein the mesh further comprises a distal portion; wherein the distal portion has a first density and a proximal portion; wherein the proximal portion has a second density which is greater than the first density; wherein the proximal portion spans the aneurysm neck; and wherein the mesh is filled with embolic material (such as microsponges, hydrogels, or coils). An aneurysm occlusion device can comprise: a generally spherical non-uniform surface (wire and/or polymer) mesh (or net or porous balloon) which is inserted into an aneurysm sac; wherein the mesh further comprises a distal portion; wherein the distal portion has a first flexibility level and a proximal portion which spans the aneurysm neck, wherein the proximal portion has a second flexibility level which is less than the first flexibility level; and wherein the mesh is filled with embolic material (such as microsponges, hydrogels, or coils).

An aneurysm occlusion device can comprise: a generally spherical non-uniform surface (wire and/or polymer) mesh (or net or porous balloon) which is inserted into an aneurysm sac; wherein the mesh further comprises a distal portion; wherein the distal portion has a first mesh density and a proximal portion which spans the aneurysm neck, wherein the proximal portion has a second mesh density which is greater than the first mesh density; and wherein the proximal portion spans the aneurysm neck. An aneurysm occlusion device can comprise: a generally spherical non-uniform surface (wire and/or polymer) mesh (or net or porous balloon) which is inserted into an aneurysm sac; wherein the mesh further comprises a distal portion and a proximal portion with less flexibility than the first portion; and wherein the proximal portion spans the aneurysm neck; and wherein the mesh is filled with embolic material (such as microsponges, hydrogels, or coils). An aneurysm occlusion device can comprise: a generally spherical non-uniform surface mesh (or net or porous balloon) which is inserted into an aneurysm sac; wherein the mesh further comprises a distal portion; wherein the distal portion has a first flexibility level and a proximal portion which spans the aneurysm neck, wherein the proximal portion has a second flexibility level which is less than the first flexibility level; and wherein the proximal portion spans the aneurysm neck.

An aneurysm occlusion device can comprise: a generally spherical non-uniform surface mesh (or net or porous balloon) which is inserted into an aneurysm sac; wherein the mesh further comprises a distal portion; wherein the distal portion has a first porosity level and a proximal portion which spans the aneurysm neck, wherein the proximal portion has a second porosity level which is less than the first porosity level; and wherein the proximal portion spans the aneurysm neck. An aneurysm occlusion device can comprise: a generally spherical non-uniform surface mesh (or net or porous balloon) which is inserted into an aneurysm sac; wherein the mesh further comprises a distal portion and a proximal portion with a lower porosity level than the distal portion; wherein the proximal portion spans the aneurysm neck; and wherein the mesh is filled with embolic material (such as microsponges, hydrogels, or coils).

An aneurysm occlusion device can comprise: a generally spherical non-uniform surface mesh inserted into an aneurysm sac; wherein the mesh further comprises a distal portion and a proximal portion with less flexibility than the first portion; and wherein the proximal portion spans the aneurysm neck. An aneurysm occlusion device can comprise: a generally spherical non-uniform surface porous balloon which is inserted into an aneurysm sac; wherein the non-uniform porous balloon further comprises a distal portion; wherein the distal portion has a first flexibility level; and wherein the non-uniform porous balloon further comprises a proximal portion which spans the aneurysm neck, wherein the proximal portion has a second flexibility level which is less than the first flexibility level; and wherein the mesh is filled with embolic material (such as microsponges, hydrogels, or coils).

An aneurysm occlusion device can comprise: a generally spherical non-uniform surface wire mesh inserted into an aneurysm sac; wherein the mesh further comprises a distal portion; wherein the distal portion has a first flexibility level and a proximal portion which spans the aneurysm neck, wherein the proximal portion has a second flexibility level which is less than the first flexibility level; and wherein the mesh is filled with embolic material (such as microsponges, hydrogels, or coils). An aneurysm occlusion device can comprise: a generally spherical non-uniform surface wire mesh inserted into an aneurysm sac; wherein the mesh further comprises a distal portion; wherein the distal portion has a first mesh density and a proximal portion which spans the aneurysm neck, wherein the proximal portion has a second mesh density which is greater than the first mesh density; and wherein the proximal portion spans the aneurysm neck.

An aneurysm occlusion device can comprise: a generally-spherical distal (wire and/or polymer) mesh (or net or porous balloon) which is inserted into an aneurysm sac; and a proximal mesh (or net or porous balloon) which is inserted into the aneurysm sac; wherein the proximal mesh is also generally spherical; wherein the second distance is less than the first distance; wherein the proximal mesh spans across the inside of the aneurysm neck; wherein the proximal mesh is centrally connected to the distal mesh; and wherein the distal mesh and/or proximal mesh are filled with embolic material (such as microsponges, hydrogels, or coils). An aneurysm occlusion device can comprise: a generally-spherical distal (wire and/or polymer) mesh (or net or porous balloon) which is inserted into an aneurysm sac; and a proximal mesh (or net or porous balloon) which is inserted into the aneurysm sac; wherein the proximal mesh is also generally spherical; wherein the second distance is less than the first distance; wherein the proximal mesh spans across the inside of the aneurysm neck; and wherein the proximal mesh is centrally connected to the distal mesh.

An aneurysm occlusion device can comprise: a generally-spherical distal (wire and/or polymer) mesh (or net or porous balloon) which is inserted into an aneurysm sac; wherein the distal mesh centroid is a first distance from the aneurysm neck; and a disk or ellipsoidal shaped proximal mesh inserted into the aneurysm sac; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils). An aneurysm occlusion device can comprise: a generally-spherical distal (wire and/or polymer) mesh (or net or porous balloon) which is inserted into an aneurysm sac; wherein the distal mesh centroid is a first distance from the aneurysm neck; and a proximal mesh (or net or porous balloon) which is inserted into the aneurysm sac; wherein the proximal mesh is also generally spherical; wherein the proximal mesh centroid is a second distance from the aneurysm neck; wherein the second distance is less than the first distance; wherein the proximal mesh spans across the inside of the aneurysm neck; wherein the proximal mesh is (centrally) connected to the distal mesh; and wherein the distal mesh and/or proximal mesh are filled with embolic material (such as microsponges, hydrogels, or coils).

An aneurysm occlusion device can comprise: a generally-spherical distal (wire and/or polymer) mesh (or net or porous balloon) which is inserted into an aneurysm sac; wherein the distal mesh centroid is a first distance from the aneurysm neck; and a proximal mesh (or net or porous balloon) which is inserted into the aneurysm sac; wherein the proximal mesh is also generally spherical; wherein the proximal mesh centroid is a second distance from the aneurysm neck; wherein the second distance is less than the first distance; wherein the proximal mesh spans across the inside of the aneurysm neck; and wherein the proximal mesh is (centrally) connected to the distal mesh. An aneurysm occlusion device can comprise: a generally-spherical distal (wire and/or polymer) mesh (or net or porous balloon) which is inserted into an aneurysm sac; wherein the distal mesh has a first flexibility level; wherein the distal mesh centroid is a first distance from the aneurysm neck; and a generally spherical proximal mesh inserted into the aneurysm sac; wherein the proximal mesh has a second flexibility level which is less than the first level; wherein the proximal mesh centroid is a second distance from the aneurysm neck; wherein the second distance is less than the first distance; wherein the proximal mesh spans the aneurysm neck; wherein the proximal mesh is connected and axially-aligned with the distal mesh; and wherein the distal mesh and/or proximal mesh are filled with embolic material (such as microsponges, hydrogels, or coils).

An aneurysm occlusion device can comprise: a generally-spherical distal (wire and/or polymer) mesh (or net or porous balloon) which is inserted into an aneurysm sac; wherein the distal mesh has a first level of compliance and/or compressibility; wherein the distal mesh centroid is a first distance from the aneurysm neck; and a disk or ellipsoidal shaped proximal mesh inserted into the aneurysm sac; wherein the proximal mesh has a second level of compliance and/or compressibility which is less than the first level; wherein the proximal mesh centroid is a second distance from the aneurysm neck; wherein the second distance is less than the first distance; wherein the proximal mesh spans the aneurysm neck; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: a generally-spherical distal (wire and/or polymer) mesh (or net or porous balloon) which is inserted into an aneurysm sac; wherein the distal mesh has a first level of conformability, deformable, malleability, and/or plasticity; wherein the distal mesh centroid is a first distance from the aneurysm neck; and a disk or ellipsoidal shaped proximal mesh inserted into the aneurysm sac; wherein the proximal mesh has a second level of conformability, deformable, malleability, and/or plasticity which is less than the first level; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils).

An aneurysm occlusion device can comprise: a generally-spherical distal (wire and/or polymer) mesh (or net or porous balloon) which is inserted into an aneurysm sac; wherein the distal mesh has a first level of elasticity, flexibility, porosity, stiffness, or thickness; wherein the distal mesh centroid is a first distance from the aneurysm neck; and a bowl shaped proximal mesh inserted into the aneurysm sac; wherein the proximal mesh has a second level of elasticity, flexibility, porosity, stiffness, or thickness; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a generally-spherical distal (wire and/or polymer) mesh (or net or porous balloon) which is inserted into an aneurysm sac; wherein the distal mesh has a first level of flexibility, Flexural modulus, and/or bendability; wherein the distal mesh centroid is a first distance from the aneurysm neck; and a bowl shaped proximal mesh inserted into the aneurysm sac; wherein the proximal mesh has a second level of flexibility, Flexural modulus, and/or bendability which is less than the first level; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils).

An aneurysm occlusion device can comprise: a generally-spherical distal (wire and/or polymer) mesh (or net or porous balloon) which is inserted into an aneurysm sac; wherein the distal mesh has a first level of radial compliance, compressibility, and/or stiffness; wherein the distal mesh centroid is a first distance from the aneurysm neck; and a bowl shaped proximal mesh inserted into the aneurysm sac; wherein the proximal mesh has a second level of radial compliance, compressibility, and/or stiffness which is greater than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a generally-spherical distal (wire and/or polymer) mesh (or net or porous balloon) which is inserted into an aneurysm sac; wherein the distal mesh has a first thickness; wherein the distal mesh centroid is a first distance from the aneurysm neck; and a bowl shaped proximal mesh with a second thickness which is inserted into the aneurysm sac; wherein the second thickness is greater than the first thickness; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: a generally-spherical distal mesh (or net or porous balloon) which is inserted into an aneurysm sac; wherein the distal mesh centroid is a first distance from the aneurysm neck; and a disk or ellipsoidal shaped proximal mesh inserted into the aneurysm sac; wherein the proximal mesh centroid is a second distance from the aneurysm neck; wherein the second distance is less than the first distance; wherein the proximal mesh spans the aneurysm neck; wherein the proximal mesh is connected to the distal mesh; and wherein the proximal mesh is axially-aligned with the distal mesh. An aneurysm occlusion device can comprise: a generally-spherical distal mesh (or net or porous balloon) which is inserted into an aneurysm sac; wherein the distal mesh has a first flexibility level; wherein the distal mesh centroid is a first distance from the aneurysm neck; and a generally spherical proximal mesh inserted into the aneurysm sac; wherein the proximal mesh has a second flexibility level which is less than the first level; wherein the proximal mesh centroid is a second distance from the aneurysm neck; wherein the second distance is less than the first distance; wherein the proximal mesh spans the aneurysm neck; and wherein the proximal mesh is connected and axially-aligned with the distal mesh.

An aneurysm occlusion device can comprise: a generally-spherical distal mesh (or net or porous balloon) which is inserted into an aneurysm sac; wherein the distal mesh has a first level of compliance and/or compressibility; wherein the distal mesh centroid is a first distance from the aneurysm neck; and a generally spherical proximal mesh inserted into the aneurysm sac; wherein the proximal mesh has a second level of compliance and/or compressibility which is less than the first level; wherein the proximal mesh centroid is a second distance from the aneurysm neck; wherein the second distance is less than the first distance; wherein the proximal mesh spans the aneurysm neck; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a generally-spherical distal mesh (or net or porous balloon) which is inserted into an aneurysm sac; wherein the distal mesh has a first level of elasticity, modulus of elasticity, and/or Young's modulus; and a proximal mesh inserted into the aneurysm sac; wherein the proximal mesh is ring shaped;

wherein the proximal mesh has a second level of elasticity, modulus of elasticity, and/or Young's modulus which is less than the first level; wherein the proximal mesh encircles the distal mesh; and wherein the distal mesh and/or proximal mesh are filled with embolic material (such as microsponges, hydrogels, or coils).

An aneurysm occlusion device can comprise: a generally-spherical distal mesh (or net or porous balloon) which is inserted into an aneurysm sac; wherein the distal mesh has a first level of porosity; wherein the distal mesh centroid is a first distance from the aneurysm neck; and a disk or ellipsoidal shaped proximal mesh inserted into the aneurysm sac; wherein the proximal mesh has a second level of porosity which is less than the first level; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils).

An aneurysm occlusion device can comprise: a generally-spherical distal mesh (or net or porous balloon) which is inserted into an aneurysm sac; wherein the distal mesh has a first level of stiffness, rigidity, and/or resiliency; wherein the distal mesh centroid is a first distance from the aneurysm neck; and a bowl shaped proximal mesh inserted into the aneurysm sac; wherein the proximal mesh has a second level of stiffness, rigidity, and/or resiliency which is greater than the first level; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils).

An aneurysm occlusion device can comprise: a generally-spherical non-uniform surface polymer mesh (or net) which is inserted into an aneurysm sac; wherein the mesh or net further comprises a distal portion; wherein the distal portion has a first flexibility level; and wherein the mesh or net further comprises a proximal portion which spans the aneurysm neck, wherein the proximal portion has a second flexibility level which is less than the first flexibility level; and wherein the mesh is filled with embolic material (such as microsponges, hydrogels, or coils). An aneurysm occlusion device can comprise: a non-uniform surface (wire and/or polymer) mesh (or net or porous balloon) which is inserted into an aneurysm sac, wherein the mesh is bowl shaped; wherein the mesh further comprises a distal portion; wherein the distal portion has a first flexibility level and a proximal portion which spans the aneurysm neck, wherein the proximal portion has a second flexibility level which is less than the first flexibility level; and wherein the mesh is filled with embolic material (such as microsponges, hydrogels, or coils).

An aneurysm occlusion device can comprise: a non-uniform surface (wire and/or polymer) mesh (or net or porous balloon) which is inserted into an aneurysm sac, wherein the mesh has an irregular (3D-printed) shape; wherein the mesh further comprises a distal portion with a first elasticity level and a proximal portion which spans the aneurysm neck; and wherein the proximal portion has a second elasticity level which is less than the first elasticity level. An aneurysm occlusion device can comprise: a non-uniform surface (wire and/or polymer) mesh (or net or porous balloon) which is inserted into an aneurysm sac, wherein the mesh is peanut or hourglass shaped; wherein the mesh further comprises a distal portion with a first elasticity level and a proximal portion; wherein the proximal portion has a second elasticity level which is less than the first elasticity level; wherein the proximal portion spans the aneurysm neck; and wherein the mesh is filled with embolic material (such as microsponges, hydrogels, or coils).

An aneurysm occlusion device can comprise: a non-uniform surface (wire and/or polymer) mesh (or net or porous balloon) which is inserted into an aneurysm sac, wherein the mesh is ellipsoidal; wherein the mesh further comprises a distal portion with a first elasticity level and a proximal portion; wherein the proximal portion has a second elasticity level which is less than the first elasticity level; wherein the proximal portion spans the aneurysm neck; and wherein the mesh is filled with embolic material (such as microsponges, hydrogels, or coils). An aneurysm occlusion device can comprise: a non-uniform surface (wire and/or polymer) mesh (or net or porous balloon) which is inserted into an aneurysm sac, wherein the mesh is apple or barrel shaped; wherein the mesh further comprises a distal portion with a first elasticity level and a proximal portion; wherein the proximal portion has a second elasticity level which is less than the first elasticity level; wherein the proximal portion spans the aneurysm neck; and wherein the mesh is filled with embolic material (such as microsponges, hydrogels, or coils).

An aneurysm occlusion device can comprise: a non-uniform surface (wire and/or polymer) mesh (or net or porous balloon) which is inserted into an aneurysm sac, wherein the mesh is sinusoidal shaped; wherein the mesh further comprises a distal portion with a first elasticity level and a proximal portion; wherein the proximal portion has a second elasticity level which is less than the first elasticity level; wherein the proximal portion spans the aneurysm neck; and wherein the mesh is filled with embolic material (such as microsponges, hydrogels, or coils). An aneurysm occlusion device can comprise: a non-uniform surface elastomeric polymer mesh inserted into an aneurysm sac, wherein the mesh is generally spherical; wherein the mesh further comprises a distal portion; wherein the distal portion has a first mesh density and a proximal portion which spans the aneurysm neck, wherein the proximal portion has a second mesh density which is greater than the first mesh density; wherein the proximal portion spans the aneurysm neck; and; and wherein the mesh is filled with embolic material (such as microsponges, hydrogels, or coils).

An aneurysm occlusion device can comprise: a non-uniform surface mesh (or net or porous balloon) which is inserted into an aneurysm sac, wherein the mesh has an irregular (3D-printed) shape; wherein the mesh further comprises a distal portion with a first elasticity level and a proximal portion which spans the aneurysm neck, wherein the proximal portion has a second elasticity level which is less than the first elasticity level; and; and wherein the mesh is filled with embolic material (such as microsponges, hydrogels, or coils). An aneurysm occlusion device can comprise: a non-uniform surface mesh (or net or porous balloon) which is inserted into an aneurysm sac, wherein the mesh has an irregular (3D-printed) shape; wherein the mesh further comprises a distal portion with a first elasticity level and a proximal portion; wherein the proximal portion has a second elasticity level which is less than the first elasticity level; wherein the proximal portion spans the aneurysm neck; and wherein the mesh is filled with embolic material (such as microsponges, hydrogels, or coils).

An aneurysm occlusion device can comprise: a non-uniform surface mesh (or net or porous balloon) which is inserted into an aneurysm sac, wherein the mesh is multi-lobed; wherein the mesh further comprises a distal portion with a first elasticity level and a proximal portion; wherein the proximal portion has a second elasticity level which is less than the first elasticity level; wherein the proximal portion spans the aneurysm neck; and wherein the mesh is filled with embolic material (such as microsponges, hydrogels, or coils). An aneurysm occlusion device can comprise: a non-uniform surface mesh (or net or porous balloon) which is inserted into an aneurysm sac, wherein the mesh is barrel shaped; wherein the mesh further comprises a distal portion with a first elasticity level and a proximal portion; wherein the proximal portion has a second elasticity level which is less than the first elasticity level; wherein the proximal portion spans the aneurysm neck; and wherein the mesh is filled with embolic material (such as microsponges, hydrogels, or coils).

An aneurysm occlusion device can comprise: a non-uniform surface mesh inserted into an aneurysm sac, wherein the mesh is ellipsoidal; wherein the mesh further comprises a distal portion with a first elasticity level and a proximal portion; wherein the proximal portion has a second elasticity level which is less than the first elasticity level; wherein the proximal portion spans the aneurysm neck. An aneurysm occlusion device can comprise: a peanut or hourglass shaped distal (wire and/or polymer) mesh inserted into an aneurysm sac; wherein the distal mesh centroid is a first distance from the aneurysm neck; and a bowl shaped proximal mesh inserted into the aneurysm sac; wherein the proximal mesh centroid is a second distance from the aneurysm neck; wherein the second distance is less than the first distance; wherein the proximal mesh spans the aneurysm neck; and wherein the proximal mesh is connected to the distal mesh.

An aneurysm occlusion device can comprise: a peanut or hourglass shaped distal (wire and/or polymer) mesh inserted into an aneurysm sac; wherein the distal mesh has a first level of compliance and/or compressibility; wherein the distal mesh centroid is a first distance from the aneurysm neck; and a bowl shaped proximal mesh inserted into the aneurysm sac; wherein the proximal mesh has a second level of compliance and/or compressibility which is greater than the first level; wherein the proximal mesh centroid is a second distance from the aneurysm neck; wherein the second distance is less than the first distance; wherein the proximal mesh spans the aneurysm neck; and wherein the proximal mesh is connected to the distal mesh. An aneurysm occlusion device can comprise: a peanut or hourglass shaped distal (wire and/or polymer) mesh inserted into an aneurysm sac; wherein the distal mesh has a first level of porosity; wherein the distal mesh centroid is a first distance from the aneurysm neck; and a bowl shaped proximal mesh inserted into the aneurysm sac; wherein the proximal mesh has a second level of porosity which is less than the first level; wherein the proximal mesh centroid is a second distance from the aneurysm neck; wherein the second distance is less than the first distance; wherein the proximal mesh spans the aneurysm neck; and wherein the proximal mesh is connected to the distal mesh.

An aneurysm occlusion device can comprise: a peanut or hourglass shaped distal (wire and/or polymer) mesh inserted into an aneurysm sac; wherein the distal mesh has a first level of stretchability and/or ductility; wherein the distal mesh centroid is a first distance from the aneurysm neck; and a bowl shaped proximal mesh inserted into the aneurysm sac; wherein the proximal mesh has a second level of stretchability and/or ductility which is less than the first level; wherein the proximal mesh centroid is a second distance from the aneurysm neck; wherein the second distance is less than the first distance; wherein the proximal mesh spans the aneurysm neck; and wherein the proximal mesh is connected to the distal mesh. An aneurysm occlusion device can comprise: a peanut or hourglass shaped distal (wire and/or polymer) mesh inserted into an aneurysm sac; wherein the distal mesh has a first level of tensile strength; wherein the distal mesh centroid is a first distance from the aneurysm neck; and a bowl shaped proximal mesh inserted into the aneurysm sac; wherein the proximal mesh has a second level of tensile strength which is greater than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; and wherein the proximal mesh is connected to the distal mesh.

An aneurysm occlusion device can comprise: a peanut or hourglass shaped distal mesh inserted into an aneurysm sac; wherein the distal mesh has a first flexibility level; wherein the distal mesh centroid is a first distance from the aneurysm neck; and a bowl shaped proximal mesh inserted into the aneurysm sac; wherein the proximal mesh has a second flexibility level which is less than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; and wherein the proximal mesh is connected to the distal mesh.

An aneurysm occlusion device can comprise: a peanut or hourglass shaped distal mesh inserted into an aneurysm sac; wherein the distal mesh has a first level of conformability, deformable, malleability, and/or plasticity; wherein the distal mesh centroid is a first distance from the aneurysm neck; and a bowl shaped proximal mesh inserted into the aneurysm sac; wherein the proximal mesh has a second level of conformability, deformable, malleability, and/or plasticity which is less than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; and wherein the proximal mesh is connected to the distal mesh. An aneurysm occlusion device can comprise: a peanut or hourglass shaped distal mesh inserted into an aneurysm sac; wherein the distal mesh has a first level of softness, durometer, and/or hardness; wherein the distal mesh centroid is a first distance from the aneurysm neck; and a bowl shaped proximal mesh inserted into the aneurysm sac; wherein the proximal mesh has a second level of softness, durometer, and/or hardness; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; and wherein the proximal mesh is connected to the distal mesh.

An aneurysm occlusion device can comprise: a peanut or hourglass shaped distal mesh inserted into an aneurysm sac; wherein the distal mesh has a first porosity level; wherein the distal mesh centroid is a first distance from the aneurysm neck; and a bowl shaped proximal mesh inserted into the aneurysm sac; wherein the proximal mesh has a second porosity level which is less than the first level; wherein the proximal mesh centroid is a second distance from the aneurysm neck; wherein the second distance is less than the first distance; wherein the proximal mesh spans the aneurysm neck; and wherein the proximal mesh is connected to the distal mesh. An aneurysm occlusion device can comprise: a porous balloon which is inserted into an aneurysm sac and filled with embolic material; and a wire mesh inserted into the aneurysm sac; wherein the wire mesh has a bowl, parabola, hemisphere, or inverted-umbrella shape with a distal-facing concavity; wherein the wire mesh spans the aneurysm neck; and wherein a portion of the porous balloon is within the concavity of the proximal wire mesh.

An aneurysm occlusion device can comprise: an apple or barrel shaped distal (wire and/or polymer) mesh inserted into an aneurysm sac; wherein the distal mesh centroid is a first distance from the aneurysm neck; and a proximal mesh inserted into the aneurysm sac; wherein the proximal mesh is hemispherical, bowl shaped, dome shaped, inverted dome shaped, inverted umbrella shaped, parabolic, paraboloid shaped, prolate hemisphere shaped, reflected parabola shaped, semi-circular, and/or umbrella shaped; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: an apple or barrel shaped distal (wire and/or polymer) mesh inserted into an aneurysm sac; wherein the distal mesh has a first level of compliance and/or compressibility; wherein the distal mesh centroid is a first distance from the aneurysm neck; and a bowl shaped proximal mesh inserted into the aneurysm sac; wherein the proximal mesh has a second level of compliance and/or compressibility which is greater than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: an apple or barrel shaped distal (wire and/or polymer) mesh inserted into an aneurysm sac; wherein the distal mesh has a first level of porosity; wherein the distal mesh centroid is a first distance from the aneurysm neck; and a bowl shaped proximal mesh inserted into the aneurysm sac; wherein the proximal mesh has a second level of porosity which is less than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: an apple or barrel shaped distal (wire and/or polymer) mesh inserted into an aneurysm sac; wherein the distal mesh has a first level of stretchability and/or ductility; wherein the distal mesh centroid is a first distance from the aneurysm neck; and a bowl shaped proximal mesh inserted into the aneurysm sac; wherein the proximal mesh has a second level of stretchability and/or ductility which is less than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: an apple or barrel shaped distal (wire and/or polymer) mesh inserted into an aneurysm sac; wherein the distal mesh has a first level of tensile strength; wherein the distal mesh centroid is a first distance from the aneurysm neck; and a bowl shaped proximal mesh inserted into the aneurysm sac; wherein the proximal mesh has a second level of tensile strength which is greater than the first level; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils). An aneurysm occlusion device can comprise: an apple or barrel shaped distal mesh inserted into an aneurysm sac; wherein the distal mesh centroid is a first distance from the aneurysm neck; and a bowl shaped proximal mesh inserted into the aneurysm sac; wherein the proximal mesh centroid is a second distance from the aneurysm neck; wherein the second distance is less than the first distance; wherein the proximal mesh spans the aneurysm neck; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: an apple or barrel shaped distal mesh inserted into an aneurysm sac; wherein the distal mesh has a first flexibility level; wherein the distal mesh centroid is a first distance from the aneurysm neck; and a bowl shaped proximal mesh inserted into the aneurysm sac; wherein the proximal mesh has a second flexibility level which is less than the first level; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils). An aneurysm occlusion device can comprise: an apple or barrel shaped distal mesh inserted into an aneurysm sac; wherein the distal mesh has a first level of conformability, deformable, malleability, and/or plasticity; wherein the distal mesh centroid is a first distance from the aneurysm neck; and a bowl shaped proximal mesh inserted into the aneurysm sac; wherein the proximal mesh has a second level of conformability, deformable, malleability, and/or plasticity which is less than the first level; wherein the proximal mesh centroid is a second distance from the aneurysm neck; wherein the second distance is less than the first distance; wherein the proximal mesh spans the aneurysm neck; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: an apple or barrel shaped distal mesh inserted into an aneurysm sac; wherein the distal mesh has a first level of softness, durometer, and/or hardness; wherein the distal mesh centroid is a first distance from the aneurysm neck; and a bowl shaped proximal mesh inserted into the aneurysm sac; wherein the proximal mesh has a second level of softness, durometer, and/or hardness; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils). An aneurysm occlusion device can comprise: an apple or barrel shaped distal mesh inserted into an aneurysm sac; wherein the distal mesh has a first porosity level; wherein the distal mesh centroid is a first distance from the aneurysm neck; and a bowl shaped proximal mesh inserted into the aneurysm sac; wherein the proximal mesh has a second porosity level which is less than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: an egg-shaped distal (wire and/or polymer) mesh inserted into an aneurysm sac; wherein the distal mesh has a first elasticity level; wherein the distal mesh centroid is a first distance from the aneurysm neck; and a bowl shaped proximal mesh inserted into the aneurysm sac; wherein the proximal mesh has a second elasticity level which is less than the first elasticity level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: an egg-shaped distal (wire and/or polymer) mesh inserted into an aneurysm sac; wherein the distal mesh has a first level of elasticity, modulus of elasticity, and/or Young's modulus; wherein the distal mesh centroid is a first distance from the aneurysm neck; and a bowl shaped proximal mesh inserted into the aneurysm sac; wherein the proximal mesh has a second level of elasticity, modulus of elasticity, and/or Young's modulus which is less than the first level; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils).

An aneurysm occlusion device can comprise: an elastomeric balloon with holes in it which is inserted into an aneurysm sac and filled with embolic material (such as microsponges, hydrogels, or coils); and a wire mesh inserted into the aneurysm sac; wherein the wire mesh has a bowl, parabola, hemisphere, or inverted-umbrella shape with a distal-facing concavity; wherein the wire mesh spans the aneurysm neck; and wherein a portion of the porous balloon is within the concavity of the proximal wire mesh. An aneurysm occlusion device can comprise: an ellipsoidal, egg shape, or apple shaped generally spherical polymer and metal mesh inserted into an aneurysm sac; wherein the distal mesh has a first ratio of polymer material to metal material; and a bowl-shaped polymer and metal mesh inserted into the aneurysm sac; wherein the proximal mesh has a second ratio of polymer material to metal material which is less than the first ratio; wherein the bowl-shaped mesh spans the aneurysm; and wherein the distal mesh and/or the proximal mesh are filled with embolic material (such as microsponges, hydrogels, or coils).

An aneurysm occlusion device can comprise: an irregular (3D-printed) shaped distal (wire and/or polymer) mesh (or net or porous balloon) which is inserted into an aneurysm sac; wherein the distal mesh centroid is a first distance from the aneurysm neck; and a bowl shaped proximal mesh inserted into the aneurysm sac; wherein the proximal mesh centroid is a second distance from the aneurysm neck; wherein the second distance is less than the first distance; wherein the proximal mesh spans the aneurysm neck; wherein the proximal mesh is connected to the distal mesh; and wherein the distal mesh and/or proximal mesh are filled with embolic material (such as microsponges, hydrogels, or coils). An aneurysm occlusion device can comprise: an irregular (3D-printed) shaped distal (wire and/or polymer) mesh (or net or porous balloon) which is inserted into an aneurysm sac; wherein the distal mesh has a first elasticity level; wherein the distal mesh centroid is a first distance from the aneurysm neck; and a disk or ellipsoidal shaped proximal mesh inserted into the aneurysm sac; wherein the proximal mesh has a second elasticity level which is less than the first elasticity level; wherein the proximal mesh centroid is a second distance from the aneurysm neck; wherein the second distance is less than the first distance; wherein the proximal mesh spans the aneurysm neck; and wherein the distal mesh and/or proximal mesh are filled with embolic material (such as microsponges, hydrogels, or coils).

An aneurysm occlusion device can comprise: an irregular (3D-printed) shaped distal (wire and/or polymer) mesh (or net or porous balloon) which is inserted into an aneurysm sac; wherein the distal mesh has a first level of compliance and/or compressibility; wherein the distal mesh centroid is a first distance from the aneurysm neck; and a bowl shaped proximal mesh inserted into the aneurysm sac; wherein the proximal mesh has a second level of compliance and/or compressibility which is greater than the first level; wherein the proximal mesh centroid is a second distance from the aneurysm neck; wherein the second distance is less than the first distance; wherein the proximal mesh spans the aneurysm neck; and wherein the distal mesh and/or proximal mesh are filled with embolic material (such as microsponges, hydrogels, or coils).

An aneurysm occlusion device can comprise: an irregular (3D-printed) shaped distal (wire and/or polymer) mesh (or net or porous balloon) which is inserted into an aneurysm sac; wherein the distal mesh has a first level of conformability, deformable, malleability, and/or plasticity; wherein the distal mesh centroid is a first distance from the aneurysm neck; and a bowl shaped proximal mesh inserted into the aneurysm sac; wherein the proximal mesh has a second level of conformability, deformable, malleability, and/or plasticity which is less than the first level; wherein the proximal mesh centroid is a second distance from the aneurysm neck; wherein the second distance is less than the first distance; wherein the proximal mesh spans the aneurysm neck; wherein the proximal mesh is connected to the distal mesh; and wherein the distal mesh and/or proximal mesh are filled with embolic material (such as microsponges, hydrogels, or coils). An aneurysm occlusion device can comprise: an irregular (3D-printed) shaped distal (wire and/or polymer) mesh (or net or porous balloon) which is inserted into an aneurysm sac; wherein the distal mesh has a first level of softness, durometer, and/or hardness; wherein the distal mesh centroid is a first distance from the aneurysm neck; and a bowl shaped proximal mesh inserted into the aneurysm sac; wherein the proximal mesh has a second level of softness, durometer, and/or hardness; wherein the proximal mesh centroid is a second distance from the aneurysm neck; wherein the second distance is less than the first distance; wherein the proximal mesh spans the aneurysm neck; and wherein the distal mesh and/or proximal mesh are filled with embolic material (such as microsponges, hydrogels, or coils).

An aneurysm occlusion device can comprise: an irregular (3D-printed) shaped distal (wire and/or polymer) mesh (or net or porous balloon) which is inserted into an aneurysm sac; wherein the distal mesh has a first level of tensile strength; wherein the distal mesh centroid is a first distance from the aneurysm neck; and a bowl shaped proximal mesh inserted into the aneurysm sac; wherein the proximal mesh has a second level of tensile strength which is greater than the first level; wherein the proximal mesh centroid is a second distance from the aneurysm neck; wherein the second distance is less than the first distance; wherein the proximal mesh spans the aneurysm neck; wherein the proximal mesh is connected to the distal mesh; and wherein the distal mesh and/or proximal mesh are filled with embolic material (such as microsponges, hydrogels, or coils). An aneurysm occlusion device can comprise: an irregular (3D-printed) shaped distal (wire and/or polymer) mesh (or net or porous balloon) which is inserted into an aneurysm sac; wherein the distal mesh has a first porosity level; wherein the distal mesh centroid is a first distance from the aneurysm neck; and a bowl shaped proximal mesh inserted into the aneurysm sac; wherein the proximal mesh has a second porosity level which is less than the first level; wherein the proximal mesh centroid is a second distance from the aneurysm neck; wherein the second distance is less than the first distance; wherein the proximal mesh spans the aneurysm neck; and wherein the distal mesh and/or proximal mesh are filled with embolic material (such as microsponges, hydrogels, or coils). An aneurysm occlusion device can comprise: an irregular (3D-printed) shaped distal mesh (or net or porous balloon) which is inserted into an aneurysm sac; wherein the distal mesh centroid is a first distance from the aneurysm neck; and a proximal mesh inserted into the aneurysm sac; wherein the proximal mesh is hemispherical, bowl shaped, dome shaped, inverted dome shaped, inverted umbrella shaped, parabolic, paraboloid shaped, prolate hemisphere shaped, reflected parabola shaped, semi-circular, and/or umbrella shaped; wherein the proximal mesh centroid is a second distance from the aneurysm neck; wherein the second distance is less than the first distance; wherein the proximal mesh spans the aneurysm neck; and wherein the distal mesh and/or proximal mesh are filled with embolic material (such as microsponges, hydrogels, or coils).

An aneurysm occlusion device can comprise: an irregular (3D-printed) shaped distal mesh (or net or porous balloon) which is inserted into an aneurysm sac; wherein the distal mesh has a first flexibility level; wherein the distal mesh centroid is a first distance from the aneurysm neck; and a bowl shaped proximal mesh inserted into the aneurysm sac; wherein the proximal mesh has a second flexibility level which is less than the first level; wherein the proximal mesh centroid is a second distance from the aneurysm neck; wherein the second distance is less than the first distance; wherein the proximal mesh spans the aneurysm neck; wherein the proximal mesh is connected to the distal mesh; and wherein the distal mesh and/or proximal mesh are filled with embolic material (such as microsponges, hydrogels, or coils). An aneurysm occlusion device can comprise: an irregular (3D-printed) shaped distal mesh (or net or porous balloon) which is inserted into an aneurysm sac; wherein the distal mesh has a first level of elasticity, modulus of elasticity, and/or Young's modulus; wherein the distal mesh centroid is a first distance from the aneurysm neck; and a disk or ellipsoidal shaped proximal mesh inserted into the aneurysm sac; wherein the proximal mesh has a second level of elasticity, modulus of elasticity, and/or Young's modulus which is less than the first level; wherein the proximal mesh centroid is a second distance from the aneurysm neck; wherein the second distance is less than the first distance; wherein the proximal mesh spans the aneurysm neck; wherein the proximal mesh is connected to the distal mesh; and wherein the distal mesh and/or proximal mesh are filled with embolic material (such as microsponges, hydrogels, or coils).

An aneurysm occlusion device can comprise: an irregular (3D-printed) shaped distal mesh (or net or porous balloon) which is inserted into an aneurysm sac; wherein the distal mesh has a first level of porosity; wherein the distal mesh centroid is a first distance from the aneurysm neck; and a bowl shaped proximal mesh inserted into the aneurysm sac; wherein the proximal mesh has a second level of porosity which is less than the first level; wherein the proximal mesh centroid is a second distance from the aneurysm neck; wherein the second distance is less than the first distance; wherein the proximal mesh spans the aneurysm neck; and wherein the distal mesh and/or proximal mesh are filled with embolic material (such as microsponges, hydrogels, or coils). An aneurysm occlusion device can comprise: an irregular (3D-printed) shaped distal mesh (or net or porous balloon) which is inserted into an aneurysm sac; wherein the distal mesh has a first level of stretchability and/or ductility; wherein the distal mesh centroid is a first distance from the aneurysm neck; and a bowl shaped proximal mesh inserted into the aneurysm sac; wherein the proximal mesh has a second level of stretchability and/or ductility which is less than the first level; wherein the proximal mesh centroid is a second distance from the aneurysm neck; wherein the second distance is less than the first distance; wherein the proximal mesh spans the aneurysm neck; wherein the proximal mesh is connected to the distal mesh; and wherein the distal mesh and/or proximal mesh are filled with embolic material (such as microsponges, hydrogels, or coils).

An aneurysm occlusion device can comprise: a disk or ellipsoidal shaped distal (wire and/or polymer) mesh (or net or porous balloon) which is inserted into an aneurysm sac;

wherein the distal mesh has a first level of elasticity, flexibility, porosity, stiffness, or thickness; wherein the distal mesh centroid is a first distance from the aneurysm neck; and a bowl shaped proximal mesh inserted into the aneurysm sac; wherein the proximal mesh has a second level of elasticity, flexibility, porosity, stiffness, or thickness; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils). An aneurysm occlusion device can comprise: a disk or ellipsoidal shaped distal (wire and/or polymer) mesh (or net or porous balloon) which is inserted into an aneurysm sac; wherein the distal mesh has a first level of radial compliance, compressibility, and/or stiffness; wherein the distal mesh centroid is a first distance from the aneurysm neck; and a bowl shaped proximal mesh inserted into the aneurysm sac; wherein the proximal mesh has a second level of radial compliance, compressibility, and/or stiffness which is greater than the first level; wherein the proximal mesh centroid is a second distance from the aneurysm neck; wherein the second distance is less than the first distance; wherein the proximal mesh spans the aneurysm neck; wherein the proximal mesh is connected to the distal mesh; and wherein the distal mesh and/or proximal mesh are filled with embolic material (such as microsponges, hydrogels, or coils).

An aneurysm occlusion device can comprise: a disk or ellipsoidal shaped distal (wire and/or polymer) mesh (or net or porous balloon) which is inserted into an aneurysm sac; wherein the distal mesh has a first stiffness level; wherein the distal mesh centroid is a first distance from the aneurysm neck; and a bowl shaped proximal mesh inserted into the aneurysm sac; wherein the proximal mesh has a second stiffness level which is greater than the first level; wherein the proximal mesh centroid is a second distance from the aneurysm neck; wherein the second distance is less than the first distance; wherein the proximal mesh spans the aneurysm neck; and wherein the distal mesh and/or proximal mesh are filled with embolic material (such as microsponges, hydrogels, or coils). An aneurysm occlusion device can comprise: a disk or ellipsoidal shaped distal mesh (or net or porous balloon) which is inserted into an aneurysm sac; wherein the distal mesh has a first level of flexibility, Flexural modulus, and/or bendability; wherein the distal mesh centroid is a first distance from the aneurysm neck; and a bowl shaped proximal mesh inserted into the aneurysm sac; wherein the proximal mesh has a second level of flexibility, Flexural modulus, and/or bendability which is less than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: a disk or ellipsoidal shaped distal mesh (or net or porous balloon) which is inserted into an aneurysm sac; wherein the distal mesh has a first level of stiffness, rigidity, and/or resiliency; wherein the distal mesh centroid is a first distance from the aneurysm neck; and a bowl shaped proximal mesh inserted into the aneurysm sac; wherein the proximal mesh has a second level of stiffness, rigidity, and/or resiliency which is greater than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a disk or ellipsoidal shaped distal mesh (or net or porous balloon) which is inserted into an aneurysm sac; wherein the distal mesh has a first thickness; wherein the distal mesh centroid is a first distance from the aneurysm neck; and a bowl shaped proximal mesh with a second thickness which is inserted into the aneurysm sac; wherein the second thickness is greater than the first thickness; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: a disk or ellipsoidal shaped distal mesh inserted into an aneurysm sac; wherein the distal mesh has a first flexibility level; wherein the distal mesh centroid is a first distance from the aneurysm neck; and a bowl shaped proximal mesh inserted into the aneurysm sac; wherein the proximal mesh has a second flexibility level which is less than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a disk or ellipsoidal shaped distal mesh inserted into an aneurysm sac; wherein the distal mesh has a first level of conformability, deformable, malleability, and/or plasticity; wherein the distal mesh centroid is a first distance from the aneurysm neck; and a bowl shaped proximal mesh inserted into the aneurysm sac; wherein the proximal mesh has a second level of conformability, deformable, malleability, and/or plasticity which is less than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: a disk or ellipsoidal shaped distal mesh inserted into an aneurysm sac; wherein the distal mesh has a first level of softness, durometer, and/or hardness; wherein the distal mesh centroid is a first distance from the aneurysm neck; and a bowl shaped proximal mesh inserted into the aneurysm sac; wherein the proximal mesh has a second level of softness, durometer, and/or hardness; wherein the proximal mesh centroid is a second distance from the aneurysm neck; wherein the second distance is less than the first distance; wherein the proximal mesh spans the aneurysm neck; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a disk or ellipsoidal shaped distal mesh inserted into an aneurysm sac; wherein the distal mesh has a first level of tensile strength; wherein the distal mesh centroid is a first distance from the aneurysm neck; and a bowl shaped proximal mesh inserted into the aneurysm sac; wherein the proximal mesh has a second level of tensile strength which is greater than the first level; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils).

An aneurysm occlusion device can comprise: a disk or ellipsoidal shaped distal (wire and/or polymer) mesh inserted into an aneurysm sac; wherein the distal mesh centroid is a first distance from the aneurysm neck; and a bowl shaped proximal mesh inserted into the aneurysm sac; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a disk or ellipsoidal shaped distal (wire and/or polymer) mesh inserted into an aneurysm sac; wherein the distal mesh centroid is a first distance from the aneurysm neck; and a proximal mesh inserted into the aneurysm sac; wherein the proximal mesh is hemispherical, bowl shaped, dome shaped, inverted dome shaped, inverted umbrella shaped, parabolic, paraboloid shaped, prolate hemisphere shaped, reflected parabola shaped, semi-circular, and/or umbrella shaped; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils).

An aneurysm occlusion device can comprise: a disk or ellipsoidal shaped distal (wire and/or polymer) mesh inserted into an aneurysm sac; wherein the distal mesh has a first level of compliance and/or compressibility; wherein the distal mesh centroid is a first distance from the aneurysm neck; and a bowl shaped proximal mesh inserted into the aneurysm sac; wherein the proximal mesh has a second level of compliance and/or compressibility which is greater than the first level; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils). An aneurysm occlusion device can comprise: a disk or ellipsoidal shaped distal (wire and/or polymer) mesh inserted into an aneurysm sac; wherein the distal mesh has a first level of porosity; wherein the distal mesh centroid is a first distance from the aneurysm neck; and a bowl shaped proximal mesh inserted into the aneurysm sac; wherein the proximal mesh has a second level of porosity which is less than the first level; wherein the proximal mesh centroid is a second distance from the aneurysm neck; wherein the second distance is less than the first distance; wherein the proximal mesh spans the aneurysm neck; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: a disk or ellipsoidal shaped distal (wire and/or polymer) mesh inserted into an aneurysm sac; wherein the distal mesh has a first level of stretchability and/or ductility; wherein the distal mesh centroid is a first distance from the aneurysm neck; and a bowl shaped proximal mesh inserted into the aneurysm sac; wherein the proximal mesh has a second level of stretchability and/or ductility which is less than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a disk or ellipsoidal shaped distal (wire and/or polymer) mesh inserted into an aneurysm sac; wherein the distal mesh has a first porosity level; wherein the distal mesh centroid is a first distance from the aneurysm neck; and a bowl shaped proximal mesh inserted into the aneurysm sac; wherein the proximal mesh has a second porosity level which is less than the first level; wherein the proximal mesh centroid is a second distance from the aneurysm neck; wherein the second distance is less than the first distance; wherein the proximal mesh spans the aneurysm neck; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: a distal (wire and/or polymer) mesh inserted into an aneurysm sac; wherein the distal mesh has a selected shape; wherein the distal mesh has a first level of porosity; wherein the distal mesh centroid is a first distance from the aneurysm neck; and a proximal mesh inserted into the aneurysm sac; wherein the proximal mesh also has the selected shape; wherein the proximal mesh has a second level of porosity which is less than the first level; wherein the proximal mesh centroid is a second distance from the aneurysm neck; wherein the second distance is less than the first distance; wherein the proximal mesh spans the aneurysm neck; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a distal (wire and/or polymer) mesh inserted into an aneurysm sac;

wherein the distal mesh is cardioid, crescent shaped, and/or kidney shaped; wherein the distal mesh centroid is a first distance from the aneurysm neck; and a proximal mesh inserted into the aneurysm sac; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils).

An aneurysm occlusion device can comprise: a distal (wire and/or polymer) mesh inserted into an aneurysm sac; wherein the distal mesh is concave; wherein the distal mesh centroid is a first distance from the aneurysm neck; and a proximal mesh inserted into the aneurysm sac; wherein the proximal mesh is concave; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils). An aneurysm occlusion device can comprise: a distal (wire and/or polymer) mesh inserted into an aneurysm sac; wherein the distal mesh is concave; wherein the distal mesh centroid is a first distance from the aneurysm neck; and a proximal mesh inserted into the aneurysm sac; wherein the proximal mesh is concave; wherein the proximal mesh centroid is a second distance from the aneurysm neck; wherein the second distance is less than the first distance; wherein the proximal mesh spans the aneurysm neck; wherein the proximal mesh is connected to the distal mesh; and wherein the proximal mesh is axially-aligned with the distal mesh.

An aneurysm occlusion device can comprise: a distal (wire and/or polymer) mesh inserted into an aneurysm sac; wherein the distal mesh is concave; wherein the distal mesh centroid is a first distance from the aneurysm neck; and a proximal mesh inserted into the aneurysm sac; wherein the proximal mesh is convex; wherein the proximal mesh centroid is a second distance from the aneurysm neck; wherein the second distance is less than the first distance; wherein the proximal mesh spans the aneurysm neck; and wherein the proximal mesh is axially-aligned with the distal mesh. An aneurysm occlusion device can comprise: a distal (wire and/or polymer) mesh inserted into an aneurysm sac; wherein the distal mesh is conical, conic section shaped, football shaped, frustum shaped, and/or wedge shaped; wherein the distal mesh centroid is a first distance from the aneurysm neck; and a proximal mesh inserted into the aneurysm sac; wherein the proximal mesh is hemispherical, bowl shaped, dome shaped, inverted dome shaped, inverted umbrella shaped, parabolic, paraboloid shaped, prolate hemisphere shaped, reflected parabola shaped, semi-circular, and/or umbrella shaped; wherein the proximal mesh centroid is a second distance from the aneurysm neck; wherein the second distance is less than the first distance; wherein the proximal mesh spans the aneurysm neck; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: a distal (wire and/or polymer) mesh inserted into an aneurysm sac; wherein the distal mesh is convex; wherein the distal mesh centroid is a first distance from the aneurysm neck; and a proximal mesh inserted into the aneurysm sac; wherein the proximal mesh is convex; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils).

An aneurysm occlusion device can comprise: a distal (wire and/or polymer) mesh inserted into an aneurysm sac; wherein the distal mesh is convex; wherein the distal mesh centroid is a first distance from the aneurysm neck; and a proximal mesh inserted into the aneurysm sac; wherein the proximal mesh is convex; wherein the proximal mesh centroid is a second distance from the aneurysm neck; wherein the second distance is less than the first distance; wherein the proximal mesh spans the aneurysm neck; wherein the proximal mesh is connected to the distal mesh; and wherein the proximal mesh is axially-aligned with the distal mesh. An aneurysm occlusion device can comprise: a distal (wire and/or polymer) mesh inserted into an aneurysm sac; wherein the distal mesh is convex; wherein the distal mesh centroid is a first distance from the aneurysm neck; and a proximal mesh inserted into the aneurysm sac; wherein the proximal mesh is concave; wherein the proximal mesh centroid is a second distance from the aneurysm neck; wherein the second distance is less than the first distance; wherein the proximal mesh spans the aneurysm neck; and wherein the proximal mesh is axially-aligned with the distal mesh.

An aneurysm occlusion device can comprise: a distal (wire and/or polymer) mesh inserted into an aneurysm sac; wherein the distal mesh is disk shaped, Frisbee™ shaped, pancake shaped, and/or platter shaped; wherein the distal mesh centroid is a first distance from the aneurysm neck; and a proximal mesh inserted into the aneurysm sac; wherein the proximal mesh is hemispherical, bowl shaped, dome shaped, inverted dome shaped, inverted umbrella shaped, parabolic, paraboloid shaped, prolate hemisphere shaped, reflected parabola shaped, semi-circular, and/or umbrella shaped; wherein the proximal mesh centroid is a second distance from the aneurysm neck; wherein the second distance is less than the first distance; wherein the proximal mesh spans the aneurysm neck; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a distal (wire and/or polymer) mesh inserted into an aneurysm sac; wherein the distal mesh is egg shaped, beehive shaped, mushroom shaped, pear shaped, tear drop shaped, and/or water drop shaped; wherein the distal mesh centroid is a first distance from the aneurysm neck; and a bowl shaped proximal mesh inserted into the aneurysm sac; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: a distal (wire and/or polymer) mesh inserted into an aneurysm sac;

wherein the distal mesh is ellipsoidal, apple-shaped, or egg-shaped; wherein the distal mesh has a first elasticity level; wherein the distal mesh centroid is a first distance from the aneurysm neck; and a proximal (wire and/or polymer) mesh inserted into the aneurysm sac; wherein the proximal mesh is also generally ellipsoidal, apple-shaped, or egg-shaped; wherein the proximal mesh has a second elasticity level which is less than the first elasticity level; wherein the proximal mesh centroid is a second distance from the aneurysm neck; wherein the second distance is less than the first distance; wherein the proximal mesh spans across the inside of the aneurysm neck; and wherein the proximal mesh is (centrally) connected to the distal mesh. An aneurysm occlusion device can comprise: a distal (wire and/or polymer) mesh inserted into an aneurysm sac; wherein the distal mesh is generally ellipsoidal, egg shaped, or apple shaped; wherein the distal mesh has a first flexibility level; wherein the distal mesh centroid is a first distance from the aneurysm neck; and a proximal mesh inserted into the aneurysm sac; wherein the proximal mesh is bowl or paraboloid shaped with a distal-facing concavity; wherein the proximal mesh has a second flexibility level which is less than the first flexibility level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: a distal (wire and/or polymer) mesh inserted into an aneurysm sac; wherein the distal mesh is generally ellipsoidal, egg shaped, or apple shaped; wherein the distal mesh has a first flexibility level; and a proximal mesh inserted into the aneurysm sac; wherein the proximal mesh is bowl or paraboloid shaped with a distal-facing concavity; wherein the proximal mesh has a second flexibility level which is less than the first flexibility level; wherein the proximal mesh spans the aneurysm neck; wherein a portion of the distal mesh is within the concavity of the proximal mesh; and wherein the distal mesh and/or proximal mesh are filled with embolic material (such as microsponges, hydrogels, or coils). An aneurysm occlusion device can comprise: a distal (wire and/or polymer) mesh inserted into an aneurysm sac; wherein the distal mesh is generally ellipsoidal, egg shaped, or apple shaped; wherein the distal mesh has a first flexibility level; and a proximal mesh inserted into the aneurysm sac; wherein the proximal mesh is bowl or paraboloid shaped with a distal-facing concavity; wherein the proximal mesh has a second flexibility level which is less than the first flexibility level; wherein the proximal mesh spans the aneurysm neck; and wherein the proximal mesh is inside the distal mesh.

An aneurysm occlusion device can comprise: a distal (wire and/or polymer) mesh inserted into an aneurysm sac; wherein the distal mesh is generally ellipsoidal, egg shaped, or apple shaped; wherein the distal mesh has a first porosity level; wherein the distal mesh centroid is a first distance from the aneurysm neck; and a proximal mesh inserted into the aneurysm sac; wherein the proximal mesh is bowl or paraboloid shaped with a distal-facing concavity; wherein the proximal mesh has a second porosity level which is less than the first porosity level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; and wherein the distal mesh and/or proximal mesh are filled with embolic material (such as microsponges, hydrogels, or coils).

An aneurysm occlusion device can comprise: a distal (wire and/or polymer) mesh inserted into an aneurysm sac; wherein the distal mesh is generally ellipsoidal, egg shaped, or apple shaped; wherein the distal mesh has a first porosity level; and a proximal mesh inserted into the aneurysm sac; wherein the proximal mesh is bowl or paraboloid shaped with a distal-facing concavity; wherein the proximal mesh has a second porosity level which is less than the first porosity level; wherein the proximal mesh spans the aneurysm neck; and wherein the distal mesh and/or proximal mesh are filled with embolic material (such as microsponges, hydrogels, or coils). An aneurysm occlusion device can comprise: a distal (wire and/or polymer) mesh inserted into an aneurysm sac; wherein the distal mesh is generally ellipsoidal, egg shaped, or apple shaped; wherein the distal mesh has a first porosity level; and a proximal mesh inserted into the aneurysm sac; wherein the proximal mesh is bowl or paraboloid shaped with a distal-facing concavity; wherein the proximal mesh has a second porosity level which is less than the first porosity level; wherein the proximal mesh spans the aneurysm neck; and wherein the proximal mesh is inside the distal mesh.

An aneurysm occlusion device can comprise: a distal mesh inserted into an aneurysm sac; wherein the distal mesh is a multi-lobed globular structure; wherein the distal mesh has a first stiffness level; wherein the distal mesh centroid is a first distance from the aneurysm neck; and a bowl shaped proximal mesh inserted into the aneurysm sac; wherein the proximal mesh has a second stiffness level which is greater than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is connected to the distal mesh; and wherein the distal mesh and/or proximal mesh are filled with embolic material (such as microsponges, hydrogels, or coils).

An aneurysm occlusion device can comprise: a distal mesh inserted into an aneurysm sac; wherein the distal mesh is concave; wherein the distal mesh centroid is a first distance from the aneurysm neck; and a proximal mesh inserted into the aneurysm sac; wherein the proximal mesh is convex; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils). An aneurysm occlusion device can comprise: a distal mesh inserted into an aneurysm sac; wherein the distal mesh is conical, conic section shaped, football shaped, frustum shaped, and/or wedge shaped; wherein the distal mesh centroid is a first distance from the aneurysm neck; and a bowl shaped proximal mesh inserted into the aneurysm sac; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: a distal mesh inserted into an aneurysm sac; wherein the distal mesh is convex; wherein the distal mesh centroid is a first distance from the aneurysm neck; and a proximal mesh inserted into the aneurysm sac; wherein the proximal mesh is concave; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils).

An aneurysm occlusion device can comprise: a distal mesh inserted into an aneurysm sac; wherein the distal mesh is disk shaped, Frisbee™ shaped, pancake shaped, and/or platter shaped; wherein the distal mesh centroid is a first distance from the aneurysm neck; and a bowl shaped proximal mesh inserted into the aneurysm sac; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a distal mesh inserted into an aneurysm sac; wherein the distal mesh is egg shaped, beehive shaped, mushroom shaped, pear shaped, tear drop shaped, and/or water drop shaped; wherein the distal mesh centroid is a first distance from the aneurysm neck; and a proximal mesh inserted into the aneurysm sac; wherein the proximal mesh is hemispherical, bowl shaped, dome shaped, inverted dome shaped, inverted umbrella shaped, parabolic, paraboloid shaped, prolate hemisphere shaped, reflected parabola shaped, semi-circular, and/or umbrella shaped; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils).

An aneurysm occlusion device can comprise: a distal mesh inserted into an aneurysm sac; wherein the distal mesh is ellipsoidal, apple-shaped, or egg-shaped; wherein the distal mesh has a first elasticity level; wherein the distal mesh centroid is a first distance from the aneurysm neck; and a proximal (wire and/or polymer) mesh inserted into the aneurysm sac; wherein the proximal mesh is also generally ellipsoidal, apple-shaped, or egg-shaped; wherein the proximal mesh has a second elasticity level which is less than the first elasticity level; wherein the proximal mesh centroid is a second distance from the aneurysm neck; wherein the second distance is less than the first distance; wherein the proximal mesh spans across the inside of the aneurysm neck; wherein the proximal mesh is (centrally) connected to the distal mesh; and wherein the distal mesh and/or proximal mesh are filled with embolic material (such as microsponges, hydrogels, or coils).

An aneurysm occlusion device can comprise: a distal mesh inserted into an aneurysm sac; wherein the distal mesh is generally ellipsoidal, egg shaped, or apple shaped; and a proximal mesh inserted into the aneurysm sac; wherein the proximal mesh is bowl or paraboloid shaped with a distal-facing concavity; wherein the proximal mesh spans the aneurysm neck. An aneurysm occlusion device can comprise: a distal mesh inserted into an aneurysm sac; wherein the distal mesh is generally ellipsoidal, egg shaped, or apple shaped; wherein the distal mesh has a first flexibility level; and a proximal mesh inserted into the aneurysm sac; wherein the proximal mesh is bowl or paraboloid shaped with a distal-facing concavity; wherein the proximal mesh has a second flexibility level which is less than the first flexibility level; wherein the proximal mesh spans the aneurysm neck; and wherein a portion of the distal mesh is within the concavity of the proximal mesh.

An aneurysm occlusion device can comprise: a distal mesh inserted into an aneurysm sac; wherein the distal mesh is generally ellipsoidal, egg shaped, or apple shaped; wherein the distal mesh has a first flexibility level; wherein the distal mesh centroid is a first distance from the aneurysm neck; and a proximal mesh inserted into the aneurysm sac; wherein the proximal mesh is bowl or paraboloid shaped with a distal-facing concavity; wherein the proximal mesh has a second flexibility level which is less than the first flexibility level; wherein the proximal mesh centroid is a second distance from the aneurysm neck; wherein the second distance is less than the first distance; wherein the proximal mesh spans the aneurysm neck; and wherein the distal mesh and/or proximal mesh are filled with embolic material (such as microsponges, hydrogels, or coils).

An aneurysm occlusion device can comprise: a distal mesh inserted into an aneurysm sac; wherein the distal mesh is generally ellipsoidal, egg shaped, or apple shaped; wherein the distal mesh has a first porosity level; and a proximal mesh inserted into the aneurysm sac; wherein the proximal mesh is bowl or paraboloid shaped with a distal-facing concavity; wherein the proximal mesh has a second porosity level which is less than the first porosity level; wherein the proximal mesh spans the aneurysm neck. An aneurysm occlusion device can comprise: a distal mesh inserted into an aneurysm sac; wherein the distal mesh is generally ellipsoidal, egg shaped, or apple shaped; wherein the distal mesh has a first porosity level; wherein the distal mesh centroid is a first distance from the aneurysm neck; and a proximal mesh inserted into the aneurysm sac; wherein the proximal mesh is bowl or paraboloid shaped with a distal-facing concavity; wherein the proximal mesh has a second porosity level which is less than the first porosity level; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils).

An aneurysm occlusion device can comprise: a distal mesh inserted into an aneurysm sac; wherein the distal mesh is globular and multi-lobed; and a proximal (wire and/or polymer) mesh inserted into the aneurysm sac; wherein the proximal mesh is also globular and multi-lobed; wherein the second distance is less than the first distance; wherein the proximal mesh spans across the inside of the aneurysm neck; wherein the proximal mesh is centrally connected to the distal mesh; and wherein the distal mesh and/or proximal mesh are filled with embolic material (such as microsponges, hydrogels, or coils). An aneurysm occlusion device can comprise: a distal mesh inserted into an aneurysm sac;

wherein the distal mesh is globular and multi-lobed; and a proximal (wire and/or polymer) mesh inserted into the aneurysm sac; wherein the proximal mesh is also globular and multi-lobed; wherein the second distance is less than the first distance; wherein the proximal mesh spans across the inside of the aneurysm neck; and wherein the proximal mesh is centrally connected to the distal mesh.

An aneurysm occlusion device can comprise: a distal mesh inserted into an aneurysm sac; wherein the distal mesh is globular and multi-lobed; wherein the distal mesh centroid is a first distance from the aneurysm neck; and a proximal (wire and/or polymer) mesh inserted into the aneurysm sac; wherein the proximal mesh is also globular and multi-lobed; wherein the proximal mesh centroid is a second distance from the aneurysm neck; wherein the second distance is less than the first distance; wherein the proximal mesh spans across the inside of the aneurysm neck; wherein the proximal mesh is (centrally) connected to the distal mesh; and wherein the distal mesh and/or proximal mesh are filled with embolic material (such as microsponges, hydrogels, or coils). An aneurysm occlusion device can comprise: a distal mesh inserted into an aneurysm sac; wherein the distal mesh is globular and multi-lobed; wherein the distal mesh centroid is a first distance from the aneurysm neck; and a proximal (wire and/or polymer) mesh inserted into the aneurysm sac; wherein the proximal mesh is also globular and multi-lobed; wherein the proximal mesh centroid is a second distance from the aneurysm neck; wherein the second distance is less than the first distance; wherein the proximal mesh spans across the inside of the aneurysm neck; and wherein the proximal mesh is (centrally) connected to the distal mesh.

An aneurysm occlusion device can comprise: a distal mesh inserted into an aneurysm sac; wherein the distal mesh is toroidal, ring shaped, doughnut shaped, tire shaped, cylindrical, tubular, and/or wheel shaped; wherein the distal mesh centroid is a first distance from the aneurysm neck; and a bowl shaped proximal mesh inserted into the aneurysm sac; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a distal polymer and metal mesh inserted into an aneurysm sac; wherein the distal mesh centroid is a first distance from the aneurysm neck; wherein the distal mesh has a first ratio of polymer material to metal material; and a proximal polymer and metal mesh inserted into the aneurysm sac; wherein the proximal mesh centroid is a second distance from the aneurysm neck which is less than the first distance; wherein the proximal mesh has a second ratio of polymer material to metal material which is less than the first ratio.

An aneurysm occlusion device can comprise: a distal polymer and metal mesh inserted into an aneurysm sac; wherein the distal mesh centroid is a first distance from the aneurysm neck; wherein the distal mesh has a first ratio of polymer material to metal material; and a proximal polymer and metal mesh inserted into the aneurysm sac; wherein the proximal mesh centroid is a second distance from the aneurysm neck which is less than the first distance; wherein the proximal mesh has a second ratio of polymer material to metal material which is less than the first ratio; and wherein the distal mesh and/or the proximal mesh are filled with embolic material (such as microsponges, hydrogels, or coils). An aneurysm occlusion device can comprise: a distal polymer and metal mesh inserted into an aneurysm sac; wherein the distal mesh has a first ratio of polymer material to metal material; and a proximal polymer and metal mesh inserted into the aneurysm sac; wherein the proximal mesh has a second ratio of polymer material to metal material which is less than the first ratio; wherein the proximal mesh spans the aneurysm; and wherein the distal mesh and/or the proximal mesh are filled with embolic material (such as microsponges, hydrogels, or coils).

An aneurysm occlusion device can comprise: a distal polymer mesh (or net) which is inserted into an aneurysm sac; wherein the distal mesh or net is ellipsoidal, apple-shaped, or egg-shaped; wherein the distal mesh or net has a first elasticity level; wherein the distal mesh or net centroid is a first distance from the aneurysm neck; and a proximal polymer mesh (or net) which is inserted into the aneurysm sac; wherein the proximal mesh or net is also generally ellipsoidal, apple-shaped, or egg-shaped; wherein the proximal mesh or net has a second elasticity level which is less than the first elasticity level; wherein the proximal mesh or net centroid is a second distance from the aneurysm neck; wherein the second distance is less than the first distance; wherein the proximal mesh or net spans across the inside of the aneurysm neck; wherein the proximal mesh or net is (centrally) connected to the distal mesh or net; and wherein the distal mesh or net and/or proximal mesh or net are filled with embolic material (such as microsponges, hydrogels, or coils). An aneurysm occlusion device can comprise: a distal polymer mesh (or net) which is inserted into an aneurysm sac; wherein the distal mesh or net is ellipsoidal, apple-shaped, or egg-shaped; wherein the distal mesh or net has a first elasticity level; wherein the distal mesh or net centroid is a first distance from the aneurysm neck; and a proximal polymer mesh (or net) which is inserted into the aneurysm sac; wherein the proximal mesh or net is also generally ellipsoidal, apple-shaped, or egg-shaped; wherein the proximal mesh or net has a second elasticity level which is less than the first elasticity level; wherein the proximal mesh or net centroid is a second distance from the aneurysm neck; wherein the second distance is less than the first distance; wherein the proximal mesh or net spans across the inside of the aneurysm neck; and wherein the proximal mesh or net is (centrally) connected to the distal mesh or net.

An aneurysm occlusion device can comprise: a distal polymer mesh (or net) which is inserted into an aneurysm sac; wherein the distal polymer mesh (or net) is filled with embolic material; and a proximal wire mesh inserted into the aneurysm sac; wherein the proximal wire mesh has a concave distal side and a convex proximal side which spans the aneurysm neck; and wherein a portion of the distal polymer mesh (or net) is within the concavity of the proximal wire mesh. An aneurysm occlusion device can comprise: a distal polymer mesh (or net) which is inserted into an aneurysm sac; wherein the distal polymer mesh (or net) is filled with embolic material (such as microsponges, hydrogels, or coils); and a proximal wire mesh inserted into the aneurysm sac; wherein the proximal wire mesh has a concave distal side and a convex proximal side which spans the aneurysm neck; and wherein the proximal wire mesh is inside the distal polymer mesh (or net).

An aneurysm occlusion device can comprise: a distal porous balloon which is inserted into an aneurysm sac; wherein the distal porous balloon is ellipsoidal, apple-shaped, or egg-shaped; wherein the distal porous balloon has a first elasticity level; wherein the distal porous balloon centroid is a first distance from the aneurysm neck; and a proximal porous balloon which is inserted into the aneurysm sac; wherein the proximal porous balloon is also generally ellipsoidal, apple-shaped, or egg-shaped; wherein the proximal porous balloon has a second elasticity level which is less than the first elasticity level; wherein the proximal porous balloon centroid is a second distance from the aneurysm neck; wherein the second distance is less than the first distance; wherein the proximal porous balloon spans across the inside of the aneurysm neck; wherein the proximal porous balloon is (centrally) connected to the distal porous balloon; and wherein the distal porous balloon and/or proximal porous balloon are filled with embolic material (such as microsponges, hydrogels, or coils). An aneurysm occlusion device can comprise: a distal porous balloon which is inserted into an aneurysm sac; wherein the distal porous balloon is ellipsoidal, apple-shaped, or egg-shaped; wherein the distal porous balloon has a first elasticity level; wherein the distal porous balloon centroid is a first distance from the aneurysm neck; and a proximal porous balloon which is inserted into the aneurysm sac; wherein the proximal porous balloon is also generally ellipsoidal, apple-shaped, or egg-shaped; wherein the proximal porous balloon has a second elasticity level which is less than the first elasticity level; wherein the proximal porous balloon centroid is a second distance from the aneurysm neck; wherein the second distance is less than the first distance; wherein the proximal porous balloon spans across the inside of the aneurysm neck; and wherein the proximal porous balloon is (centrally) connected to the distal porous balloon.

An aneurysm occlusion device can comprise: a distal wire mesh inserted into an aneurysm sac; wherein the distal wire mesh is ellipsoidal, apple-shaped, or egg-shaped; wherein the distal wire mesh has a first elasticity level; wherein the distal wire mesh centroid is a first distance from the aneurysm neck; and a proximal wire mesh inserted into the aneurysm sac; wherein the proximal wire mesh is also generally ellipsoidal, apple-shaped, or egg-shaped; wherein the proximal wire mesh has a second elasticity level which is less than the first elasticity level; wherein the proximal wire mesh centroid is a second distance from the aneurysm neck; wherein the second distance is less than the first distance; wherein the proximal wire mesh spans across the inside of the aneurysm neck; wherein the proximal wire mesh is (centrally) connected to the distal wire mesh; and wherein the distal wire mesh and/or proximal wire mesh are filled with embolic material (such as microsponges, hydrogels, or coils). An aneurysm occlusion device can comprise: a distal wire mesh inserted into an aneurysm sac; wherein the distal wire mesh is ellipsoidal, apple-shaped, or egg-shaped; wherein the distal wire mesh has a first elasticity level; wherein the distal wire mesh centroid is a first distance from the aneurysm neck; and a proximal wire mesh inserted into the aneurysm sac; wherein the proximal wire mesh is also generally ellipsoidal, apple-shaped, or egg-shaped; wherein the proximal wire mesh has a second elasticity level which is less than the first elasticity level; wherein the proximal wire mesh centroid is a second distance from the aneurysm neck; wherein the second distance is less than the first distance; wherein the proximal wire mesh spans across the inside of the aneurysm neck; and wherein the proximal wire mesh is (centrally) connected to the distal wire mesh.

An aneurysm occlusion device can comprise: a first (wire and/or polymer) mesh (or net or porous balloon) which is inserted into an aneurysm sac, wherein the distal mesh has a sinusoidal shape (such as a 3D shape created by rotating a sinusoidal curve), and wherein the distal mesh centroid is a first distance from the aneurysm neck; and a proximal mesh (such as a wire mesh) which is inserted into the aneurysm sac; wherein the proximal mesh is paraboloid shaped; wherein the proximal mesh centroid is a second distance from the aneurysm neck; wherein the second distance is less than the first distance; wherein the proximal mesh spans the aneurysm neck; wherein the proximal mesh is (centrally) connected to the distal mesh. An aneurysm occlusion device can comprise: a first (wire and/or polymer) mesh (or net or porous balloon) which is inserted into an aneurysm sac; wherein the first mesh has a first level of flexibility; wherein the first mesh is sufficiently flexible to conform to the walls of even an irregularly-shaped aneurysm; wherein the first mesh is expanded by being filled with embolic material; and a second mesh inserted into the aneurysm sac; wherein the second mesh encircles the first mesh; wherein the second mesh has a second level of flexibility which is less than the first level of flexibility.

An aneurysm occlusion device can comprise: a first (wire and/or polymer) mesh (or net or porous balloon) which is inserted into an aneurysm sac; wherein the first mesh has a first level of flexibility; wherein the first mesh is sufficiently flexible to conform to the walls of even an irregularly-shaped aneurysm; wherein the first mesh is expanded by being filled with embolic material (such as microsponges, hydrogels, or coils); and a second mesh inserted into the aneurysm sac; wherein the second mesh encircles the widest circumference of the first mesh; wherein the second mesh has a second level of flexibility which is less than the first level of flexibility. An aneurysm occlusion device can comprise: a first mesh (or net or porous balloon) which is inserted into an aneurysm sac; wherein the first mesh has a first level of flexibility; wherein the first mesh is sufficiently flexible to conform to the walls of even an irregularly-shaped aneurysm; wherein the first mesh is expanded by being filled with embolic material (such as microsponges, hydrogels, or coils); and a second mesh inserted into the aneurysm sac; wherein the second mesh encircles the middle of the first mesh; wherein the second mesh has a second level of flexibility which is less than the first level of flexibility.

An aneurysm occlusion device can comprise: a first mesh inserted into an aneurysm sac; wherein the first mesh has an irregular (3D-printed) shape; wherein the first mesh has a first elasticity level; and a second mesh inserted into the aneurysm sac; wherein the second mesh is ring shaped; wherein the second mesh has a second elasticity level which is less than the first elasticity level; and wherein the second mesh is connected to the first mesh. An aneurysm occlusion device can comprise: a frustum shaped distal (wire and/or polymer) mesh inserted into an aneurysm sac; wherein the distal mesh centroid is a first distance from the aneurysm neck; and a bowl shaped proximal mesh inserted into the aneurysm sac; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: a frustum shaped distal (wire and/or polymer) mesh inserted into an aneurysm sac; wherein the distal mesh has a first flexibility level; wherein the distal mesh centroid is a first distance from the aneurysm neck; and a bowl shaped proximal mesh inserted into the aneurysm sac; wherein the proximal mesh has a second flexibility level which is less than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: a frustum shaped distal (wire and/or polymer) mesh inserted into an aneurysm sac; wherein the distal mesh has a first level of compliance and/or compressibility; wherein the distal mesh centroid is a first distance from the aneurysm neck; and a bowl shaped proximal mesh inserted into the aneurysm sac; wherein the proximal mesh has a second level of compliance and/or compressibility which is greater than the first level; wherein the proximal mesh centroid is a second distance from the aneurysm neck; wherein the second distance is less than the first distance; wherein the proximal mesh spans the aneurysm neck; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a frustum shaped distal (wire and/or polymer) mesh inserted into an aneurysm sac; wherein the distal mesh has a first level of porosity; wherein the distal mesh centroid is a first distance from the aneurysm neck; and a bowl shaped proximal mesh inserted into the aneurysm sac; wherein the proximal mesh has a second level of porosity which is less than the first level; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils).

An aneurysm occlusion device can comprise: a frustum shaped distal (wire and/or polymer) mesh inserted into an aneurysm sac; wherein the distal mesh has a first level of softness, durometer, and/or hardness; wherein the distal mesh centroid is a first distance from the aneurysm neck; and a bowl shaped proximal mesh inserted into the aneurysm sac; wherein the proximal mesh has a second level of softness, durometer, and/or hardness; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: a frustum shaped distal (wire and/or polymer) mesh inserted into an aneurysm sac; wherein the distal mesh has a first level of tensile strength; wherein the distal mesh centroid is a first distance from the aneurysm neck; and a bowl shaped proximal mesh inserted into the aneurysm sac; wherein the proximal mesh has a second level of tensile strength which is greater than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a frustum shaped distal (wire and/or polymer) mesh inserted into an aneurysm sac; wherein the distal mesh has a first porosity level; wherein the distal mesh centroid is a first distance from the aneurysm neck; and a bowl shaped proximal mesh inserted into the aneurysm sac; wherein the proximal mesh has a second porosity level which is less than the first level; wherein the proximal mesh centroid is a second distance from the aneurysm neck; wherein the second distance is less than the first distance; wherein the proximal mesh spans the aneurysm neck; wherein the proximal mesh is axially-aligned with the distal mesh; and wherein the distal mesh and/or proximal mesh are filled with embolic material (such as microsponges, hydrogels, or coils).

An aneurysm occlusion device can comprise: a frustum shaped distal mesh inserted into an aneurysm sac; wherein the distal mesh centroid is a first distance from the aneurysm neck; and a proximal mesh inserted into the aneurysm sac; wherein the proximal mesh is hemispherical, bowl shaped, dome shaped, inverted dome shaped, inverted umbrella shaped, parabolic, paraboloid shaped, prolate hemisphere shaped, reflected parabola shaped, semi-circular, and/or umbrella shaped; wherein the proximal mesh centroid is a second distance from the aneurysm neck; wherein the second distance is less than the first distance; wherein the proximal mesh spans the aneurysm neck; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a frustum shaped distal mesh inserted into an aneurysm sac; wherein the distal mesh has a first level of conformability, deformable, malleability, and/or plasticity; wherein the distal mesh centroid is a first distance from the aneurysm neck; and a bowl shaped proximal mesh inserted into the aneurysm sac; wherein the proximal mesh has a second level of conformability, deformable, malleability, and/or plasticity which is less than the first level; wherein the proximal mesh centroid is a second distance from the aneurysm neck; wherein the second distance is less than the first distance; wherein the proximal mesh spans the aneurysm neck; wherein a portion of the distal mesh is within the concavity of the proximal mesh; wherein the proximal mesh is axially-aligned with the distal mesh; and wherein the distal mesh and/or proximal mesh are filled with embolic material (such as microsponges, hydrogels, or coils).

An aneurysm occlusion device can comprise: a frustum shaped distal mesh inserted into an aneurysm sac; wherein the distal mesh has a first level of stretchability and/or ductility; wherein the distal mesh centroid is a first distance from the aneurysm neck; and a bowl shaped proximal mesh inserted into the aneurysm sac; wherein the proximal mesh has a second level of stretchability and/or ductility which is less than the first level; wherein the proximal mesh centroid is a second distance from the aneurysm neck; wherein the second distance is less than the first distance; wherein the proximal mesh spans the aneurysm neck; wherein the proximal mesh is connected to the distal mesh; wherein the proximal mesh is axially-aligned with the distal mesh; and wherein the distal mesh and/or proximal mesh are filled with embolic material (such as microsponges, hydrogels, or coils). An aneurysm occlusion device can comprise: a generally spherical (wire and/or polymer) mesh (or net or porous balloon) which is inserted into an aneurysm sac; and a ring-shaped (wire) mesh inserted into the aneurysm sac; and wherein the ring-shaped mesh spans the circumference the spherical mesh (either inside or outside the mesh).

I claim:

1. An intrasaccular aneurysm occlusion device comprising:
   an expandable net or mesh which is inserted into an aneurysm sac; wherein a proximal portion of the expandable net or mesh is configured to be a first distance from the aneurysm neck after the net or mesh has been inserted into the aneurysm sac; wherein a distal portion of the expandable net or mesh is configured to be a second distance from the aneurysm neck after the net or mesh has been inserted into the aneurysm sac; wherein the second distance is greater than the first distance; wherein the proximal portion of the expandable net or mesh has a first level of flexibility, elasticity, conformability, and/or compliance; wherein the distal portion of the expandable net or mesh has a second level of flexibility, elasticity, conformability, and/or compliance; and wherein second level of flexibility, elasticity, conformability, and/or compliance is greater than the first level of flexibility, elasticity, conformability, and/or compliance;
   a plurality of three-dimensional embolic members which are inserted into and retained within the expandable net or mesh after the net or mesh has been inserted into the aneurysm sac, wherein the proximal portion of the net or mesh self expands after the net or mesh has been inserted into the aneurysm sac, and wherein the distal portion of the net or mesh is expanded by insertion and retention of the plurality of three-dimensional embolic members inside the net or mesh after the net or mesh has been inserted into the aneurysm sac; and
   one or more longitudinal strands which are inserted into the aneurysm sac, wherein the one or more longitudinal strands connect embolic members in the plurality of three-dimensional embolic members to each other, wherein the embolic members in the plurality of three-dimensional embolic members have progressively lower durometer values as one progresses along the strand in a distal to proximal manner, and wherein the embolic members in the plurality of three-dimensional embolic members have an average durometer value which is less than 70.

2. The intrasaccular aneurysm occlusion device in claim 1 wherein embolic members in a distal portion of a longitudinal strand have an average durometer value in the range of 25 to 50 and embolic members in a proximal portion of the longitudinal strand have an average durometer value in the range of 10 to 30.

3. An intrasaccular aneurysm occlusion device comprising:
   an expandable net or mesh which is inserted into an aneurysm sac; wherein a proximal portion of the expandable net or mesh is configured to be a first distance from the aneurysm neck after the net or mesh has been inserted into the aneurysm sac; wherein a distal portion of the expandable net or mesh is configured to be a second distance from the aneurysm neck after the net or mesh has been inserted into the aneurysm sac; wherein the second distance is greater than the first distance; wherein the proximal portion of the expandable net or mesh has a first level of flexibility, elasticity, conformability, and/or compliance; wherein the distal portion of the expandable net or mesh has a second level of flexibility, elasticity, conformability, and/or compliance; wherein second level of flexibility, elasticity, conformability, and/or compliance is greater than the first level of flexibility, elasticity, conformability, and/or compliance; wherein the proximal portion of the net or mesh is made from one or more materials with a first average durometer and the distal portion of the net or mesh is made from one or more materials with a second average durometer, wherein the second average durometer is less than the first average durometer; and wherein the proximal portion of the net or mesh self expands after the net or mesh has been inserted into the aneurysm sac and the distal portion of the net or mesh is expanded by insertion and retention of the plurality of embolic members inside the net or mesh after the net or mesh has been inserted into the aneurysm sac;
   a plurality of three-dimensional embolic members which are inserted into and retained within the expandable net or mesh after the net or mesh has been inserted into the aneurysm sac; and
   one or more longitudinal strands which are inserted into the aneurysm sac, wherein the one or more longitudinal strands connect embolic members in the plurality of three-dimensional embolic members to each other, wherein the embolic members in the plurality of three-dimensional embolic members have progressively lower durometer values as one progresses along the strand in a distal to proximal manner, and wherein the embolic members in the plurality of three-dimensional embolic members have an average durometer value which is less than 70.

4. The intrasaccular aneurysm occlusion device in claim 3 wherein embolic members in a distal portion of a longitudinal strand have an average durometer value in the range of 25 to 50 and embolic members in a proximal portion of the longitudinal strand have an average durometer value in the range of 10 to 30.

* * * * *